US011293927B2

(12) United States Patent
Wigle et al.

(10) Patent No.: US 11,293,927 B2
(45) Date of Patent: Apr. 5, 2022

(54) SCREENING METHODS FOR PARP MODULATORS

(71) Applicant: Ribon Therapeutics, Inc., Cambridge, MA (US)

(72) Inventors: Timothy J. N. Wigle, Cambridge, MA (US); Danielle J. Blackwell, Medford, MA (US); Kevin Wayne Kuntz, Woburn, MA (US); Melissa Marie Vasbinder, Newton, MA (US); Laurie B. Schenkel, Somerville, MA (US); Kerren Kalai Swinger, Lexington, MA (US)

(73) Assignee: Ribon Therapeutics, Inc., Cambridge, MA (US)

( * ) Notice: Subject to any disclaimer, the term of this patent is extended or adjusted under 35 U.S.C. 154(b) by 105 days.

(21) Appl. No.: 16/397,410

(22) Filed: Apr. 29, 2019

(65) Prior Publication Data
US 2019/0331688 A1    Oct. 31, 2019

Related U.S. Application Data

(60) Provisional application No. 62/664,595, filed on Apr. 30, 2018.

(51) Int. Cl.
| | |
|---|---|
| *G01N 33/58* | (2006.01) |
| *G01N 33/573* | (2006.01) |
| *C07D 491/22* | (2006.01) |
| *C07D 491/04* | (2006.01) |
| *C07D 493/10* | (2006.01) |
| *C07D 495/04* | (2006.01) |
| *C07F 5/02* | (2006.01) |

(52) U.S. Cl.
CPC ......... *G01N 33/582* (2013.01); *C07D 491/22* (2013.01); *C07D 493/10* (2013.01); *C07D 495/04* (2013.01); *C07F 5/027* (2013.01); *G01N 33/573* (2013.01); *G01N 2333/91142* (2013.01)

(58) Field of Classification Search
CPC .. G01N 33/533; G01N 33/582; G01N 33/542; G01N 33/573; G01N 2333/91142; C07F 5/027; C07D 491/22; C07D 495/04; C07D 493/10
See application file for complete search history.

(56) References Cited

U.S. PATENT DOCUMENTS

| | | | |
|---|---|---|---|
| 6,432,632 | B2 | 8/2002 | Nakayama et al. |
| 10,550,105 | B2 | 2/2020 | Vasbinder et al. |
| 10,870,641 | B2 | 12/2020 | Vasbinder et al. |
| 11,014,913 | B2 | 5/2021 | Vasbinder et al. |
| 2003/0082665 | A1 | 5/2003 | Ingraham et al. |
| 2004/0115710 | A1 | 6/2004 | Li et al. |
| 2019/0330194 | A1 | 10/2019 | Vasbinder et al. |
| 2020/0123134 | A1 | 4/2020 | Vasbinder et al. |
| 2021/0024502 | A1 | 1/2021 | Vasbinder et al. |
| 2021/0130342 | A1 | 5/2021 | Perl et al. |

FOREIGN PATENT DOCUMENTS

| | | |
|---|---|---|
| WO | WO 2009/063244 | 5/2009 |
| WO | WO 2016/116602 | 7/2016 |
| WO | WO 2019/055966 | 7/2016 |
| WO | WO 2019/212937 | 11/2019 |
| WO | WO 2021/087018 | 5/2021 |
| WO | WO 2021/087025 | 5/2021 |

OTHER PUBLICATIONS

Couturier et al. Setting up a bioluminescence resonance energy transfer high throughput screening assay to search for protein/protein interaction inhibitors in mammalian cells. Molecular and Structural Endocrinology, 2012, col. 3, pp. 1-13. (Year: 2012).*
Kim et al, "A Quantitative Assay Reveals Ligand Specificity of the DNA Scaffold Repair Protein XRCC1 and Efficient Disassembly of Complexes of XRCC1 and the Poly(ADP-ribose) Polymerase 1 by Poly(ADP-ribose) Glycohydrolase," Journal of Biological Chemistry, Dec. 2014, 290(6):3775-3783.
Machleidt et al, "NanoBRET—A Novel BRET Platform for the Analysis of Protein-Protein Interactions," ACS Chemical Biology, Aug. 2015, 10(8): 1554-8929.
PCT International Search Report and Written Opinion in International Appln. No. PCT/US2019/029599, dated Jul. 19, 2019, 35 pages.
"Acute Leukemia," Merck Manual (Online Edition), available on or before Jul. 10, 2013, 6 pages.
Gura, "Cancer Models: Systems for identifying New Drugs Are Often Faulty," Science, 1997, 278(5340): 1041-1042.
Johnson, et al., "Relationships between drug activity in NCI preclinical in vitro and in vivo models and early clinical trials," British Journal of Cancer, 2001, 64(10):1424-1431.
Pearce, et al., "Failure modes in anticancer drug discovery and development," Cancer Drug Design and Discovery, Ed. Stephen Neidle, Chapter 18, 2008, pp. 424-435.
Simone, "Oncology: Introduction," Cecil Textbook of Medicine, 20th Edition, 1996, vol. 1, pp. 1004-1010.
Barbarulo et al, "Poly(ADP-ribose) polymerase family member 14 (PARP14) is a novel effector of the JNK2-dependent pro-survival signal in multiple myeloma,"Oncogene, 2013, 4231-4242.
Belosouva et al, "DNA is a New Target of Parp3," Scientific Reports, Mar. 2018, 8:4176, 12 pages.
Bock "Aryl hydrocarbon receptor (AHR) functions in NAD+ metabolism, myelopoiesis and obesity", Biochemical Pharmacology 163 (2019) 128-132.
Bock, "Toward elucidation of dioxin-mediated chloracne and Ah receptor functions," Biochem. Pharmacol., 2016, 112:1-5.

(Continued)

*Primary Examiner* — Shafiqul Haq
(74) *Attorney, Agent, or Firm* — Fish & Richardson P.C.

(57) ABSTRACT

The present disclosure is related to methods of identifying Poly(ADP-ribose) polymerases (PARP) inhibitors, and the methods of using PARP probes.

14 Claims, 10 Drawing Sheets
Specification includes a Sequence Listing.

(56) References Cited

OTHER PUBLICATIONS

Bolton et al., "Cell- and gene-specific regulation of primary target genes by the androgen receptor," Genes Dev., 2007, 21:2005-2017.
Caprara et al, "PARP14 Controls the Nuclear Accumulation of a Subset of Type I IFN-Inducible Proteins," The Journal of Immunology, Mar. 2018, 16 pages.
Cerami et al, "The eBio Cancer Genomics Portal: An Open Platform for Exploring Multidimensional Cancer Genomics Data," Cancer Discov. 2, 2012, 401-404.
Chen et al, "A macrodomain-linked immunosorbent assay (MLISA) for mono-ADPribosyltransferases," Analytical Biochemistiy, 2018, 543:132-139.
Cohen & Chang, "Insights into the biogenesis, function, and regulation of ADP-ribosylation," Nat. Chem. Biol., 2018, 14:236-243.
Czarnik, "Encoding strategies in combinatorial chemistry," Curr. Opin. Chem. Bio., 1997, 94(24):12378-12739.
Davis & Erlanson, "Learning from our mistakes: The 'unknown knowns' in fragment screening," Bioorganic & Medicinal Chemistiy Letters, 2013, 23:2844-2852.
Diani-Moore et al, "Aryl Hydrocarbon Receptor Activation by Dioxin Targets Phosphoenolpymvate Carboxykinase (PEPCK) for ADP-ribosylation via 2,3,7,8-Tetrachlorodibenzo-p-dioxin (TCDD)-inducible Poly(ADP-ribose) Polymerase (TiPARP)," The Journal of Biological Chemistry, 2013, 288:30:21514-21525.
Diani-Moore et al, "Identification of the Aryl Hydrocarbon Receptor Target Gene TiPARP as a Mediator of Suppression of Hepatic Gluconeogenesis by 2,3,7,8-Tetrachlorodibenzo-p-dioxin and of Nicotinamide as a Corrective Agent for This Effect," The Journal of Biological Chemistry, 2010, 285:50:38801-38810.
Dillon et al, "A FlashPlate Assay for the Identification of PARP-1 Inhibitors, "Journal of Biomolecular Screening, 2003, 3(3):347-352.
Feng et al, "Role of aryl hydrocarbon receptor in cancer," Biochim Biophys. Acta., 2013, 1836:197-210.
Gao et al., "Integrative analysis of complex cancer genomics and clinical profiles using the cBioPortal," Sci. Signal, 2013, 6:269, 19 pages.
Goode et al., "A genome-wide association study identifies susceptibility loci for ovarian cancer at 2q31 and 8q24," Nat. Genet, 2010, 42:874-879.
Hao et al, "Xenobiotics and loss of cell adhesion drive distinct transcriptional outcomes by aryl hydrocarbon receptor signaling," Mol. Pharmacol., 2012, 82:1082-1093.
Ji et al, "The Development of a Biotinylated NAD+-Applied Human Poly(ADP-Ribose) Polymerase 3 (PARP3) Enzymatic Assay," SLAS Discovery, Feb. 2018, 9 pages.
Jwa & Chang, "PARP16 is a tail-anchored endoplasmic reticulum protein required for the PERK- and IRE1 -mediated unfolded protein response," Nature Cell Biology, 14(11):1223-1230.
Kozaki et al, "Mitochondrial damage elicits a TCDD-inducible poly(ADP-ribose) polymerase-mediated antiviral response," Proc. Natl. Acad. Sci. USA, 2017, 114:2681-2686.
Lea et al, "Fluorescence polarization assays in small molecule screening," Expert Opinion on Drug Discoveiy, 6(1):17-32.
Leidecker et al, "Serine is a new target residue for endogenous ADP-ribosylation on histones," Nature Checmical Biology, Oct. 2016, 6 pages.
Ma "Induction and superinduction of 2, 3, 7, 8-tetrachlorodibenzop-dioxin-inducible poly(ADP-ribose) polymerase:Role of the aryl hydrocarbon receptor/aryl hydrocarbon receptor nuclear translocator transcription activation domains and a labile transcription repressor," Archives of Biochemistiy and Biophysics, 2002, 404:309-316.
Ma et al, "TCDD-inducible Poly(ADP-ribose) Polymerase: A Novel Response to 2,3,7,8-Tetrachlorodibenzo-p-dioxin," Biochemical and Biophysical Research Communications, 2001, 289:499-506.
MacPherson et al, "2,3,7,8-Tetrachlorodibenzo-p-dioxin poly(ADP-ribose) polymerase (TIPARP, ARTD14) is a mono-ADP-ribosyltransferase and repressor of aryl hydrocarbon receptor transactivation," Nucleic Acids Res., 2013, 41:1604-1621.

MacPherson et al., "Aryl hydrocarbon receptor repressor and TIPARP (ARTD14) use similar, but also distinct mechanisms to repress aryl hydrocarbon receptor signaling," Int. J. Mol. Sci., 2014, 15:7939-7957.
Matthews,"AHR toxicity and signaling: Role of TIPARP and ADP-ribosylation," Current Opinion in Toxicology, 2017, 2:50-57.
Ohmoto & Yachida, "Current status of poly(ADP-ribose) polymerase inhibitors and future directions," Onco. Targets Ther., 2017, 10:5195-5208.
Opitz et al, "An endogenous tumour-promoting ligand of the human aryl hydrocarbon receptor," Nature, 2011, 478:197-203.
Pan et al, "A major chromatin regulator determines resistance of tumor cells to T cell-mediated killing," Science, 2018, 359:770-775.
Papeo et al, "Insights into PARP Inhibitors' Selectivity Using Fluorescence Polarization and Surface Plasmon Resonance Binding Assays," Journal of Biomolecular Screening, 2014, 19(8):1212-1219.
PCT International Serach Report and Written Opinion in International Appln. No. PT/US2019/029582, dated Jun. 19, 2019.
Peng et al, "Small Molecule Microarray Based Discovery of PARP14 Inhibitors," Angew. Chem. Int. Ed., 2016, 55:1-7.
Roper et al, "ADP-ribosyltransferases Parp1 and Parp7 safeguard pluripotency of ES cells," Nucleic Acids Research, 2014, 42:14:8914-8927.
Schmahl et al, "PDGF signaling specificity is mediated through multiple immediate early genes," Nat. Genet., 2007, 39:52-60.
STN Search, conducted Mar. 23, 2018, 44 pages.
STN Search, conducted Mar. 5, 2018, 14 pages.
STN Search, conducted Mar. 5, 2018, 31 pages.
Stockinger et al, "The aryl hydrocarbon receptor: multitasking in the immune system," Annu. Rev. Immunol., 2014, 32:403-432.
Thorsell et al, "Structural Basis for Potency and Promiscuity in Poly(ADP-ribose) Polymerase (PARP) and Tankyrase Inhibitors," J. Med. Chem., Dec. 2016, A-J.
Tokunaga et al, "CXCL9, CXCL10, CXCL11/CXCR3 axis for immune activation—A target for novel cancer therapy," Cancer Treatment Rev 63, 2018, 40-47.
Venkannagari et al, "Activity-based assay for human mono-ADP-ribosyltransferases ARTD7/PARP15 and ARTD10/PARP10 aimed at screening and profiling inhibitors," European Journal of Pharmaceutical Sciences, 2013, 49:148-156.
Vyas et al, "A systematic analysis of the PARP protein family identifies new functions critical for cell physiology," Nat. Commun., 2013, 4:2240, 13 pages.
Vyas et al, "Family-wide analysis of poly(ADP-ribose) polymerase activity," Nature Communications, 2014, 5:4426, 13 pages.
Vyas et al, "New PARP targets for cancer therapy Nat Rev Cancer," Jun. 5, 2014, 14:502-509.
Vyas et al., "Family-wide analysis of poly(ADP-ribose) polymerase activity," 2014, Nat. Commun., 5:4426, 13 pages.
Vyas et al., "New PARP targets for cancer therapy," Nature Reviews Cancer, 2014, 8 pages.
Wahlberg et al, "Family-wide chemical profiling and structural analysis of PARP and tankyrase inhibitors," Nature Biotechnology, Mar. 2012, 30(3):283-288.
Yamada et al, "Constitutive aryl hydrocarbon receptor signaling constrains Type I interferon-mediated antiviral innate defense," Nat. Immunol., 2016, 17:687-694.
Yoneyama-Hirozane et al, "Identification of PARP14 inhibitors using novel methods for detecting auto-ribosylation," Biochemical and Biophysical Research Communications, 2017, 1-6.
Yuen et al, "A Focused DNA-encoded Chemical Library for the Discovery of Inhibitors of NAD+-dependent Enzymes," J. Am. Chem. Soc., Mar. 2019, 15 pages.
Zaffini et al, "Asthma and poly(ADP-ribose) polymerase inhibition: a new therapeutic approach," Drug Design, Development and Therapy, 2018, 12:281-2913.
Zitvogel et al., Type I interferons in anticancer immunity. Nat Rev Immun 15, 2015, 405.
PCT International Preliminary Report on Patentability in International Appln. No. PCT/US2019/029582, dated Nov. 3, 2020, 6 pages.

(56) References Cited

OTHER PUBLICATIONS

PCT International Preliminary Report on Patentability in International Appln. No. PCT/US2019/029599, dated Nov. 3, 2020, 7 pages.
PCT International Search Report and Written Opinion in International Appln. No. PCT/US2020/057819, dated Feb. 11, 2021, 8 pages.
PCT International Search Report and Written Opinion in International Appln. No. PCT/US2020/057831, dated Feb. 11, 2021, 8 pages.
STN Search, conducted Oct. 15, 2019, 5 pages.
STN Search, conducted Oct. 15, 2019, 8 pages.

* cited by examiner

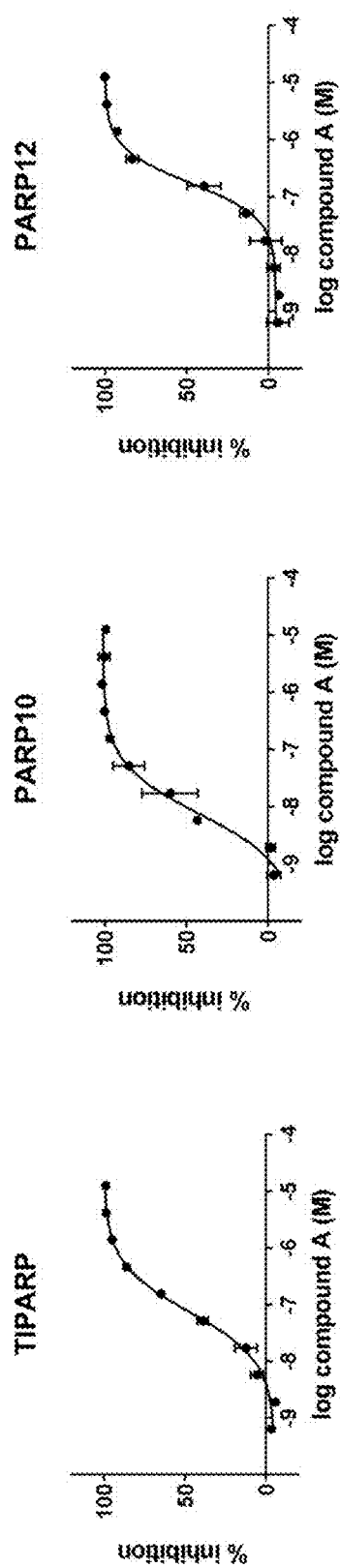
FIG. 4A
FIG. 4B
FIG. 4C
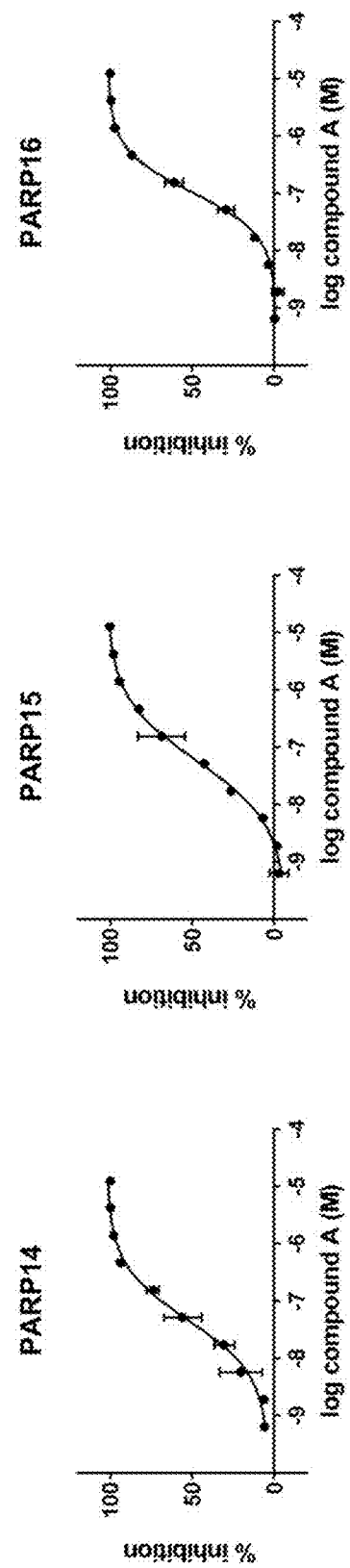
FIG. 4D
FIG. 4E
FIG. 4F

```
TIPARP NP_056323.2 (SEQ ID NO: 1)
    1 memettepep dcvvqpspsp ddfscqmrls ekitplktcf kkkdqkrlgt gtlrslrpil
   61 ntllesqsld gvfrsrnqst denslhepmm kkameinssc ppaennmavl ipdrtnvgdq
  121 ipeahpstea pervvpiqdh sfpsetlsqt vadstpahfq tdllhpvssd vptspdcldk
  181 vidyvpgifq ensftiqyil dtsdklstel fqdkseeasl dlvfelvnql qyhthqengi
  241 eicmdflqgt ciygrdclkh htvlpyhwqi krtttqkwqs vfndsqehle rfycnpendr
  301 mrmkygqgef wadlnamnvy ettefdqlrr lstppssnvn siyhtvwkff crdhfgwrey
  361 pesvirliee ansrglkevr fmmwnnhyil hnsffrreik rrplfrscfi llpylqtlgg
  421 vptqappple atsssqiicp dgvtsanfyp etwvymhpsq dfiqvpvsae dksyriiynl
  481 fhktvpefky rilqilrvqn qflwekykrk keymnrkmfg rdriinerhl fhgtsqdvvd
  541 gickhnfdpr vcgkhatmfg qgsyfakkas yshnfskkss kgvhfmflak vltgrytmgs
  601 hgmrrpppvn pgsvtsdlyd scvdnffepq ifvifnddqs ypyfviqyee vsntvsi PARP10 NP_116178.2 (SEQ ID NO: 2)
    1 mvamaeaeaq vavevrglpp avpdelltly fenrrrsggg pvlswqrlgc ggvltfrepa
   61 daervlaqad helhqaqlsl rpapprapar lllqglppgt tpqrleqhvq allrasglpv
  121 qpccalaspr pdralvqlpk plseadvrvl eeqaqnlgle gtlvslarvp qaravrvvgd
  181 qasvdlllle lylenerrsg ggplediqrl pqplqtvasf qqwqvaervl qqehrlqgse
  241 lslvphydil epeelaents ggdhpstqgp ratkhallrt gglvtalqga gtvtmqsgee
  301 pgqsgaslrt gpmvqgrgim ttgsgqepgq sgtslrtgpm gslqqaeqvs smpmgslehe
  361 glvslrpvgl qeqegpmslg pvgsagpvet skgllgqegl veiamdspeq eglvqpmeit
  421 mgslekagpv spgcvklagq eglvemvllm epgamrflql yhedllaglg dvallplegp
  481 dmtgfrlcga qascqaaeef lrsllgsisc hvlclehpgs arfllgpegq hllqgleaqf
  541 qcvfgterla tatldtglee vdptealpvl pgnahtlwtp dstggdqedv sleevrella
  601 tleqldldge dwlpreleee gpqeqpeeev tpgheeeepv apstvaprwl eeeaalqlal
  661 hrslepqgqv aeqeeaaalr qaltlslleq ppleaeeppd ggtdgkaqlv vhsafeqdve
  721 eldralraal evhvqeetvg pwrrtlpael rarlerchqv svalrqdcti lrgfgahpar
  781 aarhlvalla gpwdqslafp laasgptlag qtlkqpwnnl erlaentgef qevvrafydt
  841 ldaarssirv vrvervshpl lqqqyelyre rllqrcerrp veqvlyhgtt apavpdicah
  901 gfnrsfcgrn atvygkgvyf arraslsvqd rysppnadgh kavfvarvlt gdygqgrrgl
  961 rapplrgpgh vllrydsavd cicqpsifvi fhdtqalpth litcehvpra spddpsglpg
 1021 rspdt PARP12 NP_073587.1 (SEQ ID NO: 3)
    1 maqagvvgev tqvlcaagga lelpelrrrl rmglsadale rllrqrgrfv vavraggaaa
   61 apervvlaas plrlcrahqg skpgcvglca qlhlcrfmvy gackflragk ncrnshsltt
  121 ehnlsvlrth gvdhlsynel cqllfqndpw llpeicqhyn kgdgphgsca fqkqciklhi
  181 cqyflqgeck fgtsckrshd fsnsenlekl eklgmssdlv srlptiyrna hdiknkssap
  241 srvpplfvpq gtserkdssg svspntlsqe egdqiclyhi rkscsfqdkc hrvhfhlpyr
  301 wqfldrqkwe dldnmeliee aycnpkieri lcsesastfh shclnfnamt ygatqarrls
  361 tassvtkpph filttdwiwy wsdefgswqe ygrqgtvhpv ttvsssdvek aylayctpgs
  421 dgqaatlkfq agkhnyeldf kafvqknlvy gttkkvcrrp kyvspqdvtt mqtcntkfpg
  481 pksipdywds salpdpgfqk itlszsseey qkvwnlfnrt lpfyfvqkie rvqnlalwev
  541 yqwqkgqmqk qnggkavder qlfhgtsaif vdaicqqnfd wrvcgvhgts ygkgsyfard
  601 aayshhysks dtqthtmfla rvlvgefvrg nasfvrppak egwsnafyds cvnsvsdpsi
  661 fvifekhqvy peyviqytts skpsvtpsil lalgslfssr q PARP14 NP_060024.2 (SEQ ID NO: 4)
    1 mavpgsfpll vegswgpdpp knlntklqmy fqspkrsggg ecevrqdprs psrflvffyp
   61 edvrqkvler knhelvwqgk gtfkltvqlp atpdeidhvf eeelltkesk tkedvkepdv
  121 seeldtklpl dgglgdkmedi peecenissl vafenlkanv tdimlillve nisqlsnddf
```

FIG. 6A

```
 181 qveiirdfdv avvtfqkhid tirfvddctk hhsikqlqls prllevtnti rvenlppgad
 241 dyslkiffen pyngggrvan veyfpeessa lieffdrkvl dtimatkldf nkmplsvfpy
 301 yaslgtalyg kekplikipa pfeesldlpl wkflqkknhl ieeindemrr chceltwsql
 361 sgkvtirpaa tlvnegrpri ktwqadtstt lssirskykv npikvdptmw dtikndvkdd
 421 riliefdtlk emvilagkse dvqsievqvr eliesttqki kreeqslkek miispgryfl
 481 lchsslldhl ltecpeieic ydrvtqhlcl kgpsadvyka kceiqekvyt maqkniqvsp
 541 eifqflqqvn wkefskclfi aqkilalyel eqttvlltsc sseealleaek qmlsalnykr
 601 ievenkevlh gkkwkglthn likkqnsspn tviineltse ttaeviitgc vkevnetykl
 661 lfnfveqnmk ierlvevkps lvidylktek klfwpkikkv nvqvsfnpen kqkgilltgs
 721 ktevlkavdi vkqvwdsvcv ksvhtdkpga kqffqdkarf yqseikrlfg cyielqenev
 781 mkeggspaqq kcfsrtvlap gvvlivqqgd larlpvdvvv nasnedlkhy gglaaalska
 841 agpelqadcd qivkregrll pqnatiskag klpyhhviha vgprwsgyea prcvyllrra
 901 vqlslclaek ykyrsiaipa issqvfgfpl grcvetivsa ikenfqfkkd ghclkeiylv
 961 dvsektveaf aeavktvfka tlpdtaappq lppaaagpgk tswekgslvs pqglqmllvk
1021 egvqnaktdv vvnsvpldlv lsrgplsksl lekagpelqe eldtvgqgva vsmqtvlkts
1081 swnldcryvl hvvapewrng stsslkimed iirecmeite slslksiafp aigtgnlgfp
1141 knifaeliis evfkfssknq lktlqevhfl lhpsdheniq afsdefarra ngnlvsdkip
1201 kakdtqgfyg tvsspdsgvy emkigsiifq vasqditkee advivnstsn sfnlkaqvsk
1261 ailecaggnv erecsqqagq rkndyiitgg qflrckniih viggndvkss vssvlqecek
1321 knyssiclpa igtgnakqhp dkvaeaiida iedfvqkgsa qsvkkvkvvi flpqvldvfy
1381 anmkkregtq lssqqsvmsk lasflqfskq spqkknhlvl ekktesatfr vcgenvtcve
1441 yaiswlqdli ekeqcpytse decikdfdek eyqelnelqk klninisldh krplikvlgi
1501 srdvmqarde ieamikrvrl akeqesradc isefiewqyn dnntshcfnk mtnlkledar
1561 rekkktvdvk inhrhytvnl ntytatdtkg hslsvqrltk skvdipahws dmkqqnfcvv
1621 ellpsdpeyn tvaskfnqtc shfriekier iqnpdlwnsy qakkktmdak ngqtmnekql
1681 fhqtdaqsvp hvnrngfnrs yagknavayq kqtyfavnan ysandtysrp dangrkhvyy
1741 vrvltgiyth gnhslivpps knpqnptdly dtvtdnvhhp slfvafydyq aypeylitfr
1801 k PARP15 NP_689828.1 (SEQ ID NO: 5)
   1 mlqriglifl hnivvvsncf yfqafldeft nwsrinpnka ripmagdtqg vvgtvskpcf
  61 tayemkiqai tfqvatgdia teqvdvivns tartfnrksg vsraillegag qavesecavl
 121 aaqphrdfii tpggclkcki iihvpggkdv rktvtsvlee ceqrkytsvs lpaigtgnag
 181 knpitvadni idaivdfssq hstpslktvk vvifqpelln ifydsmkkrd lsaslnfqst
 241 fsmttcnlpe hwtdmnhqlf cmvqlepgqs eyntikdkft rtcssyaiek ieriqnaflw
 301 qsyqvkkrqm dikndhknne rllfhqtdad svpyvnqhgf nrscagknav sygkgtyfav
 361 dasysakdty skpdsngrkh myvvrvltgv ftkgraglvt pppknphnpt dlfdsvtnnt
 421 rspklfvvff dnqaypeyli tfta PARP16 NP_060321.3 (SEQ ID NO: 6)
   1 mqpsgwaaar eaagrdmlaa dlrcslfasa lqsykrdsvl rpfpasyarg dckdfealla
  61 dasklpnlke llqssgdnhk rawdlvswil sskvltihsa gkaefekiqk ltgaphtpvp
 121 apdflfeiey fdpanakfye tkqerdliya fhqsrlenfh siihnglhch lnktslfqeg
 181 tyltsdlsla liysphqhgw qhsllgpils cvavcevidh pdvkcqtkkk dskeidrrra
 241 rikhseggdi ppkyfvvtnn qllrvkyllv ysqkppksra ssqlswfssh wftvmislyl
 301 llllivsvin ssafqhfwnr akr PARP1 NP_001609.2 (SEQ ID NO: 13)
   1 maessdklyr veyaksgras ckkcsesipk dslrmaimvq spmfdgkvph wyhfscfwkv
  61 ghsirhpdve vdgfselrwd dqqkvkktae aggvtgkgqd gigskaektl gdfaaeyaks
 121 nrstckgcme kiekgqvrls kkmvdpekpq lgmidrwyhp gcfvknreel gfrpeysasq
 181 lkgfsllate dkealkkqlp gvkseqkrkg devdgvdeva kkskkekdk dsklekalka
 241 qndliwnikd elkkvcstnd lkellifnkq qvpsgesail drvadgmvfg allpceecsg
 301 qlvfksdayy ctgdvtawtk cmvktqtpnr kewvtpkefr eisylkklkv kkqdrifppe
```

FIG. 6B

```
361 tsasvaatpp pstasapaav nssasadkpl snmkiltlgk lsrnkdevka mieklggklt
421 gtankaslci stkkevekmn kkmeevkean irvvsedflq dvsastkslq elflahilsp
481 wqaevkaepv evvaprgksg aalskkskgq vkeeqinkse krmkltlkgg aavdpdsgle
541 hsahvlekgg kvfsatlglv divkgtnsyy klqlleddke nrywifrswg rvgtvigsnk
601 leqmpskeda iehfmklyee ktqnawhskn ftkypkkfyp leidygqdee avkkltvnpg
661 tksklpkpvq dlikmifdve amkkamveye idlqkmplgk lskrqiqaay silsevqqav
721 sqgssdsqil dlsnrfytli phdfgmkkpp llnnadsvqa kvemldnlld ievaysllrg
781 gsddsskdpi dvnyeklktd ikvvdrdsee aeiirkyvkn thatthnayd levidifkie
841 regecqrykp fkqlhnrrll whqsrttnfa gilsqglria ppeapvtqym fgkgiyfadm
901 vsksanycht sqgdpiglil lgevalqnmy elkhashisk lpkgkhsvkg lgkttpdpsa
961 nisldgvdvp lgtgissgvn dtsllyneyi vydiaqvnlk yllklkfnfk tslw PARP2 NP_005475.2 (SEQ ID NO: 14)
    1 maarrrrstg ggraralnes krvnnqntap edsspakktr rcqrqeskkm pvaggkankd
   61 rtedkqdgmp grswaskrvs esvkalllkq kapvdpecta kvgkahvyce qndvydvmln
  121 qtnlqfnnnk yyliqilledd aqrnfsvwmr wgrvgkmgqh slvacsgnln kakeifqkkf
  181 ldktknnwed rekfekvpgk ydmlqmdyat ntqdeeetkk eeslksplkp esqldlrvqe
  241 liklicnvqa meemmmemky ntkkaplgkl tvaqikagyq slkkiedcir agqhqralme
  301 acnefytrip hdfglrtppl irtqkelsek iqllealgdi eiaiklvkte lqspehpldq
  361 hyrnlhcalr pldhesyefk visqylqsth apthsdytmt lldlfevekd gekeafredl
  421 hnrmllwhgs rmsnwvqils hglriappea pitgymfgkg iyfadmssks anycfasrlk
  481 ntglllllsev algqcnelle anpkaegllq qkhstkglgk mapssahfvt lngstvplgp
  541 asdtgilnpd gytlnyneyi vynpnqvrmr yllkvqfnfl qlw PARP3 NP_001003931.3 (SEQ ID NO: 15)
    1 mslliflamap kpkpwvqteg pekkkgrqag reedpfrsta ealkaipaek riirvdptcp
   61 lssnpgtqvy edynctlnqt niennnnkfy iiqllqdsnr ffftcwnrwgr vgevgqskin
  121 hftrledakk dfekkfrekt knnwaerdhf vshpgkytli evqaedeaqe avvkvdrgpv
  181 rtvtkrvgpc sldpatqkli tnifskemfk ntmalmdldv kkmplgklsk qqiargfeal
  241 ealeealkgp tdgqsleel sshfytviph nfghsqpppi nspellqakk dmllvladie
  301 laqalqavse qektveevph pldrdyqllk cqlqllds qa peykviqtyl eqtgsnhrcp
  361 tlqhiwkvnq egeedrfqah sklgnrkllw hgtnmavvaa iltsglrimp hsggrvgkgi
  421 yfasensksa gyvigmkcga hhvgymflqe valqrehhin tdnpslkspp pqfdsviarg
  481 htepdptqdt eleldgqqvv vpqgqpvpcp efssstfsqs eyliyqesqc lryllevhl PARP4 NP_006428.2 (SEQ ID NO: 16)
    1 mvmgifanci fclkvkylpq qqkkklqtdi kenggkfsfs lnpqcthiil dnadvlsqyq
   61 lnsiqknhvh ianpdfiwks irekrlldvk nydpykpldi tpppdqkass sevkteglcp
  121 dsateeedtv eltefgmqnv eiphlpqdfe vakyntlekv qmeggqeavv velqcsrdsr
  181 dcpflisshf llddgmetrr qfaikktsed aseyfenyie elkkqgfllr ehftpeatql
  241 aseqlqalll eevmnsstls qevsdlvemi waealghleh mllkpvnris lndvskaegi
  301 lllvkaalkn qetaeqlqkm mtefyrliph kgtmpkevnl gllakkadlc qlirdmvnvc
  361 etnlskpnpp slakyralrc kiehveqnte eflrvrkevl qnhhsksspvd vlqifrvgrv
  421 netteflskl gnvrpllhgs pvqnivqilc rglllpkvve drgvqrtdvg nlgsgiyfsd
  481 slststsikysh pqetdgtrll licdvalgkc mdlhekdfsl teappgydsv hqvsqtasvt
  541 tdfeddefvv yktnqvkmky iikfsmpgdq ikdfhpsdht eleeyrpefs nfskvedyql
  601 pdaktssstk aglqdasqnl vpledvhikg riidtvaqvi vfqtytnksh vpieakyifp
  661 lddkaavcgf eafingkhiv geikekeeaq qeyleavtqg hgaylmsqda pdvftvsvgn
  721 lppkakvlik ityitelsil gtvgvffmpa tvapwqqdka lnenlqdtve kicikeigtk
  781 qsfsoltmsie mpyviefifs dthelkqkrt dckavistme qssldssqfs lhiglsaayl
  841 prmwvekhpe keseacmlvf qpdldvdlpd laseseviic ldcsssmeqv tflqakqial
  901 halslvqekq kvniiqfgtg ykelfsypkh itsntmaaef imsatptmqn tdfwktlryl
  961 sllypargsr nillvsdghl qdesltlqlv krsrphtrlf acgigstanr hvlrilsqcg
 1021 agvfeyfnak skhswrkqie dqmtrlcsps chsvsvkwqq lnpdvpealq apaqvpslfl
 1081 ndrllvygfi phctqatlca liqekefrtm vsttelqktt gtmihklaar alirdyedgi
 1141 lhenetshem kkqtlkslii klskenslit qftsfvavek rdenespfpd ipkvseliak
 1201 edvdflpyms wqgepqeavr nqsllassew pelrlskrkh rkipfskrkm elsqpevsed
```

FIG. 6C

```
1261 feedglgvlp aftsnlergg vekildlswt esckptatep lfkkvspwet stssffpila
1321 pavgsylppt arahspasls fasyrqvasf gsaapprqfd asqfsqqpvp gtcadwipqs
1381 ascptqppqn ppsspycgiv fsqsslssaq saplqhpggf ttrpsaqtfp eldspqlhfs
1441 lptdpdpirg fqsyhpsass pfhfqpsaas ltanlrlpma salpealcsq srttpvdlcl
1501 leesvgsleg srcpvfafqs sdtesdelse vlqdscflqi kcdtkddsil cflevkeede
1561 ivciqhwqda vpwtellslq tedqfwkltp elglilnlnt nglhsflkqk giqslgvkgr
1621 eclldliatm lvlqfirtrl ekegivfksl mkmddasisr nipwafeaik qasewvrrte
1681 gqypsicprl elgndwdsat kqliglqpis tvsplhrvlh ysqg
```

PARP5a NP_003738.2 (SEQ ID NO: 17)

```
   1 maasrrsqhh hhhhqqqlqp apgasapppp ppplspgla pgttpaspta sglapfaspr
  61 hglalpegdg srdppdrprs pdpvdgtscc sttstictva aapvvpavst ssaagvapnp
 121 agsgsnnsps ssssptssss sspsspgssl aespeaagvs staplqpgaa gpgtgvpavs
 191 qalrelleac rngdvsrvkr lvdaanvnak dmagrksspl hfaagfgrkd vvehllqmga
 241 nvharddggl iplhnacsfg haevvslllc qgadpnardn wnytplheaa ikgkidvciv
 301 llqhgadpni rntdgksald ladpsakavl tgeykkdell eaarsgneek lmalltplnv
 361 nchasdgrks tplhlaagyn rvrivqlllq hgadvhakdk gglvplhnac syghyevtel
 421 llkhgacvna mdlwqftplh eaaasknrvev cslllshgad ptlvnchgks avdmaptpel
 481 rerltyefkg hsllqaarea dlakvkktla leiinfkqpq shetalhcav aslhpkrkqv
 541 telllrkgan vneknkdfmt plhvaaerah ndvmevlhkh qakmnaldtl gqtalhraal
 601 aghlqtcrll lsygsdpsii slqgftaaqm gneavqqils estpirtsdv dyrlleaska
 661 gdletvkqlc ssqnvncrdl egrhstplhf aagynrvsvv eyllhhgadv hakdkgglvp
 721 lhnacsyghy evaellvrhg asvnvadlwk ftplheaaak gkyeicklll khgadptkkn
 781 rdgntpldlv kegdtdiqdl lrgdaallda akkgclarvq klctpeninc rdtqgrnstp
 841 lhlaagynnl evaeyllehg advnaqdkgg liplhnaasy ghvdiaalli kyntcvnatd
 901 kwaftplhea aqkgrtqlca lllahgadpt mknqegqtpl dlataddira llidamppea
 961 lptcfkpqat vvsaslispa stpsclsaas sidnltgpla elavggasna gdgaagterk
1021 egevagldmn isqflkslgl ehlrdifete qitldvladm gheelkeigi nayghrhkli
1081 kgverllgqq qgtnpyltfh cvnqgtilld lapedkeyqs veeemqstir ehrdggnagg
1141 ifnrynviri qkvvnkklre rfchrqkevs eenhnhhner mlfhgspfin aiihkgfder
1201 hayiggmfga giyfaenssk snqyvygigg gtgcpthkdr scyichrqml fcrvtlgksf
1261 lqfstmkmah appghhsvig rpsvnqlaya eyviyrgeqa ypeylityqi mkpeapsqta
1321 taaeqkt
```

PARP5b NP_079511.1 (SEQ ID NO: 18)

```
   1 msgrrcaggg aacasaaaea vepaarelfe acrngdverv krlvtpekvn srdtagrkst
  61 plhfaagfgr kdvveyllqn ganvqarddg gliplhnacs fghaevvnll lrhgadpnar
 121 dnwnytplhe aaikgkidvc ivllqhgaep tirntdgrta ldladpsaka vltgeykkde
 181 llesarsgne ekmmalltpl nvnchasdgr kstplhlaag ynrvkivqll lqhgadvhak
 241 dkgdlvplhn acsyghyevt ellvkhgacv namdlwqftp lheaaasknrv evcslllsyg
 301 adptllnchn ksaidlaptp qlkerlayef kqhsllqaar eadvtrikkh lslemvnfkh
 361 pqthetalhc aaaspypkrk qicelllrkg aninektkef ltplhvasek ahndvvevvv
 421 kheakvnald nlgqtslhra aycghlqtcr lllsygcdpn iislqqftal qmgnenvqql
 481 lqegislgns eadrqlleaa kagdvetvkk lctvqsvncr diegrqstpl hfaagynrvs
 541 vveyllqhga dvhakdkggl vplhnacsyg hyevaellvk hgavvnvadl wkftplheaa
 601 akgkyeickl llqhgadptk knrdgntpld lvkdgdtdiq dllrgdaall daakkgclar
 661 vkklsspdnv ncrdtqgrhs tplhlaagyn nlevaeyllq hgadvnaqdk ggliplhnaa
 721 syghvdvaal likynacvna tdkwaftplh eaaqkgrtql calllahgad ptlknqegqt
 781 pldlvsaddv salltaampp salpscykpq vlnqvrspga tadalssgps spsslsaass
 841 ldnlsgsfse lssvvsssgt egasslekke vpgvdfsitq fvrnlglehl mdifereqit
 901 ldvlvemghk elkeiginay ghrhklikgv erllsgqqgl npyltlntsg agtilidlsp
 961 ddkefqsvee emqstvrehr dgghaqgifn rynilkiqkv cnkklweryt hrrkevseen
1021 hnhanermlf hqspfvnaii hkgfderhay iggmfgagiy faensssksnq yvygigggtg
1081 cpvhkdrscy ichrqllfcr vtlgksflqf samkmahspp ghhsvtqrps vnglalaeyv
1141 iyrgeqaype ylityqimrp egmvdq
```

FIG. 6D

```
PARP6 NP_001310451.1 (SEQ ID NO: 19)
    1 mdikgqfwnd ddseqdnese eflygvqgsc aadlyrhpql dadieavkei ysensvsire
   61 ygtiddvdid lhinisflde evstawkvlr tepivlrlrf slsqyldgpe psievfqpsn
  121 kegfglglql kkilgmftsq qwkhlsndfl ktqqekrhsw fkasgtikkf raglsifspi
  181 pkspsfpiiq dsmlkgklgv pelrvgrlmn rsisctmknp kvevfgypps pqagllcpqh
  241 vglppparts plvsghckni ptleyqflvq imkyaeqrip tlneycvvcd eqhvfqngsm
  301 lkpavctrel cvfsfytlgv msgaaeevat qaevvdllva mcraalespr ksiifepyps
  361 vvdptdpktl afnpkkknye rlqkaldsvm siremtqgsy leikkqmdkl dplahpllqw
  421 iissnrshiv klplsrlkfm htshqfllls sppakearfr takklyqstf afhgshienw
  481 hsilrnglvn asytklqlhg aaygkgiyls pissisfgys gmgkgqhrmp skdelvqryn
  541 rmntipqtrs iqsrflqsrn lncialcevi tskdlqkhgn iwvcpvsdhv ctrfffvyed
  601 gqvgdanint qdpkiqkeim rvigtqvytn PARP8 AAH37306.1 (SEQ ID NO: 20)
    1 mqtfvtqqwk qskeksnclh nkklsekkvk splhlfstlr rspsypppgc qkskskllkse
   61 qdgiskthkl lrrtcsstvk tddvcvtksh rtfgrslssd praeqamtai kshkllnrpc
  121 paavkseecl tlkshrlltr scsgdprceh ntnlkphkll srsyssnlrm eelyglknhk
  181 llsksyssap kssktelfke pnaegrrlsl tsgligiltp sssssqlap nqakcipvrd
  241 rgflvqtief aeqripvlne ycvvcdephv fqngpmlrpt vcerelcvfa fqtlgvmnea
  301 adeiatgaqk knydrvmkal dsitsiremt qapyleikkq mdkqdplahp llqwvissnr
  361 shivklpvnr qlkfmhtphq fllissppak esnfraakkl fgstfafhqs hienwhsilr
  421 nglvvasntr lqlhgamygs giylspmssi sfgysgmnkk qkvsakdepa ssskssntsq
  481 sqkkrtaipi pakp PARP9 AAH39580.1 (SEQ ID NO: 21)
    1 mdfsmvaqaa aynekseetga lgenyswqip inhndfkilk nnerqlcevl qnkfgcistl
   61 vspvqeqnsk slqvfrkmlt prielsvwkd dltthavdav vnaaanedllh ggglalalvk
  121 aggfeiqees kqfvarygkv sageiavtga grlpckqiih avgprwmewd kqgctgklqr
  181 aivsilnyvi yknthiktva ipalssqifq fplnlctkti vetirvslqg kpmmsnlkei
  241 hlvsnedptv aafkaasefi lgkselgqet tpsfnamvvn nltlqivqgh iewqtadviv
  301 nsvnphditv gpvaksilqq agvemksefl atkakqfqrs qlvlvtkgfn lfckyiyhvl
  361 whsefpkpqi lkhamkecle kcieqnitsi sfpalgtgnm eikketaaei lfdevltfak
  421 dhvkhqltvk fvifptdlei ykafssemak rskmlslnny svpqstreek rengleearsp
  481 ainlmgfnve emyeahawiq rilslqnhhi iennhilylg rkehdilsql qktssvsite
  541 iispgrtele iegaradlie vvmniedmlc kvqeemarkk erglwrslgq wtiqqqktqd
  601 emkeniiflk cpvpptqell dqkkqfekcg lqvlkvekid nevlmaafqr kkkmmeeklh
  661 rqpvshrlfq qvpyqfcnvv crvgfqrmys tpcdpkygag iyftknlknl aekakkisaa
  721 dkliyvfeae vltgffcqgh plnivppls pgaidghdsv vdnvsspetf vifsqmqaip
  781 qylwtctqey vqsqdyssgp mrpfaqhpwr gfasgspvd PARP11 Q9NR21.2 (SEQ ID NO: 22)
    1 mweanpemfh kaeelfsktt nnevddmdts dtqwqwfyla ecgkwhmfqp dtnsqcsvss
   61 ediekefktn pcgsisftts kfsykidfae mkqmnlttgk qrlikrapfs isafsyicen
  121 eaipmpphwe nvntqvpyql iplhnqthey nevanlfgkt mdrnrikriq riqnldlwef
  181 fcrkkaqlkk krgvpqineq mlfhgtssef veaicihnfd wringihgav fqkqtyfard
  241 aayssrfckd dikhgntfqi hgvslqqrhl frtyksmfla rvligdying dskymrppsk
  301 dgsyvnlyds cvddtwnpki fvvfdanqiy peylidfh PARP13 NP_064504.2 (SEQ ID NO: 23)
    1 madpevccfi tkilcahggq maldallqei alsepqlcev lqvagpdrfv vletggeagi
   61 trsvvattra rvcrrkycqr pcdnlhlckl nllgrcnysq sernlckysh evlseeenfkv
  121 lknhelsqln keelavlllq sdpffmpeic ksykgegrqq icnqqppcsr lhicdhftrg
  181 ncrfpnclrs hnlmdrkvla imrehglnpd vvqniqdicn skhmqknppg prapsshrrn
  241 mayrarsksr drffqgsqef lasasasaer sctpspsdqis hrasledapv ddltrkftyl
  301 qsqdrarpps gsskatdlgg tsqagtsqrf lengsqedll hgnpgstyla snstsapnwk
  361 sltswtndqg arrktvfspt lpaarsslqs lqtpeavttr kgtgllssdy riingksqtq
  421 diqpgplfnn nadgvatdit strslnykst ssghreissp riqdagpasr dvqatgriad
```

FIG. 6E

```
481 dadprvalvn dslsdvtstt ssrvddhdse eicldhlckg cplngscskv hfhlpyrwqm
541 ligktwtdfe hmetiekgyc npgihlcsvg sytinfrvms cdsfpirrls tpssvtkpan
601 svfttkwiwy wknesgtwiq ygeekdkrkn snvdssyles lyqscprgvv pfqaqsrnye
661 lsfqgmiqtn iasktqkdvi rrptfvpqwy vqqmkrgpdh qpaktssvsl tatfrpqedf
721 cflsskkykl seihhlhpey vrvsehfkas mknfkiekik kienselldk ftwkksqmke
781 eqkllfyats rayvesicsn nfdsflheth enkygkgiyf akdaiyshkn cpydaknvvm
841 fvaqvlvgkf tegnitytsp ppqfdscvdt rsnpsvfvif qkdqvypqyv ieytedkacv
901 is
```

FIG. 6F

SEQUENCE LISTING

<160> NUMBER OF SEQ ID NOS: 23

<210> SEQ ID NO 1
<211> LENGTH: 657
<212> TYPE: PRT
<213> ORGANISM: Homo sapiens

<400> SEQUENCE: 1

```
Met Glu Met Glu Thr Thr Glu Pro Glu Pro Asp Cys Val Val Gln Pro
1               5                   10                  15

Pro Ser Pro Pro Asp Asp Phe Ser Cys Gln Met Arg Leu Ser Glu Lys
                20                  25                  30

Ile Thr Pro Leu Lys Thr Cys Phe Lys Lys Lys Asp Gln Lys Arg Leu
            35                  40                  45

Gly Thr Gly Thr Leu Arg Ser Leu Arg Pro Ile Leu Asn Thr Leu Leu
        50                  55                  60

Glu Ser Gly Ser Leu Asp Gly Val Phe Arg Ser Arg Asn Gln Ser Thr
65                  70                  75                  80

Asp Glu Asn Ser Leu His Glu Pro Met Met Lys Lys Ala Met Glu Ile
                85                  90                  95

Asn Ser Ser Cys Pro Pro Ala Glu Asn Asn Met Ser Val Leu Ile Pro
                100                 105                 110

Asp Arg Thr Asn Val Gly Asp Gln Ile Pro Glu Ala His Pro Ser Thr
            115                 120                 125

Glu Ala Pro Glu Arg Val Val Pro Ile Gln Asp His Ser Phe Pro Ser
        130                 135                 140

Glu Thr Leu Ser Gly Thr Val Ala Asp Ser Thr Pro Ala His Phe Gln
145                 150                 155                 160

Thr Asp Leu Leu His Pro Val Ser Ser Asp Val Pro Thr Ser Pro Asp
                165                 170                 175

Cys Leu Asp Lys Val Ile Asp Tyr Val Pro Gly Ile Phe Gln Glu Asn
                180                 185                 190

Ser Phe Thr Ile Gln Tyr Ile Leu Asp Thr Ser Asp Lys Leu Ser Thr
            195                 200                 205

Glu Leu Phe Gln Asp Lys Ser Glu Glu Ala Ser Leu Asp Leu Val Phe
        210                 215                 220

Glu Leu Val Asn Gln Leu Gln Tyr His Thr His Gln Glu Asn Gly Ile
225                 230                 235                 240
```

```
Glu Ile Cys Met Asp Phe Leu Gln Gly Thr Cys Ile Tyr Gly Arg Asp
                245                 250                 255

Cys Leu Lys His His Thr Val Leu Pro Tyr His Trp Gln Ile Lys Arg
            260                 265                 270

Thr Thr Thr Gln Lys Trp Gln Ser Val Phe Asn Asp Ser Gln Glu His
        275                 280                 285

Leu Glu Arg Phe Tyr Cys Asn Pro Glu Asn Asp Arg Met Arg Met Lys
    290                 295                 300

Tyr Gly Gly Gln Glu Phe Trp Ala Asp Leu Asn Ala Met Asn Val Tyr
305                 310                 315                 320

Glu Thr Thr Glu Phe Asp Gln Leu Arg Arg Leu Ser Thr Pro Pro Ser
                325                 330                 335

Ser Asn Val Asn Ser Ile Tyr Thr Val Trp Lys Phe Phe Cys Arg
            340                 345                 350

Asp His Phe Gly Trp Arg Glu Tyr Pro Glu Ser Val Ile Arg Leu Ile
            355                 360                 365

Glu Glu Ala Asn Ser Arg Gly Leu Lys Glu Val Arg Phe Met Met Trp
    370                 375                 380

Asn Asn His Tyr Ile Leu His Asn Ser Phe Phe Arg Arg Glu Ile Lys
385                 390                 395                 400

Arg Arg Pro Leu Phe Arg Ser Cys Phe Ile Leu Leu Pro Tyr Leu Gln
                405                 410                 415

Thr Leu Gly Gly Val Pro Thr Gln Ala Pro Pro Leu Glu Ala Thr
            420                 425                 430

Ser Ser Ser Gln Ile Ile Cys Pro Asp Gly Val Thr Ser Ala Asn Phe
    435                 440                 445

Tyr Pro Glu Thr Trp Val Tyr Met His Pro Ser Gln Asp Phe Ile Gln
450                 455                 460

Val Pro Val Ser Ala Glu Asp Lys Ser Tyr Arg Ile Ile Tyr Asn Leu
465                 470                 475                 480

Phe His Lys Thr Val Pro Glu Phe Lys Tyr Arg Ile Leu Gln Ile Leu
            485                 490                 495

Arg Val Gln Asn Gln Phe Leu Trp Glu Lys Tyr Lys Arg Lys Lys Glu
            500                 505                 510

Tyr Met Asn Arg Lys Met Phe Gly Arg Asp Arg Ile Ile Asn Glu Arg
            515                 520                 525

His Leu Phe His Gly Thr Ser Gln Asp Val Val Asp Gly Ile Cys Lys
    530                 535                 540

His Asn Phe Asp Pro Arg Val Cys Gly Lys His Ala Thr Met Phe Gly
545                 550                 555                 560

Gln Gly Ser Tyr Phe Ala Lys Lys Ala Ser Tyr Ser His Asn Phe Ser
                565                 570                 575

Lys Lys Ser Ser Lys Gly Val His Phe Met Phe Leu Ala Lys Val Leu
            580                 585                 590

Thr Gly Arg Tyr Thr Met Gly Ser His Gly Met Arg Arg Pro Pro
        595                 600                 605

Val Asn Pro Gly Ser Val Thr Ser Asp Leu Tyr Asp Ser Cys Val Asp
    610                 615                 620

Asn Phe Phe Glu Pro Gln Ile Phe Val Ile Phe Asn Asp Asp Gln Ser
625                 630                 635                 640

Tyr Pro Tyr Phe Val Ile Gln Tyr Glu Glu Val Ser Asn Thr Val Ser
                645                 650                 655
```

-continued

Ile

```
<210> SEQ ID NO 2
<211> LENGTH: 1025
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Val | Ala | Met | Ala | Glu | Ala | Glu | Ala | Gly | Val | Ala | Glu | Val | Arg | |
| 1 | | | | 5 | | | | | 10 | | | | | 15 | |
| Gly | Leu | Pro | Pro | Ala | Val | Pro | Asp | Glu | Leu | Leu | Thr | Leu | Tyr | Phe | Glu |
| | | | 20 | | | | | 25 | | | | | 30 | | |
| Asn | Arg | Arg | Arg | Ser | Gly | Gly | Pro | Val | Leu | Ser | Trp | Gln | Arg | Leu | |
| | | 35 | | | | | 40 | | | | | 45 | | | |
| Gly | Cys | Gly | Gly | Val | Leu | Thr | Phe | Arg | Glu | Pro | Ala | Asp | Ala | Glu | Arg |
| | 50 | | | | | 55 | | | | | 60 | | | | |
| Val | Leu | Ala | Gln | Ala | Asp | His | Glu | Leu | His | Gly | Ala | Gln | Leu | Ser | Leu |
| 65 | | | | | 70 | | | | | 75 | | | | | 80 |
| Arg | Pro | Ala | Pro | Pro | Arg | Ala | Pro | Ala | Arg | Leu | Leu | Leu | Gln | Gly | Leu |
| | | | | 85 | | | | | 90 | | | | | 95 | |
| Pro | Pro | Gly | Thr | Thr | Pro | Gln | Arg | Leu | Glu | Gln | His | Val | Gln | Ala | Leu |
| | | | 100 | | | | | 105 | | | | | 110 | | |
| Leu | Arg | Ala | Ser | Gly | Leu | Pro | Val | Gln | Pro | Cys | Cys | Ala | Leu | Ala | Ser |
| | | | 115 | | | | | 120 | | | | | 125 | | |
| Pro | Arg | Pro | Asp | Arg | Ala | Leu | Val | Gln | Leu | Pro | Lys | Pro | Leu | Ser | Glu |
| | | 130 | | | | | 135 | | | | | 140 | | | |
| Ala | Asp | Val | Arg | Val | Leu | Glu | Glu | Gln | Ala | Gln | Asn | Leu | Gly | Leu | Glu |
| 145 | | | | | 150 | | | | | 155 | | | | | 160 |
| Gly | Thr | Leu | Val | Ser | Leu | Ala | Arg | Val | Pro | Gln | Ala | Arg | Ala | Val | Arg |
| | | | | 165 | | | | | 170 | | | | | 175 | |
| Val | Val | Gly | Asp | Gly | Ala | Ser | Val | Asp | Leu | Leu | Leu | Glu | Leu | Tyr | |
| | | | 180 | | | | | 185 | | | | | 190 | | |
| Leu | Glu | Asn | Glu | Arg | Arg | Ser | Gly | Gly | Pro | Leu | Glu | Asp | Leu | Gln | |
| | | | 195 | | | | | 200 | | | | | 205 | | |
| Arg | Leu | Pro | Gly | Pro | Leu | Gly | Thr | Val | Ala | Ser | Phe | Gln | Gln | Trp | Gln |
| | | 210 | | | | | 215 | | | | | 220 | | | |
| Val | Ala | Glu | Arg | Val | Leu | Gln | Gln | Glu | His | Arg | Leu | Gln | Gly | Ser | Glu |
| 225 | | | | | 230 | | | | | 235 | | | | | 240 |
| Leu | Ser | Leu | Val | Pro | His | Tyr | Asp | Ile | Leu | Glu | Pro | Glu | Glu | Leu | Ala |
| | | | | 245 | | | | | 250 | | | | | 255 | |
| Glu | Asn | Thr | Ser | Gly | Gly | Asp | His | Pro | Ser | Thr | Gln | Gly | Pro | Arg | Ala |
| | | | 260 | | | | | 265 | | | | | 270 | | |
| Thr | Lys | His | Ala | Leu | Leu | Arg | Thr | Gly | Gly | Leu | Val | Thr | Ala | Leu | Gln |
| | | 275 | | | | | 280 | | | | | 285 | | | |
| Gly | Ala | Gly | Thr | Val | Thr | Met | Gly | Ser | Gly | Glu | Glu | Pro | Gly | Gln | Ser |
| | 290 | | | | | 295 | | | | | 300 | | | | |
| Gly | Ala | Ser | Leu | Arg | Thr | Gly | Pro | Met | Val | Gln | Arg | Gly | Ile | Met | |
| 305 | | | | | 310 | | | | | 315 | | | | | 320 |
| Thr | Thr | Gly | Ser | Gly | Gln | Glu | Pro | Gly | Gln | Ser | Gly | Thr | Ser | Leu | Arg |
| | | | | 325 | | | | | 330 | | | | | 335 | |
| Thr | Gly | Pro | Met | Gly | Ser | Leu | Gly | Gln | Ala | Glu | Gln | Val | Ser | Ser | Met |
| | | | 340 | | | | | 345 | | | | | 350 | | |
| Pro | Met | Gly | Ser | Leu | Glu | His | Glu | Gly | Leu | Val | Ser | Leu | Arg | Pro | Val |
| | | | 355 | | | | | 360 | | | | | 365 | | |

-continued

```
Gly Leu Gln Glu Gln Glu Gly Pro Met Ser Leu Gly Pro Val Gly Ser
    370                 375                 380

Ala Gly Pro Val Glu Thr Ser Lys Gly Leu Leu Gly Gln Glu Gly Leu
385                 390                 395                 400

Val Glu Ile Ala Met Asp Ser Pro Glu Gln Glu Gly Leu Val Gly Pro
                405                 410                 415

Met Glu Ile Thr Met Gly Ser Leu Glu Lys Ala Gly Pro Val Ser Pro
                420                 425                 430

Gly Cys Val Lys Leu Ala Gly Gln Glu Gly Leu Val Glu Met Val Leu
            435                 440                 445

Leu Met Glu Pro Gly Ala Met Arg Phe Leu Gln Leu Tyr His Glu Asp
450                 455                 460

Leu Leu Ala Gly Leu Gly Asp Val Ala Leu Leu Pro Leu Glu Gly Pro
465                 470                 475                 480

Asp Met Thr Gly Phe Arg Leu Cys Gly Ala Gln Ala Ser Cys Gln Ala
                485                 490                 495

Ala Glu Glu Phe Leu Arg Ser Leu Leu Gly Ser Ile Ser Cys His Val
                500                 505                 510

Leu Cys Leu Glu His Pro Gly Ser Ala Arg Phe Leu Leu Gly Pro Glu
            515                 520                 525

Gly Gln His Leu Leu Gln Gly Leu Glu Ala Gln Phe Gln Cys Val Phe
530                 535                 540

Gly Thr Glu Arg Leu Ala Thr Ala Thr Leu Asp Thr Gly Leu Glu Glu
545                 550                 555                 560

Val Asp Pro Thr Glu Ala Leu Pro Val Leu Pro Gly Asn Ala His Thr
                565                 570                 575

Leu Trp Thr Pro Asp Ser Thr Gly Gly Asp Gln Glu Asp Val Ser Leu
                580                 585                 590

Glu Glu Val Arg Glu Leu Leu Ala Thr Leu Glu Gly Leu Asp Leu Asp
            595                 600                 605

Gly Glu Asp Trp Leu Pro Arg Glu Leu Glu Glu Gly Pro Gln Glu
610                 615                 620

Gln Pro Glu Glu Glu Val Thr Pro Gly His Glu Glu Glu Pro Val
625                 630                 635                 640

Ala Pro Ser Thr Val Ala Pro Arg Trp Leu Glu Glu Glu Ala Ala Leu
                645                 650                 655

Gln Leu Ala Leu His Arg Ser Leu Glu Pro Gln Gly Gln Val Ala Glu
                660                 665                 670

Gln Glu Glu Ala Ala Leu Arg Gln Ala Leu Thr Leu Ser Leu Leu
            675                 680                 685

Glu Gln Pro Pro Leu Glu Ala Glu Glu Pro Pro Asp Gly Gly Thr Asp
690                 695                 700

Gly Lys Ala Gln Leu Val Val His Ser Ala Phe Glu Gln Asp Val Glu
705                 710                 715                 720

Glu Leu Asp Arg Ala Leu Arg Ala Leu Glu Val His Val Gln Glu
                725                 730                 735

Glu Thr Val Gly Pro Trp Arg Arg Thr Leu Pro Ala Glu Leu Arg Ala
                740                 745                 750

Arg Leu Glu Arg Cys His Gly Val Ser Val Ala Leu Arg Gly Asp Cys
            755                 760                 765

Thr Ile Leu Arg Gly Phe Gly Ala His Pro Ala Arg Ala Ala Arg His
770                 775                 780

Leu Val Ala Leu Leu Ala Gly Pro Trp Asp Gln Ser Leu Ala Phe Pro
```

```
                785                 790                 795                 800
Leu Ala Ala Ser Gly Pro Thr Leu Ala Gly Gln Thr Leu Lys Gly Pro
                805                 810                 815

Trp Asn Asn Leu Glu Arg Leu Ala Glu Asn Thr Gly Glu Phe Gln Glu
                820                 825                 830

Val Val Arg Ala Phe Tyr Asp Thr Leu Asp Ala Ala Arg Ser Ser Ile
                835                 840                 845

Arg Val Val Arg Val Glu Arg Val Ser His Pro Leu Leu Gln Gln Gln
                850                 855                 860

Tyr Glu Leu Tyr Arg Glu Arg Leu Leu Gln Arg Cys Glu Arg Arg Pro
865                 870                 875                 880

Val Glu Gln Val Leu Tyr His Gly Thr Thr Ala Pro Ala Val Pro Asp
                885                 890                 895

Ile Cys Ala His Gly Phe Asn Arg Ser Phe Cys Gly Arg Asn Ala Thr
                900                 905                 910

Val Tyr Gly Lys Gly Val Tyr Phe Ala Arg Arg Ala Ser Leu Ser Val
                915                 920                 925

Gln Asp Arg Tyr Ser Pro Pro Asn Ala Asp Gly His Lys Ala Val Phe
                930                 935                 940

Val Ala Arg Val Leu Thr Gly Asp Tyr Gly Gln Gly Arg Arg Gly Leu
945                 950                 955                 960

Arg Ala Pro Pro Leu Arg Gly Pro Gly His Val Leu Leu Arg Tyr Asp
                965                 970                 975

Ser Ala Val Asp Cys Ile Cys Gln Pro Ser Ile Phe Val Ile Phe His
                980                 985                 990

Asp Thr Gln Ala Leu Pro Thr His  Leu Ile Thr Cys Glu  His Val Pro
                995                 1000                1005

Arg Ala  Ser Pro Asp Asp Pro  Ser Gly Leu Pro Gly  Arg Ser Pro
        1010                1015                1020

Asp Thr
    1025

<210> SEQ ID NO 3
<211> LENGTH: 701
<212> TYPE: PRT
<213> ORGANISM: Homo sapiens

<400> SEQUENCE: 3

Met Ala Gln Ala Gly Val Val Gly Glu Val Thr Gln Val Leu Cys Ala
1                   5                   10                  15

Ala Gly Gly Ala Leu Glu Leu Pro Glu Leu Arg Arg Arg Leu Arg Met
                20                  25                  30

Gly Leu Ser Ala Asp Ala Leu Glu Arg Leu Leu Arg Gln Arg Gly Arg
            35                  40                  45

Phe Val Val Ala Val Arg Ala Gly Gly Ala Ala Ala Pro Glu Arg
50                  55                  60

Val Val Leu Ala Ala Ser Pro Leu Arg Leu Cys Arg Ala His Gln Gly
65                  70                  75                  80

Ser Lys Pro Gly Cys Val Gly Leu Cys Ala Gln Leu His Leu Cys Arg
                85                  90                  95

Phe Met Val Tyr Gly Ala Cys Lys Phe Leu Arg Ala Gly Lys Asn Cys
                100                 105                 110

Arg Asn Ser His Ser Leu Thr Thr Glu His Asn Leu Ser Val Leu Arg
            115                 120                 125
```

-continued

```
Thr His Gly Val Asp His Leu Ser Tyr Asn Glu Leu Cys Gln Leu Leu
130                 135                 140

Phe Gln Asn Asp Pro Trp Leu Leu Pro Glu Ile Cys Gln His Tyr Asn
145                 150                 155                 160

Lys Gly Asp Gly Pro His Gly Ser Cys Ala Phe Gln Lys Gln Cys Ile
                165                 170                 175

Lys Leu His Ile Cys Gln Tyr Phe Leu Gln Gly Glu Cys Lys Phe Gly
                180                 185                 190

Thr Ser Cys Lys Arg Ser His Asp Phe Ser Asn Ser Glu Asn Leu Glu
                195                 200                 205

Lys Leu Glu Lys Leu Gly Met Ser Ser Asp Leu Val Ser Arg Leu Pro
210                 215                 220

Thr Ile Tyr Arg Asn Ala His Asp Ile Lys Asn Lys Ser Ser Ala Pro
225                 230                 235                 240

Ser Arg Val Pro Pro Leu Phe Val Pro Gln Gly Thr Ser Glu Arg Lys
                245                 250                 255

Asp Ser Ser Gly Ser Val Ser Pro Asn Thr Leu Ser Gln Glu Glu Gly
                260                 265                 270

Asp Gln Ile Cys Leu Tyr His Ile Arg Lys Ser Cys Ser Phe Gln Asp
                275                 280                 285

Lys Cys His Arg Val His Phe His Leu Pro Tyr Arg Trp Gln Phe Leu
290                 295                 300

Asp Arg Gly Lys Trp Glu Asp Leu Asp Asn Met Glu Leu Ile Glu Glu
305                 310                 315                 320

Ala Tyr Cys Asn Pro Lys Ile Glu Arg Ile Leu Cys Ser Glu Ser Ala
                325                 330                 335

Ser Thr Phe His Ser His Cys Leu Asn Phe Asn Ala Met Thr Tyr Gly
                340                 345                 350

Ala Thr Gln Ala Arg Arg Leu Ser Thr Ala Ser Ser Val Thr Lys Pro
                355                 360                 365

Pro His Phe Ile Leu Thr Thr Asp Trp Ile Trp Tyr Trp Ser Asp Glu
370                 375                 380

Phe Gly Ser Trp Gln Glu Tyr Gly Arg Gln Gly Thr Val His Pro Val
385                 390                 395                 400

Thr Thr Val Ser Ser Asp Val Glu Lys Ala Tyr Leu Ala Tyr Cys
                405                 410                 415

Thr Pro Gly Ser Asp Gly Gln Ala Ala Thr Leu Lys Phe Gln Ala Gly
                420                 425                 430

Lys His Asn Tyr Glu Leu Asp Phe Lys Ala Phe Val Gln Lys Asn Leu
                435                 440                 445

Val Tyr Gly Thr Thr Lys Lys Val Cys Arg Arg Pro Lys Tyr Val Ser
450                 455                 460

Pro Gln Asp Val Thr Thr Met Gln Thr Cys Asn Thr Lys Phe Pro Gly
465                 470                 475                 480

Pro Lys Ser Ile Pro Asp Tyr Trp Asp Ser Ser Ala Leu Pro Asp Pro
                485                 490                 495

Gly Phe Gln Lys Ile Thr Leu Ser Ser Ser Glu Glu Tyr Gln Lys
                500                 505                 510

Val Trp Asn Leu Phe Asn Arg Thr Leu Pro Phe Tyr Phe Val Gln Lys
                515                 520                 525

Ile Glu Arg Val Gln Asn Leu Ala Leu Trp Glu Val Tyr Gln Trp Gln
530                 535                 540

Lys Gly Gln Met Gln Lys Gln Asn Gly Gly Lys Ala Val Asp Glu Arg
```

```
                545                 550                 555                 560
        Gln Leu Phe His Gly Thr Ser Ala Ile Phe Val Asp Ala Ile Cys Gln
                        565                 570                 575

Gln Asn Phe Asp Trp Arg Val Cys Gly Val His Gly Thr Ser Tyr Gly
                        580                 585                 590

Lys Gly Ser Tyr Phe Ala Arg Asp Ala Ala Tyr Ser His His Tyr Ser
                        595                 600                 605

Lys Ser Asp Thr Gln Thr His Thr Met Phe Leu Ala Arg Val Leu Val
                        610                 615                 620

Gly Glu Phe Val Arg Gly Asn Ala Ser Phe Val Arg Pro Pro Ala Lys
        625                 630                 635                 640

Glu Gly Trp Ser Asn Ala Phe Tyr Asp Ser Cys Val Asn Ser Val Ser
                        645                 650                 655

Asp Pro Ser Ile Phe Val Ile Phe Glu Lys His Gln Val Tyr Pro Glu
                        660                 665                 670

Tyr Val Ile Gln Tyr Thr Thr Ser Ser Lys Pro Ser Val Thr Pro Ser
                        675                 680                 685

Ile Leu Leu Ala Leu Gly Ser Leu Phe Ser Ser Arg Gln
                        690                 695                 700

<210> SEQ ID NO 4
<211> LENGTH: 1801
<212> TYPE: PRT
<213> ORGANISM: Homo sapiens

<400> SEQUENCE: 4

Met Ala Val Pro Gly Ser Phe Pro Leu Leu Val Glu Gly Ser Trp Gly
        1               5                   10                  15

Pro Asp Pro Pro Lys Asn Leu Asn Thr Lys Leu Gln Met Tyr Phe Gln
                        20                  25                  30

Ser Pro Lys Arg Ser Gly Gly Gly Glu Cys Glu Val Arg Gln Asp Pro
                        35                  40                  45

Arg Ser Pro Ser Arg Phe Leu Val Phe Phe Tyr Pro Glu Asp Val Arg
        50                  55                  60

Gln Lys Val Leu Glu Arg Lys Asn His Glu Leu Val Trp Gln Gly Lys
        65                  70                  75                  80

Gly Thr Phe Lys Leu Thr Val Gln Leu Pro Ala Thr Pro Asp Glu Ile
                        85                  90                  95

Asp His Val Phe Glu Glu Leu Leu Thr Lys Glu Ser Lys Thr Lys
                        100                 105                 110

Glu Asp Val Lys Glu Pro Asp Val Ser Glu Glu Leu Asp Thr Lys Leu
                        115                 120                 125

Pro Leu Asp Gly Gly Leu Asp Lys Met Glu Asp Ile Pro Glu Glu Cys
                        130                 135                 140

Glu Asn Ile Ser Ser Leu Val Ala Phe Glu Asn Leu Lys Ala Asn Val
        145                 150                 155                 160

Thr Asp Ile Met Leu Ile Leu Leu Val Glu Asn Ile Ser Gly Leu Ser
                        165                 170                 175

Asn Asp Asp Phe Gln Val Glu Ile Ile Arg Asp Phe Asp Val Ala Val
                        180                 185                 190

Val Thr Phe Gln Lys His Ile Asp Thr Ile Arg Phe Val Asp Asp Cys
                        195                 200                 205

Thr Lys His His Ser Ile Lys Gln Leu Gln Leu Ser Pro Arg Leu Leu
                        210                 215                 220
```

```
Glu Val Thr Asn Thr Ile Arg Val Glu Asn Leu Pro Pro Gly Ala Asp
225                 230                 235                 240

Asp Tyr Ser Leu Lys Leu Phe Phe Glu Asn Pro Tyr Asn Gly Gly Gly
                245                 250                 255

Arg Val Ala Asn Val Glu Tyr Phe Pro Glu Glu Ser Ser Ala Leu Ile
                260                 265                 270

Glu Phe Phe Asp Arg Lys Val Leu Asp Thr Ile Met Ala Thr Lys Leu
                275                 280                 285

Asp Phe Asn Lys Met Pro Leu Ser Val Phe Pro Tyr Tyr Ala Ser Leu
                290                 295                 300

Gly Thr Ala Leu Tyr Gly Lys Glu Lys Pro Leu Ile Lys Leu Pro Ala
305                 310                 315                 320

Pro Phe Glu Glu Ser Leu Asp Leu Pro Leu Trp Lys Phe Leu Gln Lys
                325                 330                 335

Lys Asn His Leu Ile Glu Ile Asn Asp Glu Met Arg Arg Cys His
                340                 345                 350

Cys Glu Leu Thr Trp Ser Gln Leu Ser Gly Lys Val Thr Ile Arg Pro
                355                 360                 365

Ala Ala Thr Leu Val Asn Glu Gly Arg Pro Arg Ile Lys Thr Trp Gln
370                 375                 380

Ala Asp Thr Ser Thr Thr Leu Ser Ser Ile Arg Ser Lys Tyr Lys Val
385                 390                 395                 400

Asn Pro Ile Lys Val Asp Pro Thr Met Trp Asp Thr Ile Lys Asn Asp
                405                 410                 415

Val Lys Asp Asp Arg Ile Leu Ile Glu Phe Asp Thr Leu Lys Glu Met
                420                 425                 430

Val Ile Leu Ala Gly Lys Ser Glu Asp Val Gln Ser Ile Glu Val Gln
                435                 440                 445

Val Arg Glu Leu Ile Glu Ser Thr Thr Gln Lys Ile Lys Arg Glu Glu
                450                 455                 460

Gln Ser Leu Lys Glu Lys Met Ile Ile Ser Pro Gly Arg Tyr Phe Leu
465                 470                 475                 480

Leu Cys His Ser Ser Leu Leu Asp His Leu Leu Thr Glu Cys Pro Glu
                485                 490                 495

Ile Glu Ile Cys Tyr Asp Arg Val Thr Gln His Leu Cys Leu Lys Gly
                500                 505                 510

Pro Ser Ala Asp Val Tyr Lys Ala Lys Cys Glu Ile Gln Glu Lys Val
                515                 520                 525

Tyr Thr Met Ala Gln Lys Asn Ile Gln Val Ser Pro Glu Ile Phe Gln
                530                 535                 540

Phe Leu Gln Gln Val Asn Trp Lys Glu Phe Ser Lys Cys Leu Phe Ile
545                 550                 555                 560

Ala Gln Lys Ile Leu Ala Leu Tyr Glu Leu Glu Gly Thr Thr Val Leu
                565                 570                 575

Leu Thr Ser Cys Ser Ser Glu Ala Leu Leu Glu Ala Glu Lys Gln Met
                580                 585                 590

Leu Ser Ala Leu Asn Tyr Lys Arg Ile Glu Val Glu Asn Lys Glu Val
                595                 600                 605

Leu His Gly Lys Lys Trp Lys Gly Leu Thr His Asn Leu Leu Lys Lys
                610                 615                 620

Gln Asn Ser Ser Pro Asn Thr Val Ile Ile Asn Glu Leu Thr Ser Glu
625                 630                 635                 640

Thr Thr Ala Glu Val Ile Ile Thr Gly Cys Val Lys Glu Val Asn Glu
```

```
                  645                 650                 655
Thr Tyr Lys Leu Leu Phe Asn Phe Val Glu Gln Asn Met Lys Ile Glu
                660                 665                 670

Arg Leu Val Glu Val Lys Pro Ser Leu Val Ile Asp Tyr Leu Lys Thr
                675                 680                 685

Glu Lys Lys Leu Phe Trp Pro Lys Ile Lys Lys Val Asn Val Gln Val
                690                 695                 700

Ser Phe Asn Pro Glu Asn Lys Gln Lys Gly Ile Leu Leu Thr Gly Ser
705                 710                 715                 720

Lys Thr Glu Val Leu Lys Ala Val Asp Ile Val Lys Gln Val Trp Asp
                725                 730                 735

Ser Val Cys Val Lys Ser Val His Thr Asp Lys Pro Gly Ala Lys Gln
                740                 745                 750

Phe Phe Gln Asp Lys Ala Arg Phe Tyr Gln Ser Glu Ile Lys Arg Leu
                755                 760                 765

Phe Gly Cys Tyr Ile Glu Leu Gln Glu Asn Glu Val Met Lys Glu Gly
                770                 775                 780

Gly Ser Pro Ala Gly Gln Lys Cys Phe Ser Arg Thr Val Leu Ala Pro
785                 790                 795                 800

Gly Val Val Leu Ile Val Gln Gln Gly Asp Leu Ala Arg Leu Pro Val
                805                 810                 815

Asp Val Val Asn Ala Ser Asn Glu Asp Leu Lys His Tyr Gly Gly
                820                 825                 830

Leu Ala Ala Ala Leu Ser Lys Ala Ala Gly Pro Glu Leu Gln Ala Asp
                835                 840                 845

Cys Asp Gln Ile Val Lys Arg Glu Gly Arg Leu Leu Pro Gly Asn Ala
850                 855                 860

Thr Ile Ser Lys Ala Gly Lys Leu Pro Tyr His Val Ile His Ala
865                 870                 875                 880

Val Gly Pro Arg Trp Ser Gly Tyr Glu Ala Pro Arg Cys Val Tyr Leu
                885                 890                 895

Leu Arg Arg Ala Val Gln Leu Ser Leu Cys Leu Ala Glu Lys Tyr Lys
                900                 905                 910

Tyr Arg Ser Ile Ala Ile Pro Ala Ile Ser Ser Gly Val Phe Gly Phe
                915                 920                 925

Pro Leu Gly Arg Cys Val Glu Thr Ile Val Ser Ala Ile Lys Glu Asn
                930                 935                 940

Phe Gln Phe Lys Lys Asp Gly His Cys Leu Lys Glu Ile Tyr Leu Val
945                 950                 955                 960

Asp Val Ser Glu Lys Thr Val Glu Ala Phe Ala Glu Ala Val Lys Thr
                965                 970                 975

Val Phe Lys Ala Thr Leu Pro Asp Thr Ala Ala Pro Pro Gly Leu Pro
                980                 985                 990

Pro Ala Ala Ala Gly Pro Gly Lys  Thr Ser Trp Glu Lys  Gly Ser Leu
                995                 1000                1005

Val Ser  Pro Gly Gly Leu Gln  Met Leu Leu Val Lys  Glu Gly Val
        1010                1015                1020

Gln Asn  Ala Lys Thr Asp Val  Val Val Asn Ser Val  Pro Leu Asp
        1025                1030                1035

Leu Val  Leu Ser Arg Gly Pro  Leu Ser Lys Ser Leu  Leu Glu Lys
        1040                1045                1050

Ala Gly  Pro Glu Leu Gln Glu  Glu Leu Asp Thr Val  Gly Gln Gly
        1055                1060                1065
```

-continued

```
Val Ala Val Ser Met Gly Thr Val Leu Lys Thr Ser Ser Trp Asn
    1070            1075                1080

Leu Asp Cys Arg Tyr Val Leu His Val Val Ala Pro Glu Trp Arg
    1085            1090                1095

Asn Gly Ser Thr Ser Ser Leu Lys Ile Met Glu Asp Ile Ile Arg
    1100            1105                1110

Glu Cys Met Glu Ile Thr Glu Ser Leu Ser Leu Lys Ser Ile Ala
    1115            1120                1125

Phe Pro Ala Ile Gly Thr Gly Asn Leu Gly Phe Pro Lys Asn Ile
    1130            1135                1140

Phe Ala Glu Leu Ile Ile Ser Glu Val Phe Lys Phe Ser Ser Lys
    1145            1150                1155

Asn Gln Leu Lys Thr Leu Gln Glu Val His Phe Leu Leu His Pro
    1160            1165                1170

Ser Asp His Glu Asn Ile Gln Ala Phe Ser Asp Glu Phe Ala Arg
    1175            1180                1185

Arg Ala Asn Gly Asn Leu Val Ser Asp Lys Ile Pro Lys Ala Lys
    1190            1195                1200

Asp Thr Gln Gly Phe Tyr Gly Thr Val Ser Ser Pro Asp Ser Gly
    1205            1210                1215

Val Tyr Glu Met Lys Ile Gly Ser Ile Ile Phe Gln Val Ala Ser
    1220            1225                1230

Gly Asp Ile Thr Lys Glu Glu Ala Asp Val Ile Val Asn Ser Thr
    1235            1240                1245

Ser Asn Ser Phe Asn Leu Lys Ala Gly Val Ser Lys Ala Ile Leu
    1250            1255                1260

Glu Cys Ala Gly Gln Asn Val Glu Arg Glu Cys Ser Gln Gln Ala
    1265            1270                1275

Gln Gln Arg Lys Asn Asp Tyr Ile Ile Thr Gly Gly Gly Phe Leu
    1280            1285                1290

Arg Cys Lys Asn Ile Ile His Val Ile Gly Gly Asn Asp Val Lys
    1295            1300                1305

Ser Ser Val Ser Ser Val Leu Gln Glu Cys Glu Lys Lys Asn Tyr
    1310            1315                1320

Ser Ser Ile Cys Leu Pro Ala Ile Gly Thr Gly Asn Ala Lys Gln
    1325            1330                1335

His Pro Asp Lys Val Ala Glu Ala Ile Ile Asp Ala Ile Glu Asp
    1340            1345                1350

Phe Val Gln Lys Gly Ser Ala Gln Ser Val Lys Lys Val Lys Val
    1355            1360                1365

Val Ile Phe Leu Pro Gln Val Leu Asp Val Phe Tyr Ala Asn Met
    1370            1375                1380

Lys Lys Arg Glu Gly Thr Gln Leu Ser Ser Gln Ser Val Met
    1385            1390                1395

Ser Lys Leu Ala Ser Phe Leu Gly Phe Ser Lys Gln Ser Pro Gln
    1400            1405                1410

Lys Lys Asn His Leu Val Leu Glu Lys Lys Thr Glu Ser Ala Thr
    1415            1420                1425

Phe Arg Val Cys Gly Glu Asn Val Thr Cys Val Glu Tyr Ala Ile
    1430            1435                1440

Ser Trp Leu Gln Asp Leu Ile Glu Lys Glu Gln Cys Pro Tyr Thr
    1445            1450                1455
```

```
Ser Glu Asp Glu Cys Ile Lys Asp Phe Asp Glu Lys Glu Tyr Gln
    1460                1465                1470

Glu Leu Asn Glu Leu Gln Lys Lys Leu Asn Ile Asn Ile Ser Leu
    1475                1480                1485

Asp His Lys Arg Pro Leu Ile Lys Val Leu Gly Ile Ser Arg Asp
    1490                1495                1500

Val Met Gln Ala Arg Asp Glu Ile Glu Ala Met Ile Lys Arg Val
    1505                1510                1515

Arg Leu Ala Lys Glu Gln Glu Ser Arg Ala Asp Cys Ile Ser Glu
    1520                1525                1530

Phe Ile Glu Trp Gln Tyr Asn Asp Asn Asn Thr Ser His Cys Phe
    1535                1540                1545

Asn Lys Met Thr Asn Leu Lys Leu Glu Asp Ala Arg Arg Glu Lys
    1550                1555                1560

Lys Lys Thr Val Asp Val Lys Ile Asn His Arg His Tyr Thr Val
    1565                1570                1575

Asn Leu Asn Thr Tyr Thr Ala Thr Asp Thr Lys Gly His Ser Leu
    1580                1585                1590

Ser Val Gln Arg Leu Thr Lys Ser Lys Val Asp Ile Pro Ala His
    1595                1600                1605

Trp Ser Asp Met Lys Gln Gln Asn Phe Cys Val Val Glu Leu Leu
    1610                1615                1620

Pro Ser Asp Pro Glu Tyr Asn Thr Val Ala Ser Lys Phe Asn Gln
    1625                1630                1635

Thr Cys Ser His Phe Arg Ile Glu Lys Ile Glu Arg Ile Gln Asn
    1640                1645                1650

Pro Asp Leu Trp Asn Ser Tyr Gln Ala Lys Lys Lys Thr Met Asp
    1655                1660                1665

Ala Lys Asn Gly Gln Thr Met Asn Glu Lys Gln Leu Phe His Gly
    1670                1675                1680

Thr Asp Ala Gly Ser Val Pro His Val Asn Arg Asn Gly Phe Asn
    1685                1690                1695

Arg Ser Tyr Ala Gly Lys Asn Ala Val Ala Tyr Gly Lys Gly Thr
    1700                1705                1710

Tyr Phe Ala Val Asn Ala Asn Tyr Ser Ala Asn Asp Thr Tyr Ser
    1715                1720                1725

Arg Pro Asp Ala Asn Gly Arg Lys His Val Tyr Tyr Val Arg Val
    1730                1735                1740

Leu Thr Gly Ile Tyr Thr His Gly Asn His Ser Leu Ile Val Pro
    1745                1750                1755

Pro Ser Lys Asn Pro Gln Asn Pro Thr Asp Leu Tyr Asp Thr Val
    1760                1765                1770

Thr Asp Asn Val His His Pro Ser Leu Phe Val Ala Phe Tyr Asp
    1775                1780                1785

Tyr Gln Ala Tyr Pro Glu Tyr Leu Ile Thr Phe Arg Lys
    1790                1795                1800

<210> SEQ ID NO 5
<211> LENGTH: 444
<212> TYPE: PRT
<213> ORGANISM: Homo sapiens

<400> SEQUENCE: 5

Met Leu Gln Arg Ile Gly Leu Ile Phe Leu His Asn Ile Val Val Val
1               5                   10                  15
```

```
Ser Asn Cys Phe Tyr Phe Gln Ala Phe Leu Asp Glu Phe Thr Asn Trp
         20                  25                  30

Ser Arg Ile Asn Pro Asn Lys Ala Arg Ile Pro Met Ala Gly Asp Thr
             35                  40                  45

Gln Gly Val Val Gly Thr Val Ser Lys Pro Cys Phe Thr Ala Tyr Glu
 50                  55                  60

Met Lys Ile Gly Ala Ile Thr Phe Gln Val Ala Thr Gly Asp Ile Ala
 65                  70                  75                  80

Thr Glu Gln Val Asp Val Ile Val Asn Ser Thr Ala Arg Thr Phe Asn
             85                  90                  95

Arg Lys Ser Gly Val Ser Arg Ala Ile Leu Glu Gly Ala Gly Gln Ala
            100                 105                 110

Val Glu Ser Glu Cys Ala Val Leu Ala Ala Gln Pro His Arg Asp Phe
            115                 120                 125

Ile Ile Thr Pro Gly Gly Cys Leu Lys Cys Lys Ile Ile His Val
130                 135                 140

Pro Gly Gly Lys Asp Val Arg Lys Thr Val Thr Ser Val Leu Glu Glu
145                 150                 155                 160

Cys Glu Gln Arg Lys Tyr Thr Ser Val Ser Leu Pro Ala Ile Gly Thr
                165                 170                 175

Gly Asn Ala Gly Lys Asn Pro Ile Thr Val Ala Asp Asn Ile Ile Asp
            180                 185                 190

Ala Ile Val Asp Phe Ser Ser Gln His Ser Thr Pro Ser Leu Lys Thr
            195                 200                 205

Val Lys Val Val Ile Phe Gln Pro Glu Leu Leu Asn Ile Phe Tyr Asp
210                 215                 220

Ser Met Lys Lys Arg Asp Leu Ser Ala Ser Leu Asn Phe Gln Ser Thr
225                 230                 235                 240

Phe Ser Met Thr Thr Cys Asn Leu Pro Glu His Trp Thr Asp Met Asn
                245                 250                 255

His Gln Leu Phe Cys Met Val Gln Leu Glu Pro Gly Gln Ser Glu Tyr
            260                 265                 270

Asn Thr Ile Lys Asp Lys Phe Thr Arg Thr Cys Ser Ser Tyr Ala Ile
            275                 280                 285

Glu Lys Ile Glu Arg Ile Gln Asn Ala Phe Leu Trp Gln Ser Tyr Gln
290                 295                 300

Val Lys Lys Arg Gln Met Asp Ile Lys Asn Asp His Lys Asn Asn Glu
305                 310                 315                 320

Arg Leu Leu Phe His Gly Thr Asp Ala Asp Ser Val Pro Tyr Val Asn
                325                 330                 335

Gln His Gly Phe Asn Arg Ser Cys Ala Gly Lys Asn Ala Val Ser Tyr
            340                 345                 350

Gly Lys Gly Thr Tyr Phe Ala Val Asp Ala Ser Tyr Ser Ala Lys Asp
            355                 360                 365

Thr Tyr Ser Lys Pro Asp Ser Asn Gly Arg Lys His Met Tyr Val Val
370                 375                 380

Arg Val Leu Thr Gly Val Phe Thr Lys Gly Arg Ala Gly Leu Val Thr
385                 390                 395                 400

Pro Pro Pro Lys Asn Pro His Asn Pro Thr Asp Leu Phe Asp Ser Val
                405                 410                 415

Thr Asn Asn Thr Arg Ser Pro Lys Leu Phe Val Val Phe Phe Asp Asn
            420                 425                 430
```

```
Gln Ala Tyr Pro Glu Tyr Leu Ile Thr Phe Thr Ala
        435                 440
```

<210> SEQ ID NO 6
<211> LENGTH: 323
<212> TYPE: PRT
<213> ORGANISM: Homo sapiens

<400> SEQUENCE: 6

```
Met Gln Pro Ser Gly Trp Ala Ala Arg Glu Ala Gly Arg Asp
1               5                   10                  15

Met Leu Ala Ala Asp Leu Arg Cys Ser Leu Phe Ala Ser Ala Leu Gln
            20                  25                  30

Ser Tyr Lys Arg Asp Ser Val Leu Arg Pro Phe Pro Ala Ser Tyr Ala
        35                  40                  45

Arg Gly Asp Cys Lys Asp Phe Glu Ala Leu Leu Asp Ala Ser Lys
    50                  55                  60

Leu Pro Asn Leu Lys Glu Leu Leu Gln Ser Ser Gly Asp Asn His Lys
65                  70                  75                  80

Arg Ala Trp Asp Leu Val Ser Trp Ile Leu Ser Ser Lys Val Leu Thr
                85                  90                  95

Ile His Ser Ala Gly Lys Ala Glu Phe Glu Lys Ile Gln Lys Leu Thr
            100                 105                 110

Gly Ala Pro His Thr Pro Val Pro Ala Pro Asp Phe Leu Phe Glu Ile
        115                 120                 125

Glu Tyr Phe Asp Pro Ala Asn Ala Lys Phe Tyr Glu Thr Lys Gly Glu
    130                 135                 140

Arg Asp Leu Ile Tyr Ala Phe His Gly Ser Arg Leu Glu Asn Phe His
145                 150                 155                 160

Ser Ile Ile His Asn Gly Leu His Cys His Leu Asn Lys Thr Ser Leu
                165                 170                 175

Phe Gly Glu Gly Thr Tyr Leu Thr Ser Asp Leu Ser Leu Ala Leu Ile
            180                 185                 190

Tyr Ser Pro His Gly His Gly Trp Gln His Ser Leu Leu Gly Pro Ile
        195                 200                 205

Leu Ser Cys Val Ala Val Cys Glu Val Ile Asp His Pro Asp Val Lys
    210                 215                 220

Cys Gln Thr Lys Lys Lys Asp Ser Lys Glu Ile Asp Arg Arg Ala
225                 230                 235                 240

Arg Ile Lys His Ser Glu Gly Gly Asp Ile Pro Pro Lys Tyr Phe Val
                245                 250                 255

Val Thr Asn Asn Gln Leu Leu Arg Val Lys Tyr Leu Leu Val Tyr Ser
            260                 265                 270

Gln Lys Pro Pro Lys Ser Arg Ala Ser Ser Gln Leu Ser Trp Phe Ser
        275                 280                 285

Ser His Trp Phe Thr Val Met Ile Ser Leu Tyr Leu Leu Leu Leu
    290                 295                 300

Ile Val Ser Val Ile Asn Ser Ser Ala Phe Gln His Phe Trp Asn Arg
305                 310                 315                 320

Ala Lys Arg
```

<210> SEQ ID NO 7
<211> LENGTH: 39
<212> TYPE: PRT
<213> ORGANISM: Artificial sequence
<220> FEATURE:

<223> OTHER INFORMATION: Fusion tag

<400> SEQUENCE: 7

Met His His His His His Ser Ser Gly Val Asp Leu Gly Thr Glu
1               5                   10                  15

Asn Leu Tyr Phe Gln Ser Asn Ala Gly Leu Asn Asp Ile Phe Glu Ala
            20                  25                  30

Gln Lys Ile Glu Trp His Glu
        35

<210> SEQ ID NO 8
<211> LENGTH: 16
<212> TYPE: PRT
<213> ORGANISM: Artificial sequence
<220> FEATURE:
<223> OTHER INFORMATION: Fusion tag

<400> SEQUENCE: 8

Met Ala His His His His His His Glu Asn Leu Tyr Phe Gln Ser Met
1               5                   10                  15

<210> SEQ ID NO 9
<211> LENGTH: 24
<212> TYPE: PRT
<213> ORGANISM: Artificial sequence
<220> FEATURE:
<223> OTHER INFORMATION: Fusion tag

<400> SEQUENCE: 9

Met His His His His His Ser Ser Gly Val Asp Leu Gly Thr Glu
1               5                   10                  15

Asn Leu Tyr Phe Gln Ser Asn Ala
            20

<210> SEQ ID NO 10
<211> LENGTH: 24
<212> TYPE: PRT
<213> ORGANISM: Artificial sequence
<220> FEATURE:
<223> OTHER INFORMATION: Fusion tag

<400> SEQUENCE: 10

Met Ala His His His His His His Ser Ser Gly Val Asp Leu Gly Thr
1               5                   10                  15

Glu Asn Leu Tyr Phe Gln Ser Met
            20

<210> SEQ ID NO 11
<211> LENGTH: 171
<212> TYPE: PRT
<213> ORGANISM: Artificial sequence
<220> FEATURE:
<223> OTHER INFORMATION: NanoLuc

<400> SEQUENCE: 11

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

```
Glu Gly Leu Ser Gly Asp Gln Met Gly Gln Ile Glu Lys Ile Phe Lys
 65                  70                  75                  80

Val Val Tyr Pro Val Asp Asp His His Phe Lys Val Ile Leu His Tyr
                 85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```

<210> SEQ ID NO 12
<211> LENGTH: 516
<212> TYPE: DNA
<213> ORGANISM: Artificial sequence
<220> FEATURE:
<223> OTHER INFORMATION: NanoLuc

<400> SEQUENCE: 12

```
atggtcttca cactcgaaga tttcgttggg gactggcgac agacagccgg ctacaacctg    60
gaccaagtcc ttgaacaggg aggtgtgtcc agtttgtttc agaatctcgg ggtgtccgta   120
actccgatcc aaaggattgt cctgagcggt gaaaatgggc tgaagatcga catccatgtc   180
atcatcccgt atgaaggtct gagcggcgac caaatgggcc agatcgaaaa aattttaag   240 gtggtgtacc ctgtggatga tcatcacttt aaggtgatcc tgcactatgg cacactggta   300
atcgacgggg ttacgccgaa catgatcgac tatttcggac ggccgtatga aggcatcgcc   360
gtgttcgacg gcaaaaagat cactgtaaca gggaccctgt ggaacggcaa caaaattatc   420
gacgagcgcc tgatcaaccc cgacggctcc ctgctgttcc gagtaaccat caacggagtg   480
accggctggc ggctgtgcga acgcattctg gcgtaa                             516
```

<210> SEQ ID NO 13
<211> LENGTH: 1014
<212> TYPE: PRT
<213> ORGANISM: Homo sapiens

<400> SEQUENCE: 13

```
Met Ala Glu Ser Ser Asp Lys Leu Tyr Arg Val Glu Tyr Ala Lys Ser
  1               5                  10                  15

Gly Arg Ala Ser Cys Lys Lys Cys Ser Glu Ser Ile Pro Lys Asp Ser
             20                  25                  30

Leu Arg Met Ala Ile Met Val Gln Ser Pro Met Phe Asp Gly Lys Val
         35                  40                  45

Pro His Trp Tyr His Phe Ser Cys Phe Trp Lys Val Gly His Ser Ile
     50                  55                  60

Arg His Pro Asp Val Glu Val Asp Gly Phe Ser Glu Leu Arg Trp Asp
 65                  70                  75                  80

Asp Gln Gln Lys Val Lys Lys Thr Ala Glu Ala Gly Gly Val Thr Gly
                 85                  90                  95

Lys Gly Gln Asp Gly Ile Gly Ser Lys Ala Glu Lys Thr Leu Gly Asp
            100                 105                 110
```

-continued

```
Phe Ala Ala Glu Tyr Ala Lys Ser Asn Arg Ser Thr Cys Lys Gly Cys
            115                 120                 125
Met Glu Lys Ile Glu Lys Gly Gln Val Arg Leu Ser Lys Lys Met Val
        130                 135                 140
Asp Pro Glu Lys Pro Gln Leu Gly Met Ile Asp Arg Trp Tyr His Pro
145                 150                 155                 160
Gly Cys Phe Val Lys Asn Arg Glu Glu Leu Gly Phe Arg Pro Glu Tyr
                165                 170                 175
Ser Ala Ser Gln Leu Lys Gly Phe Ser Leu Leu Ala Thr Glu Asp Lys
            180                 185                 190
Glu Ala Leu Lys Lys Gln Leu Pro Gly Val Lys Ser Glu Gly Lys Arg
        195                 200                 205
Lys Gly Asp Glu Val Asp Gly Val Asp Glu Val Ala Lys Lys Lys Ser
    210                 215                 220
Lys Lys Glu Lys Asp Lys Asp Ser Lys Leu Glu Lys Ala Leu Lys Ala
225                 230                 235                 240
Gln Asn Asp Leu Ile Trp Asn Ile Lys Asp Glu Leu Lys Lys Val Cys
                245                 250                 255
Ser Thr Asn Asp Leu Lys Glu Leu Leu Ile Phe Asn Lys Gln Gln Val
            260                 265                 270
Pro Ser Gly Glu Ser Ala Ile Leu Asp Arg Val Ala Asp Gly Met Val
        275                 280                 285
Phe Gly Ala Leu Leu Pro Cys Glu Glu Cys Ser Gly Gln Leu Val Phe
    290                 295                 300
Lys Ser Asp Ala Tyr Tyr Cys Thr Gly Asp Val Thr Ala Trp Thr Lys
305                 310                 315                 320
Cys Met Val Lys Thr Gln Thr Pro Asn Arg Lys Glu Trp Val Thr Pro
                325                 330                 335
Lys Glu Phe Arg Glu Ile Ser Tyr Leu Lys Lys Leu Lys Val Lys Lys
            340                 345                 350
Gln Asp Arg Ile Phe Pro Pro Glu Thr Ser Ala Ser Val Ala Ala Thr
        355                 360                 365
Pro Pro Pro Ser Thr Ala Ser Ala Pro Ala Ala Val Asn Ser Ser Ala
    370                 375                 380
Ser Ala Asp Lys Pro Leu Ser Asn Met Lys Ile Leu Thr Leu Gly Lys
385                 390                 395                 400
Leu Ser Arg Asn Lys Asp Glu Val Lys Ala Met Ile Glu Lys Leu Gly
                405                 410                 415
Gly Lys Leu Thr Gly Thr Ala Asn Lys Ala Ser Leu Cys Ile Ser Thr
            420                 425                 430
Lys Lys Glu Val Glu Lys Met Asn Lys Lys Met Glu Glu Val Lys Glu
        435                 440                 445
Ala Asn Ile Arg Val Val Ser Glu Asp Phe Leu Gln Asp Val Ser Ala
    450                 455                 460
Ser Thr Lys Ser Leu Gln Glu Leu Phe Leu Ala His Ile Leu Ser Pro
465                 470                 475                 480
Trp Gly Ala Glu Val Lys Ala Glu Pro Val Glu Val Val Ala Pro Arg
                485                 490                 495
Gly Lys Ser Gly Ala Ala Leu Ser Lys Lys Ser Lys Gly Gln Val Lys
            500                 505                 510
Glu Glu Gly Ile Asn Lys Ser Glu Lys Arg Met Lys Leu Thr Leu Lys
        515                 520                 525
Gly Gly Ala Ala Val Asp Pro Asp Ser Gly Leu Glu His Ser Ala His
```

```
            530                 535                 540
Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                    565                 570                 575

Asp Asp Lys Glu Asn Arg Tyr Trp Ile Phe Arg Ser Trp Gly Arg Val
                580                 585                 590

Gly Thr Val Ile Gly Ser Asn Lys Leu Glu Gln Met Pro Ser Lys Glu
            595                 600                 605

Asp Ala Ile Glu His Phe Met Lys Leu Tyr Glu Glu Lys Thr Gly Asn
        610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
                660                 665                 670

Ile Lys Met Ile Phe Asp Val Glu Ser Met Lys Lys Ala Met Val Glu
            675                 680                 685

Tyr Glu Ile Asp Leu Gln Lys Met Pro Leu Gly Lys Leu Ser Lys Arg
        690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
                740                 745                 750

Asn Asn Ala Asp Ser Val Gln Ala Lys Val Glu Met Leu Asp Asn Leu
            755                 760                 765

Leu Asp Ile Glu Val Ala Tyr Ser Leu Leu Arg Gly Gly Ser Asp Asp
        770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Asn Ala Tyr Asp Leu Glu
                820                 825                 830

Val Ile Asp Ile Phe Lys Ile Glu Arg Glu Gly Glu Cys Gln Arg Tyr
            835                 840                 845

Lys Pro Phe Lys Gln Leu His Asn Arg Arg Leu Leu Trp His Gly Ser
        850                 855                 860

Arg Thr Thr Asn Phe Ala Gly Ile Leu Ser Gln Gly Leu Arg Ile Ala
865                 870                 875                 880

Pro Pro Glu Ala Pro Val Thr Gly Tyr Met Phe Gly Lys Gly Ile Tyr
                885                 890                 895

Phe Ala Asp Met Val Ser Lys Ser Ala Asn Tyr Cys His Thr Ser Gln
                900                 905                 910

Gly Asp Pro Ile Gly Leu Ile Leu Leu Gly Glu Val Ala Leu Gly Asn
            915                 920                 925

Met Tyr Glu Leu Lys His Ala Ser His Ile Ser Lys Leu Pro Lys Gly
        930                 935                 940

Lys His Ser Val Lys Gly Leu Gly Lys Thr Thr Pro Asp Pro Ser Ala
945                 950                 955                 960
```

```
Asn Ile Ser Leu Asp Gly Val Asp Val Pro Leu Gly Thr Gly Ile Ser
                965                 970                 975

Ser Gly Val Asn Asp Thr Ser Leu Leu Tyr Asn Glu Tyr Ile Val Tyr
            980                 985                 990

Asp Ile Ala Gln Val Asn Leu Lys Tyr Leu Leu Lys Leu Lys Phe Asn
        995                 1000                1005

Phe Lys Thr Ser Leu Trp
    1010

<210> SEQ ID NO 14
<211> LENGTH: 583
<212> TYPE: PRT
<213> ORGANISM: Homo sapiens

<400> SEQUENCE: 14

Met Ala Ala Arg Arg Arg Ser Thr Gly Gly Arg Ala Arg Ala
1               5                   10                  15

Leu Asn Glu Ser Lys Arg Val Asn Asn Gly Asn Thr Ala Pro Glu Asp
            20                  25                  30

Ser Ser Pro Ala Lys Lys Thr Arg Arg Cys Gln Arg Gln Glu Ser Lys
        35                  40                  45

Lys Met Pro Val Ala Gly Gly Lys Ala Asn Lys Asp Arg Thr Glu Asp
    50                  55                  60

Lys Gln Asp Gly Met Pro Gly Arg Ser Trp Ala Ser Lys Arg Val Ser
65                  70                  75                  80

Glu Ser Val Lys Ala Leu Leu Lys Gly Lys Ala Pro Val Asp Pro
                85                  90                  95

Glu Cys Thr Ala Lys Val Gly Lys Ala His Val Tyr Cys Glu Gly Asn
            100                 105                 110

Asp Val Tyr Asp Val Met Leu Asn Gln Thr Asn Leu Gln Phe Asn Asn
        115                 120                 125

Asn Lys Tyr Tyr Leu Ile Gln Leu Leu Glu Asp Ala Gln Arg Asn
    130                 135                 140

Phe Ser Val Trp Met Arg Trp Gly Arg Val Gly Lys Met Gly Gln His
145                 150                 155                 160

Ser Leu Val Ala Cys Ser Gly Asn Leu Asn Lys Ala Lys Glu Ile Phe
                165                 170                 175

Gln Lys Lys Phe Leu Asp Lys Thr Lys Asn Asn Trp Glu Asp Arg Glu
            180                 185                 190

Lys Phe Glu Lys Val Pro Gly Lys Tyr Asp Met Leu Gln Met Asp Tyr
        195                 200                 205

Ala Thr Asn Thr Gln Asp Glu Glu Thr Lys Lys Glu Glu Ser Leu
    210                 215                 220

Lys Ser Pro Leu Lys Pro Glu Ser Gln Leu Asp Leu Arg Val Gln Glu
225                 230                 235                 240

Leu Ile Lys Leu Ile Cys Asn Val Gln Ala Met Glu Glu Met Met Met
                245                 250                 255

Glu Met Lys Tyr Asn Thr Lys Lys Ala Pro Leu Gly Lys Leu Thr Val
            260                 265                 270

Ala Gln Ile Lys Ala Gly Tyr Gln Ser Leu Lys Lys Ile Glu Asp Cys
        275                 280                 285

Ile Arg Ala Gly Gln His Gly Arg Ala Leu Met Glu Ala Cys Asn Glu
    290                 295                 300

Phe Tyr Thr Arg Ile Pro His Asp Phe Gly Leu Arg Thr Pro Pro Leu
```

```
            305                 310                 315                 320
Ile Arg Thr Gln Lys Glu Leu Ser Glu Lys Ile Gln Leu Leu Glu Ala
                325                 330                 335
Leu Gly Asp Ile Glu Ile Ala Ile Lys Leu Val Lys Thr Glu Leu Gln
                340                 345                 350
Ser Pro Glu His Pro Leu Asp Gln His Tyr Arg Asn Leu His Cys Ala
                355                 360                 365
Leu Arg Pro Leu Asp His Glu Ser Tyr Glu Phe Lys Val Ile Ser Gln
                370                 375                 380
Tyr Leu Gln Ser Thr His Ala Pro Thr His Ser Asp Tyr Thr Met Thr
385                 390                 395                 400
Leu Leu Asp Leu Phe Glu Val Glu Lys Asp Gly Lys Glu Ala Phe
                405                 410                 415
Arg Glu Asp Leu His Asn Arg Met Leu Leu Trp His Gly Ser Arg Met
                420                 425                 430
Ser Asn Trp Val Gly Ile Leu Ser His Gly Leu Arg Ile Ala Pro Pro
                435                 440                 445
Glu Ala Pro Ile Thr Gly Tyr Met Phe Gly Lys Gly Ile Tyr Phe Ala
                450                 455                 460
Asp Met Ser Ser Lys Ser Ala Asn Tyr Cys Phe Ala Ser Arg Leu Lys
465                 470                 475                 480
Asn Thr Gly Leu Leu Leu Ser Glu Val Ala Leu Gly Gln Cys Asn
                485                 490                 495
Glu Leu Leu Glu Ala Asn Pro Lys Ala Glu Gly Leu Leu Gln Gly Lys
                500                 505                 510
His Ser Thr Lys Gly Leu Gly Lys Met Ala Pro Ser Ser Ala His Phe
                515                 520                 525
Val Thr Leu Asn Gly Ser Thr Val Pro Leu Gly Pro Ala Ser Asp Thr
                530                 535                 540
Gly Ile Leu Asn Pro Asp Gly Tyr Thr Leu Asn Tyr Asn Glu Tyr Ile
545                 550                 555                 560
Val Tyr Asn Pro Asn Gln Val Arg Met Arg Tyr Leu Leu Lys Val Gln
                565                 570                 575
Phe Asn Phe Leu Gln Leu Trp
                580

<210> SEQ ID NO 15
<211> LENGTH: 540
<212> TYPE: PRT
<213> ORGANISM: Homo sapiens

<400> SEQUENCE: 15

Met Ser Leu Leu Phe Leu Ala Met Ala Pro Lys Pro Lys Pro Trp Val
1               5                   10                  15
Gln Thr Glu Gly Pro Glu Lys Lys Gly Arg Gln Ala Gly Arg Glu
                20                  25                  30
Glu Asp Pro Phe Arg Ser Thr Ala Glu Ala Leu Lys Ala Ile Pro Ala
                35                  40                  45
Glu Lys Arg Ile Ile Arg Val Asp Pro Thr Cys Pro Leu Ser Ser Asn
                50                  55                  60
Pro Gly Thr Gln Val Tyr Glu Asp Tyr Asn Cys Thr Leu Asn Gln Thr
65                  70                  75                  80
Asn Ile Glu Asn Asn Asn Lys Phe Tyr Ile Ile Gln Leu Leu Gln
                85                  90                  95
```

```
Asp Ser Asn Arg Phe Phe Thr Cys Trp Asn Arg Trp Gly Arg Val Gly
                100                 105                 110

Glu Val Gly Gln Ser Lys Ile Asn His Phe Thr Arg Leu Glu Asp Ala
            115                 120                 125

Lys Lys Asp Phe Glu Lys Lys Phe Arg Glu Lys Thr Lys Asn Asn Trp
130                 135                 140

Ala Glu Arg Asp His Phe Val Ser His Pro Gly Lys Tyr Thr Leu Ile
145                 150                 155                 160

Glu Val Gln Ala Glu Asp Glu Ala Gln Glu Ala Val Val Lys Val Asp
                165                 170                 175

Arg Gly Pro Val Arg Thr Val Thr Lys Arg Val Gln Pro Cys Ser Leu
            180                 185                 190

Asp Pro Ala Thr Gln Lys Leu Ile Thr Asn Ile Phe Ser Lys Glu Met
        195                 200                 205

Phe Lys Asn Thr Met Ala Leu Met Asp Leu Asp Val Lys Lys Met Pro
210                 215                 220

Leu Gly Lys Leu Ser Lys Gln Gln Ile Ala Arg Gly Phe Glu Ala Leu
225                 230                 235                 240

Glu Ala Leu Glu Glu Ala Leu Lys Gly Pro Thr Asp Gly Gly Gln Ser
                245                 250                 255

Leu Glu Glu Leu Ser Ser His Phe Tyr Thr Val Ile Pro His Asn Phe
            260                 265                 270

Gly His Ser Gln Pro Pro Ile Asn Ser Pro Glu Leu Leu Gln Ala
        275                 280                 285

Lys Lys Asp Met Leu Leu Val Leu Ala Asp Ile Glu Leu Ala Gln Ala
290                 295                 300

Leu Gln Ala Val Ser Glu Gln Glu Lys Thr Val Glu Val Pro His
305                 310                 315                 320

Pro Leu Asp Arg Asp Tyr Gln Leu Leu Lys Cys Gln Leu Gln Leu Leu
                325                 330                 335

Asp Ser Gly Ala Pro Glu Tyr Lys Val Ile Gln Thr Tyr Leu Glu Gln
            340                 345                 350

Thr Gly Ser Asn His Arg Cys Pro Thr Leu Gln His Ile Trp Lys Val
        355                 360                 365

Asn Gln Glu Gly Glu Glu Asp Arg Phe Gln Ala His Ser Lys Leu Gly
370                 375                 380

Asn Arg Lys Leu Leu Trp His Gly Thr Asn Met Ala Val Val Ala Ala
385                 390                 395                 400

Ile Leu Thr Ser Gly Leu Arg Ile Met Pro His Ser Gly Gly Arg Val
                405                 410                 415

Gly Lys Gly Ile Tyr Phe Ala Ser Glu Asn Ser Lys Ser Ala Gly Tyr
            420                 425                 430

Val Ile Gly Met Lys Cys Gly Ala His His Val Gly Tyr Met Phe Leu
        435                 440                 445

Gly Glu Val Ala Leu Gly Arg Glu His His Ile Asn Thr Asp Asn Pro
450                 455                 460

Ser Leu Lys Ser Pro Pro Gly Phe Asp Ser Val Ile Ala Arg Gly
465                 470                 475                 480

His Thr Glu Pro Asp Pro Thr Gln Asp Thr Glu Leu Glu Leu Asp Gly
                485                 490                 495

Gln Gln Val Val Val Pro Gln Gly Gln Pro Val Pro Cys Pro Glu Phe
            500                 505                 510

Ser Ser Ser Thr Phe Ser Gln Ser Glu Tyr Leu Ile Tyr Gln Glu Ser
```

```
                515                 520                 525

Gln Cys Arg Leu Arg Tyr Leu Leu Glu Val His Leu
    530                 535                 540

<210> SEQ ID NO 16
<211> LENGTH: 1724
<212> TYPE: PRT
<213> ORGANISM: Homo sapiens

<400> SEQUENCE: 16

Met Val Met Gly Ile Phe Ala Asn Cys Ile Phe Cys Leu Lys Val Lys
1               5                   10                  15

Tyr Leu Pro Gln Gln Lys Lys Leu Gln Thr Asp Ile Lys Glu
            20                  25                  30

Asn Gly Gly Lys Phe Ser Phe Ser Leu Asn Pro Gln Cys Thr His Ile
        35                  40                  45

Ile Leu Asp Asn Ala Asp Val Leu Ser Gln Tyr Gln Leu Asn Ser Ile
    50                  55                  60

Gln Lys Asn His Val His Ile Ala Asn Pro Asp Phe Ile Trp Lys Ser
65                  70                  75                  80

Ile Arg Glu Lys Arg Leu Leu Asp Val Lys Asn Tyr Asp Pro Tyr Lys
                85                  90                  95

Pro Leu Asp Ile Thr Pro Pro Asp Gln Lys Ala Ser Ser Ser Glu
            100                 105                 110

Val Lys Thr Glu Gly Leu Cys Pro Asp Ser Ala Thr Glu Glu Glu Asp
        115                 120                 125

Thr Val Glu Leu Thr Glu Phe Gly Met Gln Asn Val Glu Ile Pro His
    130                 135                 140

Leu Pro Gln Asp Phe Glu Val Ala Lys Tyr Asn Thr Leu Glu Lys Val
145                 150                 155                 160

Gly Met Glu Gly Gly Gln Glu Ala Val Val Glu Leu Gln Cys Ser
                165                 170                 175

Arg Asp Ser Arg Asp Cys Pro Phe Leu Ile Ser Ser His Phe Leu Leu
            180                 185                 190

Asp Asp Gly Met Glu Thr Arg Arg Gln Phe Ala Ile Lys Lys Thr Ser
        195                 200                 205

Glu Asp Ala Ser Glu Tyr Phe Glu Asn Tyr Ile Glu Glu Leu Lys Lys
    210                 215                 220

Gln Gly Phe Leu Leu Arg Glu His Phe Thr Pro Glu Ala Thr Gln Leu
225                 230                 235                 240

Ala Ser Glu Gln Leu Gln Ala Leu Leu Leu Glu Glu Val Met Asn Ser
                245                 250                 255

Ser Thr Leu Ser Gln Glu Val Ser Asp Leu Val Glu Met Ile Trp Ala
            260                 265                 270

Glu Ala Leu Gly His Leu Glu His Met Leu Leu Lys Pro Val Asn Arg
        275                 280                 285

Ile Ser Leu Asn Asp Val Ser Lys Ala Glu Gly Ile Leu Leu Leu Val
    290                 295                 300

Lys Ala Ala Leu Lys Asn Gly Glu Thr Ala Glu Gln Leu Gln Lys Met
305                 310                 315                 320

Met Thr Glu Phe Tyr Arg Leu Ile Pro His Lys Gly Thr Met Pro Lys
                325                 330                 335

Glu Val Asn Leu Gly Leu Leu Ala Lys Lys Ala Asp Leu Cys Gln Leu
            340                 345                 350
```

-continued

```
Ile Arg Asp Met Val Asn Val Cys Glu Thr Asn Leu Ser Lys Pro Asn
            355                 360                 365
Pro Pro Ser Leu Ala Lys Tyr Arg Ala Leu Arg Cys Lys Ile Glu His
370                 375                 380
Val Glu Gln Asn Thr Glu Glu Phe Leu Arg Val Arg Lys Glu Val Leu
385                 390                 395                 400
Gln Asn His His Ser Lys Ser Pro Val Asp Val Leu Gln Ile Phe Arg
                405                 410                 415
Val Gly Arg Val Asn Glu Thr Thr Glu Phe Leu Ser Lys Leu Gly Asn
            420                 425                 430
Val Arg Pro Leu Leu His Gly Ser Pro Val Gln Asn Ile Val Gly Ile
            435                 440                 445
Leu Cys Arg Gly Leu Leu Leu Pro Lys Val Val Glu Asp Arg Gly Val
        450                 455                 460
Gln Arg Thr Asp Val Gly Asn Leu Gly Ser Gly Ile Tyr Phe Ser Asp
465                 470                 475                 480
Ser Leu Ser Thr Ser Ile Lys Tyr Ser His Pro Gly Glu Thr Asp Gly
                485                 490                 495
Thr Arg Leu Leu Leu Ile Cys Asp Val Ala Leu Gly Lys Cys Met Asp
            500                 505                 510
Leu His Glu Lys Asp Phe Ser Leu Thr Glu Ala Pro Pro Gly Tyr Asp
        515                 520                 525
Ser Val His Gly Val Ser Gln Thr Ala Ser Val Thr Thr Asp Phe Glu
    530                 535                 540
Asp Asp Glu Phe Val Val Tyr Lys Thr Asn Gln Val Lys Met Lys Tyr
545                 550                 555                 560
Ile Ile Lys Phe Ser Met Pro Gly Asp Gln Ile Lys Asp Phe His Pro
                565                 570                 575
Ser Asp His Thr Glu Leu Glu Glu Tyr Arg Pro Glu Phe Ser Asn Phe
            580                 585                 590
Ser Lys Val Glu Asp Tyr Gln Leu Pro Asp Ala Lys Thr Ser Ser Ser
        595                 600                 605
Thr Lys Ala Gly Leu Gln Asp Ala Ser Gly Asn Leu Val Pro Leu Glu
    610                 615                 620
Asp Val His Ile Lys Gly Arg Ile Ile Asp Thr Val Ala Gln Val Ile
625                 630                 635                 640
Val Phe Gln Thr Tyr Thr Asn Lys Ser His Val Pro Ile Glu Ala Lys
                645                 650                 655
Tyr Ile Phe Pro Leu Asp Asp Lys Ala Ala Val Cys Gly Phe Glu Ala
            660                 665                 670
Phe Ile Asn Gly Lys His Ile Val Gly Glu Ile Lys Glu Lys Glu Glu
        675                 680                 685
Ala Gln Gln Glu Tyr Leu Glu Ala Val Thr Gln Gly His Gly Ala Tyr
    690                 695                 700
Leu Met Ser Gln Asp Ala Pro Asp Val Phe Thr Val Ser Val Gly Asn
705                 710                 715                 720
Leu Pro Pro Lys Ala Lys Val Leu Ile Lys Ile Thr Tyr Ile Thr Glu
                725                 730                 735
Leu Ser Ile Leu Gly Thr Val Gly Val Phe Phe Met Pro Ala Thr Val
            740                 745                 750
Ala Pro Trp Gln Gln Asp Lys Ala Leu Asn Glu Asn Leu Gln Asp Thr
        755                 760                 765
Val Glu Lys Ile Cys Ile Lys Glu Ile Gly Thr Lys Gln Ser Phe Ser
```

-continued

```
            770             775             780
Leu Thr Met Ser Ile Glu Met Pro Tyr Val Ile Glu Phe Ile Phe Ser
785             790             795             800

Asp Thr His Glu Leu Lys Gln Lys Arg Thr Asp Cys Lys Ala Val Ile
            805             810             815

Ser Thr Met Glu Gly Ser Ser Leu Asp Ser Ser Gly Phe Ser Leu His
            820             825             830

Ile Gly Leu Ser Ala Ala Tyr Leu Pro Arg Met Trp Val Glu Lys His
            835             840             845

Pro Glu Lys Glu Ser Glu Ala Cys Met Leu Val Phe Gln Pro Asp Leu
850             855             860

Asp Val Asp Leu Pro Asp Leu Ala Ser Glu Ser Glu Val Ile Ile Cys
865             870             875             880

Leu Asp Cys Ser Ser Ser Met Glu Gly Val Thr Phe Leu Gln Ala Lys
            885             890             895

Gln Ile Ala Leu His Ala Leu Ser Leu Val Gly Glu Lys Gln Lys Val
            900             905             910

Asn Ile Ile Gln Phe Gly Thr Gly Tyr Lys Glu Leu Phe Ser Tyr Pro
            915             920             925

Lys His Ile Thr Ser Asn Thr Met Ala Ala Glu Phe Ile Met Ser Ala
            930             935             940

Thr Pro Thr Met Gly Asn Thr Asp Phe Trp Lys Thr Leu Arg Tyr Leu
945             950             955             960

Ser Leu Leu Tyr Pro Ala Arg Gly Ser Arg Asn Ile Leu Leu Val Ser
            965             970             975

Asp Gly His Leu Gln Asp Glu Ser Leu Thr Leu Gln Leu Val Lys Arg
            980             985             990

Ser Arg Pro His Thr Arg Leu Phe Ala Cys Gly Ile Gly Ser Thr Ala
            995             1000            1005

Asn Arg His Val Leu Arg Ile Leu Ser Gln Cys Gly Ala Gly Val
            1010            1015            1020

Phe Glu Tyr Phe Asn Ala Lys Ser Lys His Ser Trp Arg Lys Gln
            1025            1030            1035

Ile Glu Asp Gln Met Thr Arg Leu Cys Ser Pro Ser Cys His Ser
            1040            1045            1050

Val Ser Val Lys Trp Gln Gln Leu Asn Pro Asp Val Pro Glu Ala
            1055            1060            1065

Leu Gln Ala Pro Ala Gln Val Pro Ser Leu Phe Leu Asn Asp Arg
            1070            1075            1080

Leu Leu Val Tyr Gly Phe Ile Pro His Cys Thr Gln Ala Thr Leu
            1085            1090            1095

Cys Ala Leu Ile Gln Glu Lys Glu Phe Arg Thr Met Val Ser Thr
            1100            1105            1110

Thr Glu Leu Gln Lys Thr Thr Gly Thr Met Ile His Lys Leu Ala
            1115            1120            1125

Ala Arg Ala Leu Ile Arg Asp Tyr Glu Asp Gly Ile Leu His Glu
            1130            1135            1140

Asn Glu Thr Ser His Glu Met Lys Lys Gln Thr Leu Lys Ser Leu
            1145            1150            1155

Ile Ile Lys Leu Ser Lys Glu Asn Ser Leu Ile Thr Gln Phe Thr
            1160            1165            1170

Ser Phe Val Ala Val Glu Lys Arg Asp Glu Asn Glu Ser Pro Phe
            1175            1180            1185
```

```
Pro Asp Ile Pro Lys Val Ser Glu Leu Ile Ala Lys Glu Asp Val
1190                1195                1200

Asp Phe Leu Pro Tyr Met Ser Trp Gln Gly Glu Pro Gln Glu Ala
1205                1210                1215

Val Arg Asn Gln Ser Leu Leu Ala Ser Ser Glu Trp Pro Glu Leu
1220                1225                1230

Arg Leu Ser Lys Arg Lys His Arg Lys Ile Pro Phe Ser Lys Arg
1235                1240                1245

Lys Met Glu Leu Ser Gln Pro Glu Val Ser Glu Asp Phe Glu Glu
1250                1255                1260

Asp Gly Leu Gly Val Leu Pro Ala Phe Thr Ser Asn Leu Glu Arg
1265                1270                1275

Gly Gly Val Glu Lys Leu Leu Asp Leu Ser Trp Thr Glu Ser Cys
1280                1285                1290

Lys Pro Thr Ala Thr Glu Pro Leu Phe Lys Lys Val Ser Pro Trp
1295                1300                1305

Glu Thr Ser Thr Ser Ser Phe Phe Pro Ile Leu Ala Pro Ala Val
1310                1315                1320

Gly Ser Tyr Leu Pro Pro Thr Ala Arg Ala His Ser Pro Ala Ser
1325                1330                1335

Leu Ser Phe Ala Ser Tyr Arg Gln Val Ala Ser Phe Gly Ser Ala
1340                1345                1350

Ala Pro Pro Arg Gln Phe Asp Ala Ser Gln Phe Ser Gln Gly Pro
1355                1360                1365

Val Pro Gly Thr Cys Ala Asp Trp Ile Pro Gln Ser Ala Ser Cys
1370                1375                1380

Pro Thr Gly Pro Pro Gln Asn Pro Pro Ser Ser Pro Tyr Cys Gly
1385                1390                1395

Ile Val Phe Ser Gly Ser Ser Leu Ser Ser Ala Gln Ser Ala Pro
1400                1405                1410

Leu Gln His Pro Gly Gly Phe Thr Thr Arg Pro Ser Ala Gly Thr
1415                1420                1425

Phe Pro Glu Leu Asp Ser Pro Gln Leu His Phe Ser Leu Pro Thr
1430                1435                1440

Asp Pro Asp Pro Ile Arg Gly Phe Gly Ser Tyr His Pro Ser Ala
1445                1450                1455

Ser Ser Pro Phe His Phe Gln Pro Ser Ala Ala Ser Leu Thr Ala
1460                1465                1470

Asn Leu Arg Leu Pro Met Ala Ser Ala Leu Pro Glu Ala Leu Cys
1475                1480                1485

Ser Gln Ser Arg Thr Thr Pro Val Asp Leu Cys Leu Leu Glu Glu
1490                1495                1500

Ser Val Gly Ser Leu Glu Gly Ser Arg Cys Pro Val Phe Ala Phe
1505                1510                1515

Gln Ser Ser Asp Thr Glu Ser Asp Glu Leu Ser Glu Val Leu Gln
1520                1525                1530

Asp Ser Cys Phe Leu Gln Ile Lys Cys Asp Thr Lys Asp Asp Ser
1535                1540                1545

Ile Leu Cys Phe Leu Glu Val Lys Glu Glu Asp Glu Ile Val Cys
1550                1555                1560

Ile Gln His Trp Gln Asp Ala Val Pro Trp Thr Glu Leu Leu Ser
1565                1570                1575
```

-continued

```
Leu Gln Thr Glu Asp Gly Phe Trp Lys Leu Thr Pro Glu Leu Gly
    1580                1585                1590

Leu Ile Leu Asn Leu Asn Thr Asn Gly Leu His Ser Phe Leu Lys
    1595                1600                1605

Gln Lys Gly Ile Gln Ser Leu Gly Val Lys Gly Arg Glu Cys Leu
    1610                1615                1620

Leu Asp Leu Ile Ala Thr Met Leu Val Leu Gln Phe Ile Arg Thr
    1625                1630                1635

Arg Leu Glu Lys Glu Gly Ile Val Phe Lys Ser Leu Met Lys Met
    1640                1645                1650

Asp Asp Ala Ser Ile Ser Arg Asn Ile Pro Trp Ala Phe Glu Ala
    1655                1660                1665

Ile Lys Gln Ala Ser Glu Trp Val Arg Arg Thr Glu Gly Gln Tyr
    1670                1675                1680

Pro Ser Ile Cys Pro Arg Leu Glu Leu Gly Asn Asp Trp Asp Ser
    1685                1690                1695

Ala Thr Lys Gln Leu Leu Gly Leu Gln Pro Ile Ser Thr Val Ser
    1700                1705                1710

Pro Leu His Arg Val Leu His Tyr Ser Gln Gly
    1715                1720

<210> SEQ ID NO 17
<211> LENGTH: 1327
<212> TYPE: PRT
<213> ORGANISM: Homo sapiens

<400> SEQUENCE: 17

Met Ala Ala Ser Arg Arg Ser Gln His His His His His Gln Gln
1               5                   10                  15

Gln Leu Gln Pro Ala Pro Gly Ala Ser Ala Pro Pro Pro Pro Pro
                20                  25                  30

Pro Pro Leu Ser Pro Gly Leu Ala Pro Gly Thr Thr Pro Ala Ser
                35                  40                  45

Thr Ala Ser Gly Leu Ala Pro Phe Ala Ser Pro Arg His Gly Leu Ala
    50                  55                  60

Leu Pro Glu Gly Asp Gly Ser Arg Asp Pro Asp Arg Pro Arg Ser
65                  70                  75                  80

Pro Asp Pro Val Asp Gly Thr Ser Cys Cys Ser Thr Thr Ser Thr Ile
                85                  90                  95

Cys Thr Val Ala Ala Ala Pro Val Pro Ala Val Ser Thr Ser Ser
                100                 105                 110

Ala Ala Gly Val Ala Pro Asn Pro Ala Gly Ser Gly Ser Asn Asn Ser
                115                 120                 125

Pro Ser Ser Ser Ser Ser Pro Thr Ser Ser Ser Ser Ser Pro Ser
    130                 135                 140

Ser Pro Gly Ser Ser Leu Ala Glu Ser Pro Glu Ala Ala Gly Val Ser
145                 150                 155                 160

Ser Thr Ala Pro Leu Gly Pro Gly Ala Ala Gly Pro Gly Thr Gly Val
                165                 170                 175

Pro Ala Val Ser Gly Ala Leu Arg Glu Leu Leu Glu Ala Cys Arg Asn
                180                 185                 190

Gly Asp Val Ser Arg Val Lys Arg Leu Val Asp Ala Ala Asn Val Asn
                195                 200                 205

Ala Lys Asp Met Ala Gly Arg Lys Ser Ser Pro Leu His Phe Ala Ala
    210                 215                 220
```

```
Gly Phe Gly Arg Lys Asp Val Val Glu His Leu Leu Gln Met Gly Ala
225                 230                 235                 240

Asn Val His Ala Arg Asp Asp Gly Gly Leu Ile Pro Leu His Asn Ala
            245                 250                 255

Cys Ser Phe Gly His Ala Glu Val Val Ser Leu Leu Leu Cys Gln Gly
                260                 265                 270

Ala Asp Pro Asn Ala Arg Asp Asn Trp Asn Tyr Thr Pro Leu His Glu
            275                 280                 285

Ala Ala Ile Lys Gly Lys Ile Asp Val Cys Ile Val Leu Leu Gln His
            290                 295                 300

Gly Ala Asp Pro Asn Ile Arg Asn Thr Asp Gly Lys Ser Ala Leu Asp
305                 310                 315                 320

Leu Ala Asp Pro Ser Ala Lys Ala Val Leu Thr Gly Glu Tyr Lys Lys
                325                 330                 335

Asp Glu Leu Leu Glu Ala Ala Arg Ser Gly Asn Glu Glu Lys Leu Met
            340                 345                 350

Ala Leu Leu Thr Pro Leu Asn Val Asn Cys His Ala Ser Asp Gly Arg
            355                 360                 365

Lys Ser Thr Pro Leu His Leu Ala Ala Gly Tyr Asn Arg Val Arg Ile
            370                 375                 380

Val Gln Leu Leu Leu Gln His Gly Ala Asp Val His Ala Lys Asp Lys
385                 390                 395                 400

Gly Gly Leu Val Pro Leu His Asn Ala Cys Ser Tyr Gly His Tyr Glu
                405                 410                 415

Val Thr Glu Leu Leu Lys His Gly Ala Cys Val Asn Ala Met Asp
            420                 425                 430

Leu Trp Gln Phe Thr Pro Leu His Glu Ala Ala Ser Lys Asn Arg Val
            435                 440                 445

Glu Val Cys Ser Leu Leu Leu Ser His Gly Ala Asp Pro Thr Leu Val
450                 455                 460

Asn Cys His Gly Lys Ser Ala Val Asp Met Ala Pro Thr Pro Glu Leu
465                 470                 475                 480

Arg Glu Arg Leu Thr Tyr Glu Phe Lys Gly His Ser Leu Leu Gln Ala
                485                 490                 495

Ala Arg Glu Ala Asp Leu Ala Lys Val Lys Lys Thr Leu Ala Leu Glu
            500                 505                 510

Ile Ile Asn Phe Lys Gln Pro Gln Ser His Glu Thr Ala Leu His Cys
            515                 520                 525

Ala Val Ala Ser Leu His Pro Lys Arg Lys Gln Val Thr Glu Leu Leu
            530                 535                 540

Leu Arg Lys Gly Ala Asn Val Asn Glu Lys Asn Lys Asp Phe Met Thr
545                 550                 555                 560

Pro Leu His Val Ala Ala Glu Arg Ala His Asn Asp Val Met Glu Val
                565                 570                 575

Leu His Lys His Gly Ala Lys Met Asn Ala Leu Asp Thr Leu Gly Gln
            580                 585                 590

Thr Ala Leu His Arg Ala Ala Leu Ala Gly His Leu Gln Thr Cys Arg
            595                 600                 605

Leu Leu Leu Ser Tyr Gly Ser Asp Pro Ser Ile Ile Ser Leu Gln Gly
            610                 615                 620

Phe Thr Ala Ala Gln Met Gly Asn Glu Ala Val Gln Gln Ile Leu Ser
625                 630                 635                 640
```

-continued

Glu Ser Thr Pro Ile Arg Thr Ser Asp Val Asp Tyr Arg Leu Leu Glu
                    645                 650                 655

Ala Ser Lys Ala Gly Asp Leu Glu Thr Val Lys Gln Leu Cys Ser Ser
            660                 665                 670

Gln Asn Val Asn Cys Arg Asp Leu Glu Gly Arg His Ser Thr Pro Leu
        675                 680                 685

His Phe Ala Ala Gly Tyr Asn Arg Val Ser Val Glu Tyr Leu Leu
690                 695                 700

His His Gly Ala Asp Val His Ala Lys Asp Lys Gly Gly Leu Val Pro
705                 710                 715                 720

Leu His Asn Ala Cys Ser Tyr Gly His Tyr Glu Val Ala Glu Leu Leu
                    725                 730                 735

Val Arg His Gly Ala Ser Val Asn Val Ala Asp Leu Trp Lys Phe Thr
                740                 745                 750

Pro Leu His Glu Ala Ala Lys Gly Lys Tyr Glu Ile Cys Lys Leu
            755                 760                 765

Leu Leu Lys His Gly Ala Asp Pro Thr Lys Lys Asn Arg Asp Gly Asn
770                 775                 780

Thr Pro Leu Asp Leu Val Lys Glu Gly Asp Thr Asp Ile Gln Asp Leu
785                 790                 795                 800

Leu Arg Gly Asp Ala Ala Leu Leu Asp Ala Ala Lys Lys Gly Cys Leu
                    805                 810                 815

Ala Arg Val Gln Lys Leu Cys Thr Pro Glu Asn Ile Asn Cys Arg Asp
                820                 825                 830

Thr Gln Gly Arg Asn Ser Thr Pro Leu His Leu Ala Ala Gly Tyr Asn
            835                 840                 845

Asn Leu Glu Val Ala Glu Tyr Leu Leu Glu His Gly Ala Asp Val Asn
850                 855                 860

Ala Gln Asp Lys Gly Gly Leu Ile Pro Leu His Asn Ala Ala Ser Tyr
865                 870                 875                 880

Gly His Val Asp Ile Ala Ala Leu Leu Ile Lys Tyr Asn Thr Cys Val
                    885                 890                 895

Asn Ala Thr Asp Lys Trp Ala Phe Thr Pro Leu His Glu Ala Ala Gln
                900                 905                 910

Lys Gly Arg Thr Gln Leu Cys Ala Leu Leu Leu Ala His Gly Ala Asp
            915                 920                 925

Pro Thr Met Lys Asn Gln Glu Gly Gln Thr Pro Leu Asp Leu Ala Thr
            930                 935                 940

Ala Asp Asp Ile Arg Ala Leu Leu Ile Asp Ala Met Pro Pro Glu Ala
945                 950                 955                 960

Leu Pro Thr Cys Phe Lys Pro Gln Ala Thr Val Val Ser Ala Ser Leu
                    965                 970                 975

Ile Ser Pro Ala Ser Thr Pro Ser Cys Leu Ser Ala Ala Ser Ser Ile
                980                 985                 990

Asp Asn Leu Thr Gly Pro Leu Ala Glu Leu Ala Val Gly Gly Ala Ser
            995                 1000                1005

Asn Ala Gly Asp Gly Ala Ala Gly Thr Glu Arg Lys Glu Gly Glu
        1010                1015                1020

Val Ala Gly Leu Asp Met Asn Ile Ser Gln Phe Leu Lys Ser Leu
        1025                1030                1035

Gly Leu Glu His Leu Arg Asp Ile Phe Glu Thr Glu Gln Ile Thr
        1040                1045                1050

Leu Asp Val Leu Ala Asp Met Gly His Glu Glu Leu Lys Glu Ile

```
              1055                1060                1065

Gly Ile Asn Ala Tyr Gly His Arg His Lys Leu Ile Lys Gly Val
        1070                1075                1080

Glu Arg Leu Leu Gly Gly Gln Gln Gly Thr Asn Pro Tyr Leu Thr
    1085                1090                1095

Phe His Cys Val Asn Gln Gly Thr Ile Leu Leu Asp Leu Ala Pro
        1100                1105                1110

Glu Asp Lys Glu Tyr Gln Ser Val Glu Glu Met Gln Ser Thr
    1115                1120                1125

Ile Arg Glu His Arg Asp Gly Gly Asn Ala Gly Ile Phe Asn
    1130                1135                1140

Arg Tyr Asn Val Ile Arg Ile Gln Lys Val Val Asn Lys Lys Leu
    1145                1150                1155

Arg Glu Arg Phe Cys His Arg Gln Lys Glu Val Ser Glu Glu Asn
    1160                1165                1170

His Asn His His Asn Glu Arg Met Leu Phe His Gly Ser Pro Phe
    1175                1180                1185

Ile Asn Ala Ile Ile His Lys Gly Phe Asp Glu Arg His Ala Tyr
    1190                1195                1200

Ile Gly Gly Met Phe Gly Ala Gly Ile Tyr Phe Ala Glu Asn Ser
    1205                1210                1215

Ser Lys Ser Asn Gln Tyr Val Tyr Gly Ile Gly Gly Gly Thr Gly
    1220                1225                1230

Cys Pro Thr His Lys Asp Arg Ser Cys Tyr Ile Cys His Arg Gln
    1235                1240                1245

Met Leu Phe Cys Arg Val Thr Leu Gly Lys Ser Phe Leu Gln Phe
    1250                1255                1260

Ser Thr Met Lys Met Ala His Ala Pro Pro Gly His His Ser Val
    1265                1270                1275

Ile Gly Arg Pro Ser Val Asn Gly Leu Ala Tyr Ala Glu Tyr Val
    1280                1285                1290

Ile Tyr Arg Gly Glu Gln Ala Tyr Pro Glu Tyr Leu Ile Thr Tyr
    1295                1300                1305

Gln Ile Met Lys Pro Glu Ala Pro Ser Gln Thr Ala Thr Ala Ala
    1310                1315                1320

Glu Gln Lys Thr
    1325

<210> SEQ ID NO 18
<211> LENGTH: 1166
<212> TYPE: PRT
<213> ORGANISM: Homo sapiens

<400> SEQUENCE: 18

Met Ser Gly Arg Arg Cys Ala Gly Gly Ala Ala Cys Ala Ser Ala
1               5                   10                  15

Ala Ala Glu Ala Val Glu Pro Ala Ala Arg Glu Leu Phe Glu Ala Cys
            20                  25                  30

Arg Asn Gly Asp Val Glu Arg Val Lys Arg Leu Val Thr Pro Glu Lys
        35                  40                  45

Val Asn Ser Arg Asp Thr Ala Gly Arg Lys Ser Thr Pro Leu His Phe
    50                  55                  60

Ala Ala Gly Phe Gly Arg Lys Asp Val Val Glu Tyr Leu Leu Gln Asn
65                  70                  75                  80
```

```
Gly Ala Asn Val Gln Ala Arg Asp Asp Gly Leu Ile Pro Leu His
                85                  90                  95

Asn Ala Cys Ser Phe Gly His Ala Glu Val Val Asn Leu Leu Leu Arg
            100                 105                 110

His Gly Ala Asp Pro Asn Ala Arg Asp Asn Trp Asn Tyr Thr Pro Leu
            115                 120                 125

His Glu Ala Ala Ile Lys Gly Lys Ile Asp Val Cys Ile Val Leu Leu
            130                 135                 140

Gln His Gly Ala Glu Pro Thr Ile Arg Asn Thr Asp Gly Arg Thr Ala
145                 150                 155                 160

Leu Asp Leu Ala Asp Pro Ser Ala Lys Ala Val Leu Thr Gly Glu Tyr
                165                 170                 175

Lys Lys Asp Glu Leu Leu Glu Ser Ala Arg Ser Gly Asn Glu Glu Lys
            180                 185                 190

Met Met Ala Leu Leu Thr Pro Leu Asn Val Asn Cys His Ala Ser Asp
            195                 200                 205

Gly Arg Lys Ser Thr Pro Leu His Leu Ala Ala Gly Tyr Asn Arg Val
            210                 215                 220

Lys Ile Val Gln Leu Leu Leu Gln His Gly Ala Asp Val His Ala Lys
225                 230                 235                 240

Asp Lys Gly Asp Leu Val Pro Leu His Asn Ala Cys Ser Tyr Gly His
                245                 250                 255

Tyr Glu Val Thr Glu Leu Leu Val Lys His Gly Ala Cys Val Asn Ala
            260                 265                 270

Met Asp Leu Trp Gln Phe Thr Pro Leu His Glu Ala Ala Ser Lys Asn
            275                 280                 285

Arg Val Glu Val Cys Ser Leu Leu Leu Ser Tyr Gly Ala Asp Pro Thr
            290                 295                 300

Leu Leu Asn Cys His Asn Lys Ser Ala Ile Asp Leu Ala Pro Thr Pro
305                 310                 315                 320

Gln Leu Lys Glu Arg Leu Ala Tyr Glu Phe Lys Gly His Ser Leu Leu
            325                 330                 335

Gln Ala Ala Arg Glu Ala Asp Val Thr Arg Ile Lys Lys His Leu Ser
            340                 345                 350

Leu Glu Met Val Asn Phe Lys His Pro Gln Thr His Glu Thr Ala Leu
            355                 360                 365

His Cys Ala Ala Ala Ser Pro Tyr Pro Lys Arg Lys Gln Ile Cys Glu
            370                 375                 380

Leu Leu Leu Arg Lys Gly Ala Asn Ile Asn Glu Lys Thr Lys Glu Phe
385                 390                 395                 400

Leu Thr Pro Leu His Val Ala Ser Glu Lys Ala His Asn Asp Val Val
                405                 410                 415

Glu Val Val Lys His Glu Ala Lys Val Asn Ala Leu Asp Asn Leu
            420                 425                 430

Gly Gln Thr Ser Leu His Arg Ala Ala Tyr Cys Gly His Leu Gln Thr
            435                 440                 445

Cys Arg Leu Leu Leu Ser Tyr Gly Cys Asp Pro Asn Ile Ile Ser Leu
450                 455                 460

Gln Gly Phe Thr Ala Leu Gln Met Gly Asn Glu Asn Val Gln Gln Leu
465                 470                 475                 480

Leu Gln Glu Gly Ile Ser Leu Gly Asn Ser Glu Ala Asp Arg Gln Leu
                485                 490                 495

Leu Glu Ala Ala Lys Ala Gly Asp Val Glu Thr Val Lys Lys Leu Cys
```

```
                    500                 505                 510
Thr Val Gln Ser Val Asn Cys Arg Asp Ile Glu Gly Arg Gln Ser Thr
            515                 520                 525
Pro Leu His Phe Ala Ala Gly Tyr Asn Arg Val Ser Val Glu Tyr
            530                 535                 540
Leu Leu Gln His Gly Ala Asp Val His Ala Lys Asp Lys Gly Gly Leu
545                 550                 555                 560
Val Pro Leu His Asn Ala Cys Ser Tyr Gly His Tyr Glu Val Ala Glu
                565                 570                 575
Leu Leu Val Lys His Gly Ala Val Val Asn Val Ala Asp Leu Trp Lys
                580                 585                 590
Phe Thr Pro Leu His Glu Ala Ala Lys Gly Lys Tyr Glu Ile Cys
            595                 600                 605
Lys Leu Leu Leu Gln His Gly Ala Asp Pro Thr Lys Lys Asn Arg Asp
            610                 615                 620
Gly Asn Thr Pro Leu Asp Leu Val Lys Asp Gly Asp Thr Asp Ile Gln
625                 630                 635                 640
Asp Leu Leu Arg Gly Asp Ala Ala Leu Leu Asp Ala Ala Lys Lys Gly
                645                 650                 655
Cys Leu Ala Arg Val Lys Lys Leu Ser Ser Pro Asp Asn Val Asn Cys
                660                 665                 670
Arg Asp Thr Gln Gly Arg His Ser Thr Pro Leu His Leu Ala Ala Gly
            675                 680                 685
Tyr Asn Asn Leu Glu Val Ala Glu Tyr Leu Leu Gln His Gly Ala Asp
            690                 695                 700
Val Asn Ala Gln Asp Lys Gly Gly Leu Ile Pro Leu His Asn Ala Ala
705                 710                 715                 720
Ser Tyr Gly His Val Asp Val Ala Ala Leu Leu Ile Lys Tyr Asn Ala
                725                 730                 735
Cys Val Asn Ala Thr Asp Lys Trp Ala Phe Thr Pro Leu His Glu Ala
                740                 745                 750
Ala Gln Lys Gly Arg Thr Gln Leu Cys Ala Leu Leu Leu Ala His Gly
            755                 760                 765
Ala Asp Pro Thr Leu Lys Asn Gln Glu Gly Gln Thr Pro Leu Asp Leu
            770                 775                 780
Val Ser Ala Asp Asp Val Ser Ala Leu Leu Thr Ala Ala Met Pro Pro
785                 790                 795                 800
Ser Ala Leu Pro Ser Cys Tyr Lys Pro Gln Val Leu Asn Gly Val Arg
                805                 810                 815
Ser Pro Gly Ala Thr Ala Asp Ala Leu Ser Ser Gly Pro Ser Ser Pro
            820                 825                 830
Ser Ser Leu Ser Ala Ala Ser Ser Leu Asp Asn Leu Ser Gly Ser Phe
            835                 840                 845
Ser Glu Leu Ser Ser Val Val Ser Ser Ser Gly Thr Glu Gly Ala Ser
            850                 855                 860
Ser Leu Glu Lys Lys Glu Val Pro Gly Val Asp Phe Ser Ile Thr Gln
865                 870                 875                 880
Phe Val Arg Asn Leu Gly Leu Glu His Leu Met Asp Ile Phe Glu Arg
                885                 890                 895
Glu Gln Ile Thr Leu Asp Val Leu Val Glu Met Gly His Lys Glu Leu
            900                 905                 910
Lys Glu Ile Gly Ile Asn Ala Tyr Gly His Arg His Lys Leu Ile Lys
            915                 920                 925
```

Gly Val Glu Arg Leu Ile Ser Gly Gln Gln Gly Leu Asn Pro Tyr Leu
    930             935             940

Thr Leu Asn Thr Ser Gly Ser Gly Thr Ile Leu Ile Asp Leu Ser Pro
945             950             955             960

Asp Asp Lys Glu Phe Gln Ser Val Glu Glu Met Gln Ser Thr Val
                965             970             975

Arg Glu His Arg Asp Gly Gly His Ala Gly Gly Ile Phe Asn Arg Tyr
            980             985             990

Asn Ile Leu Lys Ile Gln Lys Val Cys Asn Lys Lys Leu Trp Glu Arg
        995             1000            1005

Tyr Thr His Arg Arg Lys Glu Val Ser Glu Glu Asn His Asn His
    1010            1015            1020

Ala Asn Glu Arg Met Leu Phe His Gly Ser Pro Phe Val Asn Ala
    1025            1030            1035

Ile Ile His Lys Gly Phe Asp Glu Arg His Ala Tyr Ile Gly Gly
    1040            1045            1050

Met Phe Gly Ala Gly Ile Tyr Phe Ala Glu Asn Ser Ser Lys Ser
    1055            1060            1065

Asn Gln Tyr Val Tyr Gly Ile Gly Gly Gly Thr Gly Cys Pro Val
    1070            1075            1080

His Lys Asp Arg Ser Cys Tyr Ile Cys His Arg Gln Leu Leu Phe
    1085            1090            1095

Cys Arg Val Thr Leu Gly Lys Ser Phe Leu Gln Phe Ser Ala Met
    1100            1105            1110

Lys Met Ala His Ser Pro Pro Gly His His Ser Val Thr Gly Arg
    1115            1120            1125

Pro Ser Val Asn Gly Leu Ala Leu Ala Glu Tyr Val Ile Tyr Arg
    1130            1135            1140

Gly Glu Gln Ala Tyr Pro Glu Tyr Leu Ile Thr Tyr Gln Ile Met
    1145            1150            1155

Arg Pro Glu Gly Met Val Asp Gly
    1160            1165

<210> SEQ ID NO 19
<211> LENGTH: 630
<212> TYPE: PRT
<213> ORGANISM: Homo sapiens

<400> SEQUENCE: 19

Met Asp Ile Lys Gly Gln Phe Trp Asn Asp Asp Ser Glu Gly Asp
1               5               10              15

Asn Glu Ser Glu Glu Phe Leu Tyr Gly Val Gln Gly Ser Cys Ala Ala
                20              25              30

Asp Leu Tyr Arg His Pro Gln Leu Asp Ala Asp Ile Glu Ala Val Lys
        35              40              45

Glu Ile Tyr Ser Glu Asn Ser Val Ser Ile Arg Glu Tyr Gly Thr Ile
    50              55              60

Asp Asp Val Asp Ile Asp Leu His Ile Asn Ile Ser Phe Leu Asp Glu
65              70              75              80

Glu Val Ser Thr Ala Trp Lys Val Leu Arg Thr Glu Pro Ile Val Leu
                85              90              95

Arg Leu Arg Phe Ser Leu Ser Gln Tyr Leu Asp Gly Pro Glu Pro Ser
            100             105             110

Ile Glu Val Phe Gln Pro Ser Asn Lys Glu Gly Phe Gly Leu Gly Leu

-continued

```
           115                 120                 125
Gln Leu Lys Lys Ile Leu Gly Met Phe Thr Ser Gln Gln Trp Lys His
           130                 135                 140
Leu Ser Asn Asp Phe Leu Lys Thr Gln Gln Glu Lys Arg His Ser Trp
145                 150                 155                 160
Phe Lys Ala Ser Gly Thr Ile Lys Lys Phe Arg Ala Gly Leu Ser Ile
                    165                 170                 175
Phe Ser Pro Ile Pro Lys Ser Pro Ser Phe Pro Ile Ile Gln Asp Ser
                    180                 185                 190
Met Leu Lys Gly Lys Leu Gly Val Pro Glu Leu Arg Val Gly Arg Leu
                    195                 200                 205
Met Asn Arg Ser Ile Ser Cys Thr Met Lys Asn Pro Lys Val Glu Val
           210                 215                 220
Phe Gly Tyr Pro Pro Ser Pro Gln Ala Gly Leu Leu Cys Pro Gln His
225                 230                 235                 240
Val Gly Leu Pro Pro Ala Arg Thr Ser Pro Leu Val Ser Gly His
                    245                 250                 255
Cys Lys Asn Ile Pro Thr Leu Glu Tyr Gly Phe Leu Val Gln Ile Met
                    260                 265                 270
Lys Tyr Ala Glu Gln Arg Ile Pro Thr Leu Asn Glu Tyr Cys Val Val
           275                 280                 285
Cys Asp Glu Gln His Val Phe Gln Asn Gly Ser Met Leu Lys Pro Ala
           290                 295                 300
Val Cys Thr Arg Glu Leu Cys Val Phe Ser Phe Tyr Thr Leu Gly Val
305                 310                 315                 320
Met Ser Gly Ala Ala Glu Val Ala Thr Gly Ala Glu Val Val Asp
                    325                 330                 335
Leu Leu Val Ala Met Cys Arg Ala Ala Leu Glu Ser Pro Arg Lys Ser
                    340                 345                 350
Ile Ile Phe Glu Pro Tyr Pro Ser Val Val Asp Pro Thr Asp Pro Lys
           355                 360                 365
Thr Leu Ala Phe Asn Pro Lys Lys Lys Asn Tyr Glu Arg Leu Gln Lys
           370                 375                 380
Ala Leu Asp Ser Val Met Ser Ile Arg Glu Met Thr Gln Gly Ser Tyr
385                 390                 395                 400
Leu Glu Ile Lys Lys Gln Met Asp Lys Leu Asp Pro Leu Ala His Pro
                    405                 410                 415
Leu Leu Gln Trp Ile Ile Ser Ser Asn Arg Ser His Ile Val Lys Leu
                    420                 425                 430
Pro Leu Ser Arg Leu Lys Phe Met His Thr Ser His Gln Phe Leu Leu
           435                 440                 445
Leu Ser Ser Pro Pro Ala Lys Glu Ala Arg Phe Arg Thr Ala Lys Lys
           450                 455                 460
Leu Tyr Gly Ser Thr Phe Ala Phe His Gly Ser His Ile Glu Asn Trp
465                 470                 475                 480
His Ser Ile Leu Arg Asn Gly Leu Val Asn Ala Ser Tyr Thr Lys Leu
                    485                 490                 495
Gln Leu His Gly Ala Ala Tyr Gly Lys Gly Ile Tyr Leu Ser Pro Ile
                    500                 505                 510
Ser Ser Ile Ser Phe Gly Tyr Ser Gly Met Gly Lys Gly Gln His Arg
                    515                 520                 525
Met Pro Ser Lys Asp Glu Leu Val Gln Arg Tyr Asn Arg Met Asn Thr
           530                 535                 540
```

```
Ile Pro Gln Thr Arg Ser Ile Gln Ser Arg Phe Leu Gln Ser Arg Asn
545                 550                 555                 560

Leu Asn Cys Ile Ala Leu Cys Glu Val Ile Thr Ser Lys Asp Leu Gln
            565                 570                 575

Lys His Gly Asn Ile Trp Val Cys Pro Val Ser Asp His Val Cys Thr
        580                 585                 590

Arg Phe Phe Phe Val Tyr Glu Asp Gly Gln Val Gly Asp Ala Asn Ile
    595                 600                 605

Asn Thr Gln Asp Pro Lys Ile Gln Lys Glu Ile Met Arg Val Ile Gly
610                 615                 620

Thr Gln Val Tyr Thr Asn
625                 630

<210> SEQ ID NO 20
<211> LENGTH: 494
<212> TYPE: PRT
<213> ORGANISM: Homo sapiens

<400> SEQUENCE: 20

Met Gln Thr Phe Val Thr Gln Gln Trp Lys Gln Ser Lys Glu Lys Ser
1               5                   10                  15

Asn Cys Leu His Asn Lys Lys Leu Ser Glu Lys Lys Val Lys Ser Pro
            20                  25                  30

Leu His Leu Phe Ser Thr Leu Arg Arg Ser Pro Ser Tyr Pro Pro Pro
        35                  40                  45

Gly Cys Gly Lys Ser Lys Ser Lys Leu Lys Ser Glu Gln Asp Gly Ile
50                  55                  60

Ser Lys Thr His Lys Leu Leu Arg Arg Thr Cys Ser Ser Thr Val Lys
65                  70                  75                  80

Thr Asp Asp Val Cys Val Thr Lys Ser His Arg Thr Phe Gly Arg Ser
                85                  90                  95

Leu Ser Ser Asp Pro Arg Ala Glu Gln Ala Met Thr Ala Ile Lys Ser
            100                 105                 110

His Lys Leu Leu Asn Arg Pro Cys Pro Ala Ala Val Lys Ser Glu Glu
        115                 120                 125

Cys Leu Thr Leu Lys Ser His Arg Leu Leu Thr Arg Ser Cys Ser Gly
130                 135                 140

Asp Pro Arg Cys Glu His Asn Thr Asn Leu Lys Pro His Lys Leu Leu
145                 150                 155                 160

Ser Arg Ser Tyr Ser Ser Asn Leu Arg Met Glu Glu Leu Tyr Gly Leu
                165                 170                 175

Lys Asn His Lys Leu Leu Ser Lys Ser Tyr Ser Ser Ala Pro Lys Ser
            180                 185                 190

Ser Lys Thr Glu Leu Phe Lys Glu Pro Asn Ala Glu Gly Arg Arg Leu
        195                 200                 205

Ser Leu Thr Ser Gly Leu Ile Gly Ile Leu Thr Pro Ser Ser Ser Ser
210                 215                 220

Ser Ser Gln Leu Ala Pro Asn Gly Ala Lys Cys Ile Pro Val Arg Asp
225                 230                 235                 240

Arg Gly Phe Leu Val Gln Thr Ile Glu Phe Ala Glu Gln Arg Ile Pro
                245                 250                 255

Val Leu Asn Glu Tyr Cys Val Val Cys Asp Glu Pro His Val Phe Gln
            260                 265                 270

Asn Gly Pro Met Leu Arg Pro Thr Val Cys Glu Arg Glu Leu Cys Val
```

```
                275                 280                 285
Phe Ala Phe Gln Thr Leu Gly Val Met Asn Glu Ala Ala Asp Glu Ile
290                 295                 300
Ala Thr Gly Ala Gln Lys Lys Asn Tyr Asp Arg Val Met Lys Ala Leu
305                 310                 315                 320
Asp Ser Ile Thr Ser Ile Arg Glu Met Thr Gln Ala Pro Tyr Leu Glu
                325                 330                 335
Ile Lys Lys Gln Met Asp Lys Gln Asp Pro Leu Ala His Pro Leu Leu
                340                 345                 350
Gln Trp Val Ile Ser Ser Asn Arg Ser His Ile Val Lys Leu Pro Val
                355                 360                 365
Asn Arg Gln Leu Lys Phe Met His Thr Pro His Gln Phe Leu Leu Leu
370                 375                 380
Ser Ser Pro Pro Ala Lys Glu Ser Asn Phe Arg Ala Ala Lys Lys Leu
385                 390                 395                 400
Phe Gly Ser Thr Phe Ala Phe His Gly Ser His Ile Glu Asn Trp His
                405                 410                 415
Ser Ile Leu Arg Asn Gly Leu Val Val Ala Ser Asn Thr Arg Leu Gln
                420                 425                 430
Leu His Gly Ala Met Tyr Gly Ser Gly Ile Tyr Leu Ser Pro Met Ser
                435                 440                 445
Ser Ile Ser Phe Gly Tyr Ser Gly Met Asn Lys Lys Gln Lys Val Ser
                450                 455                 460
Ala Lys Asp Glu Pro Ala Ser Ser Lys Ser Ser Asn Thr Ser Gln
465                 470                 475                 480
Ser Gln Lys Lys Arg Thr Ala Ile Pro Ile Pro Ala Lys Pro
                485                 490

<210> SEQ ID NO 21
<211> LENGTH: 819
<212> TYPE: PRT
<213> ORGANISM: Homo sapiens

<400> SEQUENCE: 21

Met Asp Phe Ser Met Val Ala Gly Ala Ala Ala Tyr Asn Glu Lys Ser
1               5                   10                  15
Glu Thr Gly Ala Leu Gly Glu Asn Tyr Ser Trp Gln Ile Pro Ile Asn
                20                  25                  30
His Asn Asp Phe Lys Ile Leu Lys Asn Asn Glu Arg Gln Leu Cys Glu
                35                  40                  45
Val Leu Gln Asn Lys Phe Gly Cys Ile Ser Thr Leu Val Ser Pro Val
                50                  55                  60
Gln Glu Gly Asn Ser Lys Ser Leu Gln Val Phe Arg Lys Met Leu Thr
65                  70                  75                  80
Pro Arg Ile Glu Leu Ser Val Trp Lys Asp Asp Leu Thr Thr His Ala
                85                  90                  95
Val Asp Ala Val Val Asn Ala Ala Asn Glu Asp Leu Leu His Gly Gly
                100                 105                 110
Gly Leu Ala Leu Ala Leu Val Lys Ala Gly Gly Phe Glu Ile Gln Glu
                115                 120                 125
Glu Ser Lys Gln Phe Val Ala Arg Tyr Gly Lys Val Ser Ala Gly Glu
                130                 135                 140
Ile Ala Val Thr Gly Ala Gly Arg Leu Pro Cys Lys Gln Ile Ile His
145                 150                 155                 160
```

-continued

Ala Val Gly Pro Arg Trp Met Glu Trp Asp Lys Gln Gly Cys Thr Gly
            165                 170                 175

Lys Leu Gln Arg Ala Ile Val Ser Ile Leu Asn Tyr Val Ile Tyr Lys
        180                 185                 190

Asn Thr His Ile Lys Thr Val Ala Ile Pro Ala Leu Ser Ser Gly Ile
        195                 200                 205

Phe Gln Phe Pro Leu Asn Leu Cys Thr Lys Thr Ile Val Glu Thr Ile
    210                 215                 220

Arg Val Ser Leu Gln Gly Lys Pro Met Met Ser Asn Leu Lys Glu Ile
225                 230                 235                 240

His Leu Val Ser Asn Glu Asp Pro Thr Val Ala Ala Phe Lys Ala Ala
            245                 250                 255

Ser Glu Phe Ile Leu Gly Lys Ser Glu Leu Gly Gln Glu Thr Thr Pro
            260                 265                 270

Ser Phe Asn Ala Met Val Val Asn Asn Leu Thr Leu Gln Ile Val Gln
        275                 280                 285

Gly His Ile Glu Trp Gln Thr Ala Asp Val Ile Val Asn Ser Val Asn
    290                 295                 300

Pro His Asp Ile Thr Val Gly Pro Val Ala Lys Ser Ile Leu Gln Gln
305                 310                 315                 320

Ala Gly Val Glu Met Lys Ser Glu Phe Leu Ala Thr Lys Ala Lys Gln
            325                 330                 335

Phe Gln Arg Ser Gln Leu Val Leu Val Thr Lys Gly Phe Asn Leu Phe
            340                 345                 350

Cys Lys Tyr Ile Tyr His Val Leu Trp His Ser Glu Phe Pro Lys Pro
        355                 360                 365

Gln Ile Leu Lys His Ala Met Lys Glu Cys Leu Glu Lys Cys Ile Glu
    370                 375                 380

Gln Asn Ile Thr Ser Ile Ser Phe Pro Ala Leu Gly Thr Gly Asn Met
385                 390                 395                 400

Glu Ile Lys Lys Glu Thr Ala Ala Glu Ile Leu Phe Asp Glu Val Leu
            405                 410                 415

Thr Phe Ala Lys Asp His Val Lys His Gln Leu Thr Val Lys Phe Val
            420                 425                 430

Ile Phe Pro Thr Asp Leu Glu Ile Tyr Lys Ala Phe Ser Ser Glu Met
        435                 440                 445

Ala Lys Arg Ser Lys Met Leu Ser Leu Asn Asn Tyr Ser Val Pro Gln
    450                 455                 460

Ser Thr Arg Glu Glu Lys Arg Glu Asn Gly Leu Glu Ala Arg Ser Pro
465                 470                 475                 480

Ala Ile Asn Leu Met Gly Phe Asn Val Glu Glu Met Tyr Glu Ala His
            485                 490                 495

Ala Trp Ile Gln Arg Ile Leu Ser Leu Gln Asn His His Ile Ile Glu
            500                 505                 510

Asn Asn His Ile Leu Tyr Leu Gly Arg Lys Glu His Asp Ile Leu Ser
        515                 520                 525

Gln Leu Gln Lys Thr Ser Ser Val Ser Ile Thr Glu Ile Ile Ser Pro
    530                 535                 540

Gly Arg Thr Glu Leu Glu Ile Glu Gly Ala Arg Ala Asp Leu Ile Glu
545                 550                 555                 560

Val Val Met Asn Ile Glu Asp Met Leu Cys Lys Val Gln Glu Glu Met
            565                 570                 575

Ala Arg Lys Lys Glu Arg Gly Leu Trp Arg Ser Leu Gly Gln Trp Thr

```
                      580              585                 590
Ile Gln Gln Gln Lys Thr Gln Asp Glu Met Lys Glu Asn Ile Ile Phe
                595                 600                 605

Leu Lys Cys Pro Val Pro Thr Gln Glu Leu Leu Asp Gln Lys Lys
            610                 615                 620

Gln Phe Glu Lys Cys Gly Leu Gln Val Leu Lys Val Glu Lys Ile Asp
625                 630                 635                 640

Asn Glu Val Leu Met Ala Ala Phe Gln Arg Lys Lys Met Met Glu
                645                 650                 655

Glu Lys Leu His Arg Gln Pro Val Ser His Arg Leu Phe Gln Gln Val
                660                 665                 670

Pro Tyr Gln Phe Cys Asn Val Val Cys Arg Val Gly Phe Gln Arg Met
            675                 680                 685

Tyr Ser Thr Pro Cys Asp Pro Lys Tyr Gly Ala Gly Ile Tyr Phe Thr
            690                 695                 700

Lys Asn Leu Lys Asn Leu Ala Glu Lys Ala Lys Lys Ile Ser Ala Ala
705                 710                 715                 720

Asp Lys Leu Ile Tyr Val Phe Glu Ala Glu Val Leu Thr Gly Phe Phe
                725                 730                 735

Cys Gln Gly His Pro Leu Asn Ile Val Pro Pro Leu Ser Pro Gly
            740                 745                 750

Ala Ile Asp Gly His Asp Ser Val Val Asp Asn Val Ser Ser Pro Glu
            755                 760                 765

Thr Phe Val Ile Phe Ser Gly Met Gln Ala Ile Pro Gln Tyr Leu Trp
            770                 775                 780

Thr Cys Thr Gln Glu Tyr Val Gln Ser Gln Asp Tyr Ser Ser Gly Pro
785                 790                 795                 800

Met Arg Pro Phe Ala Gln His Pro Trp Arg Gly Phe Ala Ser Gly Ser
                805                 810                 815

Pro Val Asp

<210> SEQ ID NO 22
<211> LENGTH: 338
<212> TYPE: PRT
<213> ORGANISM: Homo sapiens

<400> SEQUENCE: 22

Met Trp Glu Ala Asn Pro Glu Met Phe His Lys Ala Glu Glu Leu Phe
1               5                   10                  15

Ser Lys Thr Thr Asn Asn Glu Val Asp Asp Met Asp Thr Ser Asp Thr
                20                  25                  30

Gln Trp Gly Trp Phe Tyr Leu Ala Glu Cys Gly Lys Trp His Met Phe
            35                  40                  45

Gln Pro Asp Thr Asn Ser Gln Cys Ser Val Ser Ser Glu Asp Ile Glu
        50                  55                  60

Lys Ser Phe Lys Thr Asn Pro Cys Gly Ser Ile Ser Phe Thr Thr Ser
65                  70                  75                  80

Lys Phe Ser Tyr Lys Ile Asp Phe Ala Glu Met Lys Gln Met Asn Leu
                85                  90                  95

Thr Thr Gly Lys Gln Arg Leu Ile Lys Arg Ala Pro Phe Ser Ile Ser
            100                 105                 110

Ala Phe Ser Tyr Ile Cys Glu Asn Glu Ala Ile Pro Met Pro Pro His
        115                 120                 125

Trp Glu Asn Val Asn Thr Gln Val Pro Tyr Gln Leu Ile Pro Leu His
```

```
                130             135             140
Asn Gln Thr His Glu Tyr Asn Glu Val Ala Asn Leu Phe Gly Lys Thr
145                 150                 155                 160

Met Asp Arg Asn Arg Ile Lys Arg Ile Gln Arg Ile Gln Asn Leu Asp
                165                 170                 175

Leu Trp Glu Phe Phe Cys Arg Lys Lys Ala Gln Leu Lys Lys Lys Arg
            180                 185                 190

Gly Val Pro Gln Ile Asn Glu Gln Met Leu Phe His Gly Thr Ser Ser
        195                 200                 205

Glu Phe Val Glu Ala Ile Cys Ile His Asn Phe Asp Trp Arg Ile Asn
210                 215                 220

Gly Ile His Gly Ala Val Phe Gly Lys Gly Thr Tyr Phe Ala Arg Asp
225                 230                 235                 240

Ala Ala Tyr Ser Ser Arg Phe Cys Lys Asp Asp Ile Lys His Gly Asn
                245                 250                 255

Thr Phe Gln Ile His Gly Val Ser Leu Gln Gln Arg His Leu Phe Arg
            260                 265                 270

Thr Tyr Lys Ser Met Phe Leu Ala Arg Val Leu Ile Gly Asp Tyr Ile
        275                 280                 285

Asn Gly Asp Ser Lys Tyr Met Arg Pro Pro Ser Lys Asp Gly Ser Tyr
290                 295                 300

Val Asn Leu Tyr Asp Ser Cys Val Asp Asp Thr Trp Asn Pro Lys Ile
305                 310                 315                 320

Phe Val Val Phe Asp Ala Asn Gln Ile Tyr Pro Glu Tyr Leu Ile Asp
                325                 330                 335

Phe His

<210> SEQ ID NO 23
<211> LENGTH: 902
<212> TYPE: PRT
<213> ORGANISM: Homo sapiens

<400> SEQUENCE: 23

Met Ala Asp Pro Glu Val Cys Cys Phe Ile Thr Lys Ile Leu Cys Ala
1               5                   10                  15

His Gly Gly Arg Met Ala Leu Asp Ala Leu Leu Gln Glu Ile Ala Leu
            20                  25                  30

Ser Glu Pro Gln Leu Cys Glu Val Leu Gln Val Ala Gly Pro Asp Arg
        35                  40                  45

Phe Val Val Leu Glu Thr Gly Gly Glu Ala Gly Ile Thr Arg Ser Val
    50                  55                  60

Val Ala Thr Thr Arg Ala Arg Val Cys Arg Arg Lys Tyr Cys Gln Arg
65                  70                  75                  80

Pro Cys Asp Asn Leu His Leu Cys Lys Leu Asn Leu Gly Arg Cys
                85                  90                  95

Asn Tyr Ser Gln Ser Glu Arg Asn Leu Cys Lys Tyr Ser His Glu Val
                100                 105                 110

Leu Ser Glu Glu Asn Phe Lys Val Leu Lys Asn His Glu Leu Ser Gly
            115                 120                 125

Leu Asn Lys Glu Glu Leu Ala Val Leu Leu Gln Ser Asp Pro Phe
        130                 135                 140

Phe Met Pro Glu Ile Cys Lys Ser Tyr Lys Gly Glu Gly Arg Gln Gln
145                 150                 155                 160

Ile Cys Asn Gln Gln Pro Pro Cys Ser Arg Leu His Ile Cys Asp His
```

```
                  165                 170                 175
Phe Thr Arg Gly Asn Cys Arg Phe Pro Asn Cys Leu Arg Ser His Asn
                180                 185                 190

Leu Met Asp Arg Lys Val Leu Ala Ile Met Arg Glu His Gly Leu Asn
                195                 200                 205

Pro Asp Val Val Gln Asn Ile Gln Asp Ile Cys Asn Ser Lys His Met
210                 215                 220

Gln Lys Asn Pro Pro Gly Pro Arg Ala Pro Ser Ser His Arg Arg Asn
225                 230                 235                 240

Met Ala Tyr Arg Ala Arg Ser Lys Ser Arg Asp Arg Phe Phe Gln Gly
                245                 250                 255

Ser Gln Glu Phe Leu Ala Ser Ala Ser Ala Ser Ala Glu Arg Ser Cys
                260                 265                 270

Thr Pro Ser Pro Asp Gln Ile Ser His Arg Ala Ser Leu Glu Asp Ala
                275                 280                 285

Pro Val Asp Asp Leu Thr Arg Lys Phe Thr Tyr Leu Gly Ser Gln Asp
                290                 295                 300

Arg Ala Arg Pro Pro Ser Gly Ser Ser Lys Ala Thr Asp Leu Gly Gly
305                 310                 315                 320

Thr Ser Gln Ala Gly Thr Ser Gln Arg Phe Leu Glu Asn Gly Ser Gln
                325                 330                 335

Glu Asp Leu Leu His Gly Asn Pro Gly Ser Thr Tyr Leu Ala Ser Asn
                340                 345                 350

Ser Thr Ser Ala Pro Asn Trp Lys Ser Leu Thr Ser Trp Thr Asn Asp
                355                 360                 365

Gln Gly Ala Arg Arg Lys Thr Val Phe Ser Pro Thr Leu Pro Ala Ala
                370                 375                 380

Arg Ser Ser Leu Gly Ser Leu Gln Thr Pro Glu Ala Val Thr Thr Arg
385                 390                 395                 400

Lys Gly Thr Gly Leu Leu Ser Ser Asp Tyr Arg Ile Ile Asn Gly Lys
                405                 410                 415

Ser Gly Thr Gln Asp Ile Gln Pro Gly Pro Leu Phe Asn Asn Asn Ala
                420                 425                 430

Asp Gly Val Ala Thr Asp Ile Thr Ser Thr Arg Ser Leu Asn Tyr Lys
                435                 440                 445

Ser Thr Ser Ser Gly His Arg Glu Ile Ser Ser Pro Arg Ile Gln Asp
450                 455                 460

Ala Gly Pro Ala Ser Arg Asp Val Gln Ala Thr Gly Arg Ile Ala Asp
465                 470                 475                 480

Asp Ala Asp Pro Arg Val Ala Leu Val Asn Asp Ser Leu Ser Asp Val
                485                 490                 495

Thr Ser Thr Thr Ser Ser Arg Val Asp Asp His Asp Ser Glu Glu Ile
                500                 505                 510

Cys Leu Asp His Leu Cys Lys Gly Cys Pro Leu Asn Gly Ser Cys Ser
                515                 520                 525

Lys Val His Phe His Leu Pro Tyr Arg Trp Gln Met Leu Ile Gly Lys
                530                 535                 540

Thr Trp Thr Asp Phe Glu His Met Glu Thr Ile Glu Lys Gly Tyr Cys
545                 550                 555                 560
```

-continued

```
Asn Pro Gly Ile His Leu Cys Ser Val Gly Ser Tyr Thr Ile Asn Phe
            565                 570                 575
Arg Val Met Ser Cys Asp Ser Phe Pro Ile Arg Arg Leu Ser Thr Pro
            580                 585                 590
Ser Ser Val Thr Lys Pro Ala Asn Ser Val Phe Thr Thr Lys Trp Ile
            595                 600                 605
Trp Tyr Trp Lys Asn Glu Ser Gly Thr Trp Ile Gln Tyr Gly Glu Glu
        610                 615                 620
Lys Asp Lys Arg Lys Asn Ser Asn Val Asp Ser Ser Tyr Leu Glu Ser
625                 630                 635                 640
Leu Tyr Gln Ser Cys Pro Arg Gly Val Val Pro Phe Gln Ala Gly Ser
                645                 650                 655
Arg Asn Tyr Glu Leu Ser Phe Gln Gly Met Ile Gln Thr Asn Ile Ala
                660                 665                 670
Ser Lys Thr Gln Lys Asp Val Ile Arg Arg Pro Thr Phe Val Pro Gln
            675                 680                 685
Trp Tyr Val Gln Gln Met Lys Arg Gly Pro Asp His Gln Pro Ala Lys
        690                 695                 700
Thr Ser Ser Val Ser Leu Thr Ala Thr Phe Arg Pro Gln Glu Asp Phe
705                 710                 715                 720
Cys Phe Leu Ser Ser Lys Lys Tyr Lys Leu Ser Glu Ile His His Leu
                725                 730                 735
His Pro Glu Tyr Val Arg Val Ser Glu His Phe Lys Ala Ser Met Lys
                740                 745                 750
Asn Phe Lys Ile Glu Lys Ile Lys Ile Glu Asn Ser Glu Leu Leu
            755                 760                 765
Asp Lys Phe Thr Trp Lys Lys Ser Gln Met Lys Glu Glu Gly Lys Leu
        770                 775                 780
Leu Phe Tyr Ala Thr Ser Arg Ala Tyr Val Glu Ser Ile Cys Ser Asn
785                 790                 795                 800
Asn Phe Asp Ser Phe Leu His Glu Thr His Glu Asn Lys Tyr Gly Lys
                805                 810                 815
Gly Ile Tyr Phe Ala Lys Asp Ala Ile Tyr Ser His Lys Asn Cys Pro
                820                 825                 830
Tyr Asp Ala Lys Asn Val Val Met Phe Val Ala Gln Val Leu Val Gly
            835                 840                 845
Lys Phe Thr Glu Gly Asn Ile Thr Tyr Thr Ser Pro Pro Pro Gln Phe
        850                 855                 860
Asp Ser Cys Val Asp Thr Arg Ser Asn Pro Ser Val Phe Val Ile Phe
865                 870                 875                 880
Gln Lys Asp Gln Val Tyr Pro Gln Tyr Val Ile Glu Tyr Thr Glu Asp
                885                 890                 895
Lys Ala Cys Val Ile Ser
            900
```

SCREENING METHODS FOR PARP MODULATORS

CLAIM OF PRIORITY

This application claims priority to U.S. Provisional Patent Application Ser. No. 62/664,595, filed on Apr. 30, 2018, the entire contents of which are hereby incorporated by reference.

SEQUENCE LISTING

The present specification is being filed with a computer readable form (CRF) copy of the Sequence Listing. The CRF entitled Sequence_Listing.txt, which was created on Apr. 11, 2019 and is 129,228 bytes in size, is identical to the paper copy of the Sequence Listing and is incorporated herein by reference in its entirety.

TECHNICAL FIELD

The present disclosure is related to methods of identifying Poly(ADP-ribose) polymerase (PARP) inhibitors.

BACKGROUND

Poly(ADP-ribose) polymerases (PARPs) are a family of 17 enzymes that can transfer ADP-ribose from nicotinamide adenine dinucleotide (NAD$^+$) to protein and nucleic acid substrates[1-2]. The PARP enzymes family is comprised of two subfamilies, monoPARPs and polyPARPs. MonoPARP enzymes catalyze the transfer of a single ADP-ribose group to a target amino acid, while polyPARP enzymes catalyze the transfer of multiple ADP-ribose groups to form polymers. While approved drugs that target the polyPARPs exist, there are no potent and selective inhibitors of the monoPARPs. MonoPARPs are important regulators of the immune response[3-4] and are implicated in human diseases such as inflammation[5] and cancer[6-7], therefore small molecules that modulate the enzymatic activity of monoPARPs can be useful therapeutics. Despite interest in the development of monoPARP inhibitors, the field is lacking effective high-throughput assays that can be used to screen for and characterize modulators of monoPARP function. Thus, there is an urgent need for high-throughput assays that can be used to screen monoPARP modulators.

SUMMARY

The present disclosure is related to methods of identifying PARP modulators.

The present invention is directed to a method of identifying an inhibitor for PARPs, the method comprising:
  combining (i) a polypeptide comprising a PARP catalytic domain wherein the polypeptide is labeled with a donor fluorophore, (ii) a PARP probe, wherein the PARP probe is labeled with an acceptor fluorophore, and (iii) a test compound;
  exposing the donor fluorophore to excitation light;
  measuring a signal produced by the acceptor fluorophore; and
  identifying the test compound as an inhibitor for PARP based on the signal produced by the acceptor fluorophore.

The present invention is further directed to a method of identifying an inhibitor for PARPs, the method comprising:
  combining (i) a polypeptide comprising a PARP catalytic domain, wherein the polypeptide is labeled with an acceptor fluorophore; (ii) a PARP probe, wherein the PARP probe is labeled with a donor fluorophore, and (iii) a test compound;
  exposing the donor fluorophore to excitation light;
  measuring a signal produced by the acceptor fluorophore in the presence of a test compound; and
  identifying the test compound as an inhibitor for PARP based on the signal produced by the acceptor fluorophore.

The present invention is further directed to a method of identifying an inhibitor for PARPs, the method comprising:
  contacting a polypeptide comprising a PARP catalytic domain with a PARP probe in the presence of a test compound, wherein the PARP probe comprises a fluorophore;
  exposing the probe to polarized excitation light, thereby generating fluorescence;
  determining a fluorescence polarization value of the fluorescence; and
  identifying the test compound as an inhibitor for PARP based on the fluorescence polarization value of the fluorescence.

The present invention is further directed to a method of identifying an inhibitor for PARPs, the method comprising:
  contacting a fusion polypeptide with a PARP probe that comprises a fluorophore, wherein the fusion polypeptide comprises a PARP catalytic domain and a luciferase enzyme;
  contacting the luciferase enzyme with a substrate to produce light, wherein the light can excite the fluorophore;
  measuring a signal produced by the fluorophore in the presence of a test compound; and
  identifying the test compound as an inhibitor for PARP based on the signal produced by the fluorophore.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 4A-4F. Validation results of the in vitro probe displacement binding assays. Dose response curves for Compound A were generated using each assay to confirm that Probe C was outcompeted from the monoPARP enzyme. $IC_{50}$ values for Compound A were 7 nM (TIPARP), 80 nM (PARP10), 200 nM (PARP12), 50 nM (PARP14), 60 nM (PARP15) and 100 nM (PARP16).

FIGS. 6A-6F show the amino acid sequences of PARPs.

DETAILED DESCRIPTION

Figure 1:
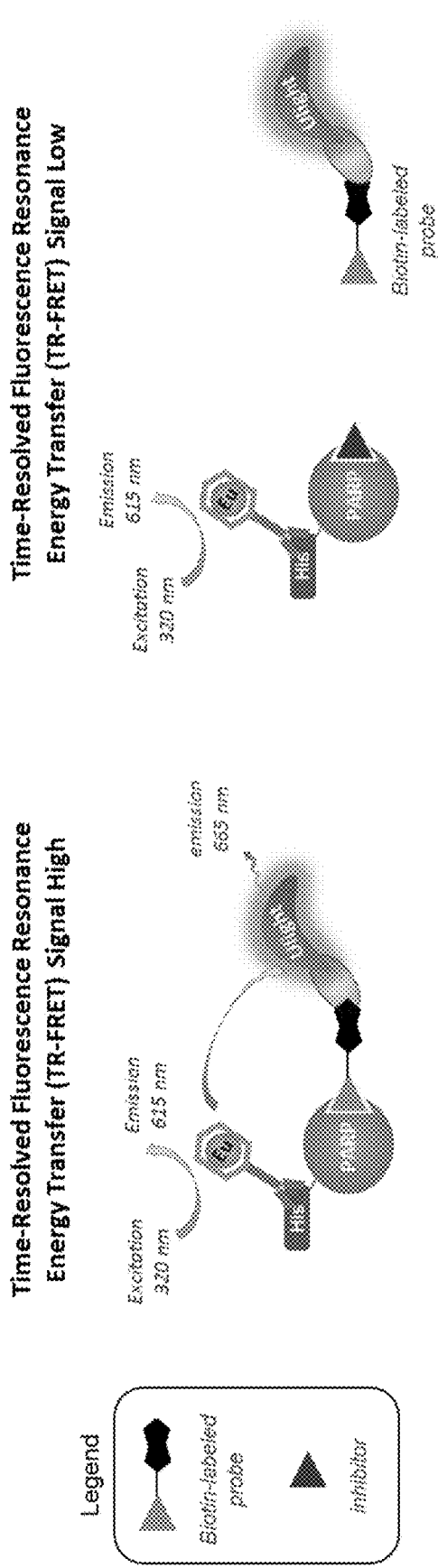
FIG. 1 is a schematic diagram illustrating an example of in vitro TR-FRET probe displacement assay. An inhibitor will outcompete the biotinylated probe and decrease TR-FRET signal.

PARPs refers to a family of proteins involved in a number of cellular processes such as DNA repair, genomic stability, and programmed cell death.

The primary function of PARPs is to post-translationally modify target proteins with ADP-ribose using $NAD^+$ as substrate. The four best-studied family members, PARP1 and PARP5a along with their close functional homologs PARP2 and PARP5b respectively, all generate poly(ADP-ribose) (PAR). The main role of these PARPs is to detect and initiate an immediate cellular response to metabolic, chemical, or radiation-induced single-strand DNA breaks (SSB) by signaling the enzymatic machinery involved in the SSB repair. Once PARP detects a SSB, it binds to the DNA, undergoes a structural change, and begins the synthesis of a polymeric adenosine diphosphate ribose (poly (ADP-ribose)) chain, which acts as a signal for the other DNA-repairing enzymes.

However, many other PARPs do not generate PAR, and instead attach ADP-ribose as a monomer ADP-ribose (MAR) onto target proteins. Recent data has shown that many of these MAR-generating PARPs (monoPARPs) can have cancer relevant functions or inflammation related functions. MonoPARP enzymes have structurally related active sites which bind to nicotinamide adenine dinucleotide ($NAD^+$) and catalyze the transfer of adenosine diphospho-ribose to a substrate amino acid. Enzyme-linked immunosorbent assays (ELISA) measuring the incorporation of biotin-$NAD^+$ to histones or to the monoPARP itself in an automodification reaction have been used to screen for monoPARP modulators[8]. These reactions are not catalytically efficient, and high concentrations of enzyme are needed to generate sufficient turnover to be detected. Since the lowest measurable $IC_{50}$ in an enzyme assay is half of the total enzyme concentration[9], these assays are usually unable to differentiate and rank order very potent compounds. Thermal shift assays (TSA) have also been used to screen inhibitors of monoPARPs[10], however these assays consume large amounts of protein and are at best semi-quantitative since compounds with similar binding affinities can have different effects on protein stabilization[11].

The present disclosure provides a more effective way to identify PARP modulators, and provides a series of high affinity active site probes that bind in the $NAD^+$ pocket of monoPARPs which can be used to develop high-throughput biophysical assays.

Poly (ADP-Ribose) Polymerases

There are 17 PARPs. The enzymatic activity and cancer relevant functions of these PARPs are summarized in Table I below.

TABLE 1

| PARP | Other Names | Activity | NCBI Accession No. | Catalytic Domain | Cancer Related Functions | Cancers to target |
|---|---|---|---|---|---|---|
| PARP1 | ARTD1 | PAR | NP_001609.2 (SEQ ID NO: 13) | Amino acids 788-1014 of accession no. NP_001609.2 | DNA Repair, ERK/NF-kB signaling, Heat shock response | HR deficient Elevated ERK/NF-kB signaling |
| PARP2 | ARTD2 | PAR | NP_005475.2 (SEQ ID NO: 14) | Amino acids 356-583 of accession no. NP_005475.2 | DNA Repair | HR deficient |
| PARP3 | ARTD3 | MAR | NP_001003931.3 (SEQ ID NO: 15) | Amino acids 313-533 of accession no. NP_001003931.3 | DNA Repair | DNA repair deficient |
| PARP4 | vPARP ARTD4 | MAR | NP_006428.2 (SEQ ID NO: 16) | Amino acids 369-573 of accession no. NP_006428.2 | | |
| PARP5a | TNKS1 ARTD5 | PAR | NP_003738.2 (SEQ ID NO: 17) | Amino acids 1112-1317 of accession no. NP_003738.2 | Telomere Maintenance, Wnt Signaling, Proteasome Regulation, Stress Granule Assembly, Cell Division | Elevated Wnt Signaling Telomerase Dependent Stress Granule Positive Solid Tumors |
| PARP5b | TNKS2 ARTD6 | PAR | NP_079511.1 (SEQ ID NO: 18) | Amino acids 959-1164 of accession no. NP_079511.1 | Telomere Maintenance, Wnt Signaling | Elevated Wnt Signaling, Telomerase Dependent |
| PARP6 | ARTD17 | MAR | NP_001310451.1 (SEQ ID NO: 19) | Amino acids 394-620 of accession no. NP_001310451.1 | Negative Regulator of Proliferation | Potential Tumor Suppressive Functions |
| TIPARP | PARP7 ARTD14 | MAR | NP_056323.2 (SEQ ID NO: 1) | Amino acids 449-657 of accession no. NP_056323.2 | | |

TABLE 1-continued

| PARP | Other Names | Activity | NCBI Accession No. | Catalytic Domain | Cancer Related Functions | Cancers to target |
|---|---|---|---|---|---|---|
| PARP8 | ARTD16 | MAR | AAH37386.1 (SEQ ID NO: 20) | Amino acids 328-494 of accession no. AAH37386.1 | | |
| PARP9 | BAL1 ARTD9 | MAR | AAH39580.1 (SEQ ID NO: 21) | Amino acids 628-850 of accession no. AAH39580.1 | Cell Migration | Metastatic Cancers |
| PARP10 | ARTD10 | MAR | NP_116178.2 (SEQ ID NO: 2) | Amino acids 806-1025 of accession no. NP_116178.2 | Inhibits Myc and NF-kB signaling Pro-apoptotic | Potential Tumor Suppressive Functions |
| PARP11 | ARTD11 | MAR | Q9NR21.2 (SEQ ID NO: 22) | Amino acids 123-338 of accession no. Q9NR21.2 | | |
| PARP12 | ARTD12 | MAR | NP_073587.1 (SEQ ID NO: 3) | Amino acids 484-698 of accession no. NP_073587.1 | Stress Granule Assembly | Stress Granule Positive Solid Tumors |
| PARP13 | ZAP ZC3HAV1 ARTD13 | MAR | NP_064504.2 (SEQ ID NO: 23) | Amino acids 716-902 of accession no. NP_064504.2 | Stress Granule Assembly, miRNA-RISC regulation' | Stress Granule Positive Solid Tumors |
| PARP14 | BAL2 ARTD8 | MAR | NP_060024.2 (SEQ ID NO: 4) | Amino acids 1605-1801 of accession no. NP_060024.2 | B cell survival, Cell Migration, Stress Granule Assembly | Hematopoeitic malignancies, Metastatic Cancers |
| PARP15 | BAL3 ARTD7 | MAR | NP_689828.1 (SEQ ID NO: 5) | Amino acids 482-678 of accession no. NP_689828.1 | Stress Granule Assembly | Stress Granule Positive Solid Tumors |
| PARP16 | ARTD15 | MAR | NP_060321.3 (SEQ ID NO: 6) | Amino acids 94-279 of accession no. NP_060321.3 | ER Unfolded Protein Response | UPR dependent |

Among these enzymes, PARP1, PARP2, PARP5a and PARP5b can generate poly (ADP-ribose) (PAR). PARP3, PARP4, PARP6, TIPARP, PARP8, PARP9, PARP10, PARP11, PARP12, PARP13, PARP14, PARP15, and PARP16 are monoPARPs.

PARPs have multiple diverse functions in physiological pathways including cell migration, transcriptional regulation, signal transduction, miRNA-mediated gene silencing, regulation of membrane organelles and telomere length regulation. Additionally, PARPs function in stress-responsive cellular pathways upon DNA damage, cytoplasmic stress, environmental stress and ER stress, activating DNA damage repair, stress granule assembly, the heat shock response and the ER unfolded protein response pathways in response. Many of these physiological and stress response pathways are misregulated in cancer or inflammation.

Thus, the inhibitors of PARPs (e.g., monoPARPs) can have various uses. For example, they can be used to modulate (e.g., inhibit or facilitate) cell migration, transcriptional regulation, signal transduction, and gene silencing. They can also be used to modulate (e.g., inhibit or facilitate) stress-responsive cellular pathways (e.g., upon DNA damage), or DNA damage repair pathways. In some embodiments, PARP inhibitors (e.g., monoPARP inhibitors) can be used to treat a disorder associated with PARP overexpression or overactivity. In some embodiments, PARP inhibitors (e.g., monoPARP inhibitors) can be used to treat cancers or inflammation.

A detailed description of PARPs and their functions can be found, e.g., in Vyas et al., "New PARP targets for cancer therapy," Nature Reviews Cancer 14.7 (2014): 502, which is incorporated herein by reference in its entirety.

The present disclosure provides methods of identifying PARP modulators, and also provides polypeptides (e.g., fusion polypeptides) comprising a catalytic domain of PARPs (e.g., PARP1, PARP2, PARP3, PARP4, PARP5a, PARP5b, PARP6, TIPARP, PARP8, PARP9, PARP10, PARP11, PARP12, PARP13, PARP14, PARP15, or PARP16). These polypeptides can be used in various assays for identifying the modulators of interest (e.g., PARP inhibitors). As used herein, the term "catalytic domain" refers to a portion of an enzyme that has a catalytic activity. The catalytic domain comprises the region of an enzyme that interacts with its substrate to cause the enzymatic reaction. In many cases, the active site is located in the catalytic domain, and the substrate binds to active site.

In some embodiments, the catalytic domain is the catalytic domain of TIPARP (e.g., residues 449-657 of NP_056323.2 (SEQ ID NO: 1)), the catalytic domain of PARP10 (e.g., residues 806-1025 of NP_116178.2 (SEQ ID NO: 2)), the catalytic domain of PARP12 (e.g., residues 484-698 of NP_073587.1 (SEQ ID NO: 3)), the catalytic domain of PARP14 (e.g., residues 1605-1801 of NP_060024.2 (SEQ ID NO: 4)), the catalytic domain of PARP15 (e.g., residues 482-678 of NP_689828.1 (SEQ ID NO: 5)), or the catalytic domain of PARP16 (e.g., residues 5-279 of NP_060321.3 (SEQ ID NO: 6)).

In some embodiments, the catalytic domain is the catalytic domain of PARP1 (e.g., residues 788-1014 of NP_001609.2 (SEQ ID NO: 13)), the catalytic domain of PARP2 (e.g., residues 356-583 of NP_005475.2 (SEQ ID NO: 14)), the catalytic domain of PARP3 (e.g., residues 313-533 of NP_001003931.3 (SEQ ID NO: 15)), the catalytic domain of PARP4 (e.g., residues 369-573 of NP_006428.2 (SEQ ID NO: 16)), the catalytic domain of PARP5a (e.g., residues 1112-1317 of NP_003738.2 (SEQ ID NO: 17)), the catalytic domain of PARP5b (e.g., residues 959-1164 of NP_079511.1 (SEQ ID NO: 18)), the catalytic domain of PARP6 (e.g., residues 394-620 of NP_001310451.1 (SEQ ID NO: 19)), the catalytic domain of PARP8 (e.g., residues 328-494 of AAH37386.1 (SEQ ID NO: 20)), the catalytic domain of PARP9 (e.g., residues 628-850 of AAH39580.1 (SEQ ID NO: 21)), the catalytic domain of PARP11 (e.g., residues 123-338 of Q9NR21.2 (SEQ ID NO: 22)), or the catalytic domain of PARP13 (e.g., residues 716-902 of NP_064504.2 (SEQ ID NO: 23)).

In some embodiments, the polypeptide comprises a catalytic domain that has a sequence that is at least 85%, 90%, 91%, 92%, 93%, 94%, 95%, 96%, 97%, 98%, 99% identical to the sequence of a catalytic domain as described herein.

In some embodiments, the polypeptide (e.g., fusion polypeptide) comprises a region of a PARP, wherein the substrate binding pocket is located in this region of the PARP. In some embodiments, the polypeptide comprises residues 456-657 of NP_056323.2 (SEQ ID NO: 1), residues 808-1025 of NP_116178.2 (SEQ ID NO: 2), residues 489-684 of NP_073587.1 (SEQ ID NO: 3), residues 1611-1801 of NP_060024.2 (SEQ ID NO: 4), residues 481-678 of NP_689828.1 (SEQ ID NO: 5), or residues 5-279 of NP_060321.3 (SEQ ID NO: 6).

In some embodiments, the polypeptide can be linked with a label (e.g., a fluorophore). As used herein, the term "linked" refers to being covalently or non-covalently associated, e.g., by a chemical bond (e.g., a peptide bond, or a carbon-carbon bond), by hydrophobic interaction, by Van der Waals interaction, and/or by electrostatic interaction.

The label can be a chemical or composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA, or luciferase), biotin, enzymes acting on a substrate (e.g., horseradish peroxidase), digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed.

In some embodiments, the polypeptide can have a fusion tag (e.g., SEQ ID NO: 7, 8, 9, or 10). These fusion tags can be used to purify polypeptides.

In some embodiments, the polypeptide can have an epitope (e.g., 6×His) that can be specifically recognized by an antibody (e.g., anti-6×His antibody). A label (e.g., fluorophore) can be conjugated to the antibody, thereby associating with the polypeptide.

In some embodiments, the polypeptide is a fusion polypeptide and can comprise a luciferase (e.g., SEQ ID NO: 11). The luciferase can be located at the N-terminus or the C-terminus of the polypeptide.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the nucleic acid sequence is at least 60%, 65%, 70%, 75%, 80%, 85%, 90%, 91%, 92%, 93%, 94%, 95%, 96%, 97%, 98%, 99% identical to any nucleotide sequence as described herein. In some embodiments, the amino acid sequence is at least 60%, 65%, 70%, 75%, 80%, 85%, 90%, 91%, 92%, 93%, 94%, 95%, 96%, 97%, 98%, 99% identical to any amino acid sequence as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, 600, 700, 800, 900, or 1000 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, 200, 400, 500, 600, 700, 800, 900, or 1000 amino acid residues.

PARP Probes

The present disclosure provides high affinity active site probes that bind in the $NAD^+$ pocket of PARPs (e.g., monoPARPs) which can be used to develop high-throughput biophysical assays. These probes are based on the structure-activity relationship (SAR) and binding mode of inhibitors that bind to the $NAD^+$ pocket of monoPARP enzymes. Thus, as used herein, the term "PARP probe" refers to an agent (e.g., a small molecule) that can bind to the active site of a PARP.

Many enzyme inhibitors inhibit the functions of enzymes by preventing a substrate from entering the enzyme's active site. Thus, if a test compound can prevent an active site probe from binding to the enzyme's active site, the test compound can also prevent a substrate from entering the enzyme's active site, thus working as an inhibitor. Therefore, in some embodiments, these PARP inhibitors can compete with PARP probes, bind to or occupy enzyme's active site, and/or displace the PARP probes.

In some embodiments, the PARP probe has a structure according to Formula (I):

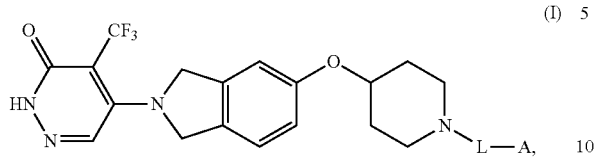

or a salt thereof,
wherein:

L is a linking group having 10-30 spacer atoms selected from C, N, O, and S connecting the N atom of the piperidinyl group of Formula (I) with group A; and A is a fluorophore or an affinity tag.

In some embodiments,
L is:

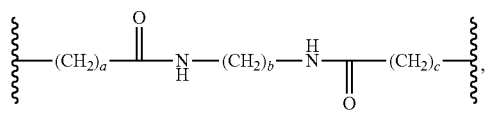

wherein:
a is 0, 1, or 2;
b is 1-26; and
c is 0, 1, or 2;
wherein the sum of a+b+c is 1 to 26, or L is a chain of 5-30 atoms in length comprising $-(CH_2CH_2O)_d-$ wherein d is 2-10.

In some embodiments, A is an organic dye.

In some embodiments, A is biotin.

In some embodiments, A is:

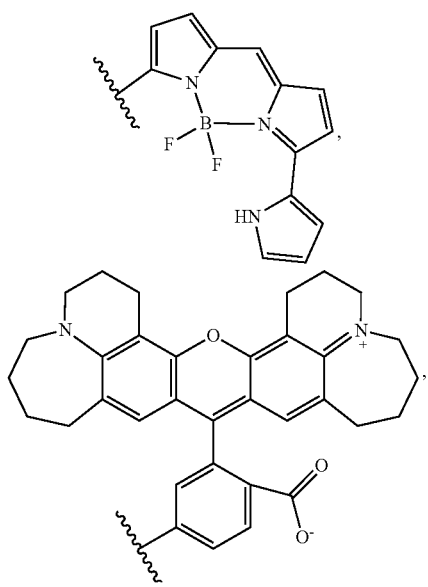

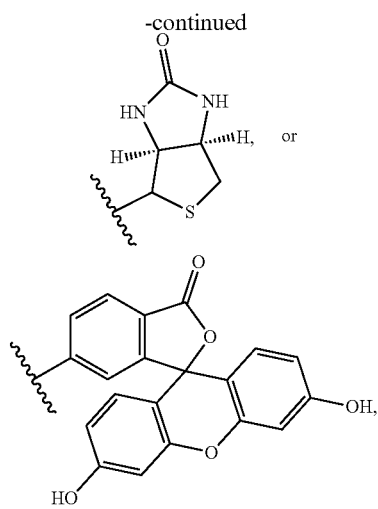

or a salt thereof.

As used herein, the term "fluorophore" refers to a chemical compound that can re-emit light upon light excitation. The donor is the fluorophore that emits light of shorter wavelength which is used to excite the acceptor, causing it to emit light of longer wavelength. Fluorophores can be organic molecules like fluorescein and similar organic dye moieties. Fluorophores can also include inorganic components like transition metals.

An affinity tag is a chemical or polypeptide group that can bind to other chemical or polypeptide molecules covalently or non-covalently (e.g., preferably with high affinity). Examples of non-covalent affinity tags are biotin which binds to streptavidin and antibodies, hexahistidine which binds to nickel-nitrilotriacetic acid and antibodies, glutathione which binds to glutathione S-transferase and antibodies, etc. Examples of covalent affinity tags are primary amines such as lysine which react with N-hydroxysuccinamide, as well as free thiols such as cysteine which react with other free thiols to form disulfide bonds. In some embodiments, the affinity tag is biotin.

Where a PARP probe "is labeled" with a fluorophore, the PARP probe can contain an affinity tag that covalently or non-covalently binds with a molecule (e.g., streptavidin or an antibody) having a fluorophore. Where a PARP probe comprises a fluorophore or an affinity tag, the fluorophore or affinity tag is generally understood to be part of the probe molecule.

The PARP probes of the invention, including salts thereof, can be prepared using known organic synthesis techniques and can be synthesized according to any of numerous possible synthetic routes.

The reactions for preparing compounds as described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds as described herein can involve the protection and deprotection of various chemical groups.

The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

Time-Resolved Fluorescence Resonance Energy Transfer (TR-FRET) Probe Displacement Assay The PARP probes can be used in time-resolved fluorescence resonance energy transfer (TR-FRET) probe displacement assays. TR-FRET is the combination of time-resolved fluorometry (TRF) with Förster resonance energy transfer (FRET). It can offer a powerful tool for studying the interactions between biomolecules.

FRET occurs when a donor fluorophore in its excited state transfers energy by a non-radiative dipole-dipole coupling mechanism to an acceptor fluorophore in close proximity (e.g., <10 nm). As a result, the acceptor emission is predominantly observed because of the intermolecular FRET from the donor to the acceptor. FRET can be quantified in cuvette-based experiments or in microscopy images on a pixel-by-pixel basis. This quantification can be based directly on detecting two emission channels under two different excitation conditions (primarily donor and primarily acceptor). However, for robustness reasons, FRET quantification is most often based on measuring changes in fluorescence intensity.

The biological fluids or serum commonly used in these research applications contain many compounds and proteins which are naturally fluorescent. Therefore, the use of conventional, steady-state fluorescence measurement presents serious limitations in assay sensitivity.

To reduce assay interference and increase data quality, a time-resolved FRET (TR-FRET) assay can be used to identify PARP inhibitors. TR-FRET generally employs a long-lifetime donor fluorophore (e.g., terbium chelate, samarium, europium, terbium, and dysprosium) and a suitable acceptor fluorophore (fluorescein or allophycocyanin).

As shown in FIG. 1, TR-FRET can be used to identify an agent that can inhibit the binding between the PARP probe and the PARP polypeptide. The methods involve providing a polypeptide comprising a PARP catalytic domain. The polypeptide is labeled with a donor fluorophore. In the meantime, the PARP probe is labeled with an acceptor fluorophore. When the donor fluorophore is exposed to excitation light, the energy is transferred from the donor fluorophore to the acceptor fluorophore. The signal produced by the acceptor fluorophore is measured. In the presence of an agent (e.g., a PARP inhibitor) that can inhibit the binding between the PARP probe and the PARP polypeptide, the PARP probe is not in close proximity with the PARP polypeptide, thus the energy cannot be effectively transferred from the donor fluorophore to the acceptor fluorophore. Therefore, the signal produced by the acceptor fluorophore will decrease.

In certain embodiments, an agent (e.g., a test compound) is identified as a PARP inhibitor if it results in a decrease in the signal produced by the acceptor fluorophore by at least 10%, at least 15%, at least 20%, at least 25%, at least 30%, at least 40%, at least 50%, at least 60%, at least 70%, at least 80%, at least 90%, or at least 95% as compared to the signal of the acceptor fluorophore in the absence of the agent or any agent that can inhibit or interfere with the binding between the PARP probe and the PARP polypeptide.

In some embodiments, the signal produced by the acceptor fluorophore can be compared to a reference level. The reference level can be the signal produced by the acceptor fluorophore in the absence of any agent that can inhibit or interfere with the binding between the PARP probe and the polypeptide.

In certain embodiments, an agent (e.g., a test compound) is identified as a PARP inhibitor if it results in a decrease in the ratio of the signal produced by the acceptor to the signal produced by the donor by at least 10%, at least 15%, at least 20%, at least 25%, at least 30%, at least 40%, at least 50%, at least 60%, at least 70%, at least 80%, at least 90%, or at least 95% as compared to the ratio in the absence of the agent or any agent that can inhibit or interfere with the binding between the PARP probe and the PARP polypeptide.

In some embodiments, the ratio of the signal produced by the acceptor to the signal produced by the donor can be compared to a reference level. The reference level can be the ratio of the acceptor signal to the donor signal in the absence of any agent that can inhibit or interfere with the binding between the PARP probe and the polypeptide.

In some embodiments, the polypeptide can be labeled with a donor fluorophore, and the PARP probe can be labeled with an acceptor fluorophore.

A variety of fluorophore combinations can be used in TR-FRET. In some embodiments, lanthanide ion complexes (Ln(III) chelates or cryptates) are used. In some embodiments, the donor fluorophore is Europium$^{3+}$, and the acceptor fluorophore is allophycocyanin. In some embodiments, the donor fluorophore is Terbium3+, and the acceptor fluorophore is phycoerythrin.

TR-FRET measurements can be also carried out using any suitable technique. For example, a microscope image of donor emission can be taken with the acceptor being present. The acceptor is then bleached, such that it is incapable of accepting energy transfer and another donor emission image is acquired. A pixel based quantification using the second equation in the theory section above is then possible. An alternative way of temporarily deactivating the acceptor is based on its fluorescence saturation.

In some embodiments, the ratio between the signal produced by the acceptor and the signal produced by the donor is calculated. The % inhibition can be calculated as described below:

$$\% \text{ inhibition} = 100 \times \frac{TRF_{cmpd} - TRF_{min}}{TRF_{max} - TRF_{min}}$$

wherein $TRF_{cmpd}$ is the TR-FRET ratio from the compound treated solution, $TRF_{min}$ is the TR-FRET ratio from a positive control and $TRF_{max}$ is the TR-FRET ratio from the negative control (e.g., DMSO-treated).

The % inhibition values can be plotted as a function of compound concentration and the following 4-parameter fit can be applied to derive the $IC_{50}$ values:

$$Y = \text{Bottom} + \frac{(\text{Top} - \text{Bottom})}{\left(1 + \left(\frac{X}{IC_{50}}\right)^{\text{Hill Coefficient}}\right)}$$

wherein top and bottom can be normally allowed to float, but may be fixed at 100 or 0 respectively in a 3-parameter fit. The Hill Coefficient can be normally allowed to float but may also be fixed at 1 in a 3-parameter fit. Y is the % inhibition and X is the compound concentration. $IC_{50}$ is the concentration of an inhibitor where the response (or binding) is reduced by half. It is a measure of the potency of a substance in inhibiting a specific biological or biochemical function. Based on the modeling, $IC_{50}$ can be estimated.

FRET and TR-FRET methods, protocols, techniques, and assays are described generally and specifically in a number of patents and patent applications, including, e.g., U.S. Pat. Nos. 6,908,769; 6,824,990; 6,762,280; 6,689,574; 6,661,909; 6,642,001; 6,639,078; 6,472,156; 6,456,734; 6,376,257; 6,348,322; 6,323,039; 6,291,201; 6,280,981; 5,914,245; 5,661,035; and US 20080113444; US 2009021510; Du et al. "A time-resolved fluorescence resonance energy transfer assay for high-throughput screening of 14-3-3 protein-protein interaction inhibitors." Assay and drug development technologies 11.6 (2013): 367-381; each of which is incorporated herein by reference in its entirety.

Fluorescence Polarization Probe Displacement Assay

The PARP probes can also be used in a fluorescence polarization probe displacement assay. Fluorescence polarization (FP) is a homogeneous method that allows rapid and quantitative analysis of diverse molecular interactions and enzyme activities. This technique has been widely used in clinical and biomedical settings, and high-throughput screening (HTS).

In fluorescence polarization assays, a fluorophore is excited with polarized excitation light; the polarized fluorescence is then measured through an emission polarizer either parallel or perpendicular to the exciting light's plane of polarization. If a fluorescent molecule is stationary and exposed to plane-polarized light, it will become excited and consequently emit radiation back to the polarized-plane. However, if the excited fluorescent molecule is in motion (rotational or translational) during the fluorescent lifetime, it will emit light in a different direction than the excitation plane. The rate at which a molecule rotates is indicative of its size. When a fluorescent-labelled molecule binds to another molecule, the rotational motion will change, resulting in an altered intensity of plane-polarized light, which results in altered fluorescence polarization.

Figure 2:
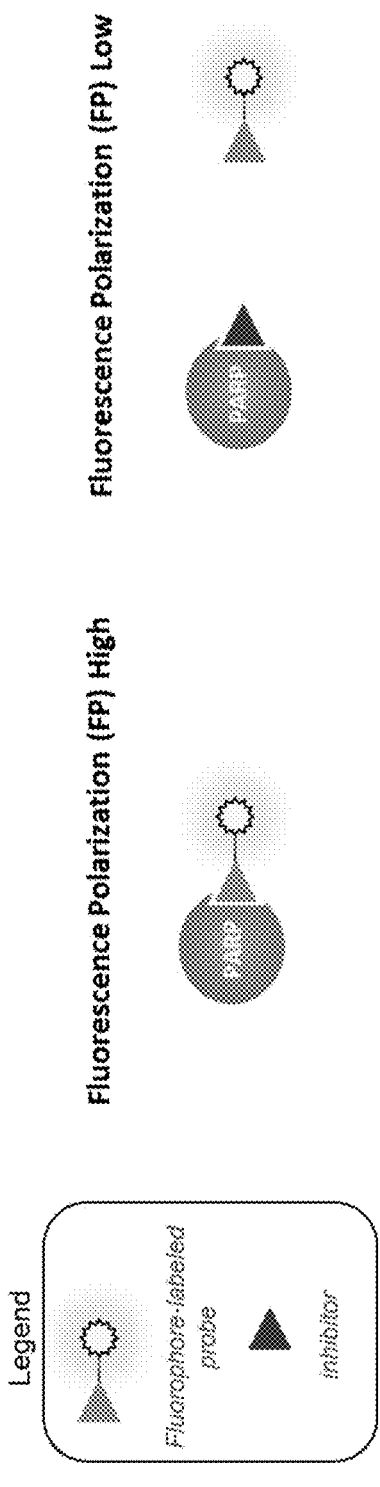
FIG. 2 is a schematic diagram illustrating an example of in vitro fluorescence polarization probe displacement assay. An inhibitor will outcompete the fluorophore-labeled probe and decrease fluorescence polarization signal.

As shown in FIG. 2, when the PARP probe binds to the PARP polypeptide, the complex has a relatively larger molecular size. When an agent (e.g., PARP inhibitor) inhibits the binding between the PARP probe and the PARP polypeptide, the PARP probe with the fluorophore will not bind to the PARP polypeptide, thus the probe can rotate more quickly, resulting in a decrease of fluorescence polarization. This change can be detected, thereby determining whether an agent is a PARP inhibitor. In certain embodiments, an agent (e.g., a test compound) is identified as a PARP inhibitor if the fluorescence polarization decreases by at least 10%, at least 15%, at least 20%, at least 25%, at least 30%, at least 40%, at least 50%, at least 60%, at least 70%, at least 80%, at least 90%, or at least 95% as compared to the fluorescence polarization in the absence of the agent or any agent that can inhibit or interfere with the binding between the PARP probe and the PARP polypeptide.

A detailed description of fluorescence polarization and the method of implementing it is described, e.g., in Lea, Wendy A., and Anton Simeonov. "Fluorescence polarization assays in small molecule screening." Expert opinion on drug discovery 6.1 (2011): 17-32; U.S. Pat. No. 6,432,632; US20030082665; each of which is incorporated herein by reference in its entirety.

Bioluminescence Resonance Energy Transfer (BRET) Probe Displacement Assay

The PARP probes can also be used in bioluminescence resonance energy transfer (BRET) probe displacement assays. A limitation of FRET is the requirement for external illumination to initiate the fluorescence transfer, which can lead to background noise. Bioluminescence resonance energy transfer involves a bioluminescent luciferase (e.g., the luciferase from *Renilla reniformis*, or *Oplophorus gracilirostris*) to produce an initial photon emission.

Figure 3:
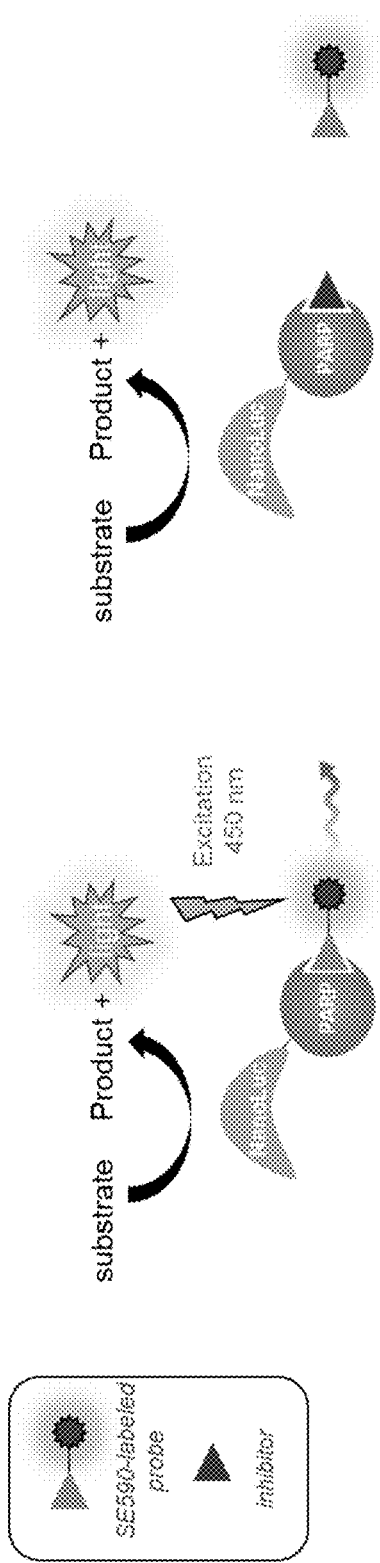
FIG. 3 is a schematic diagram illustrating an example of bioluminescence resonance energy transfer probe displacement assay. An inhibitor will outcompete the fluorophore-labeled probe and decrease NanoBRET signal.
Figure 5B:
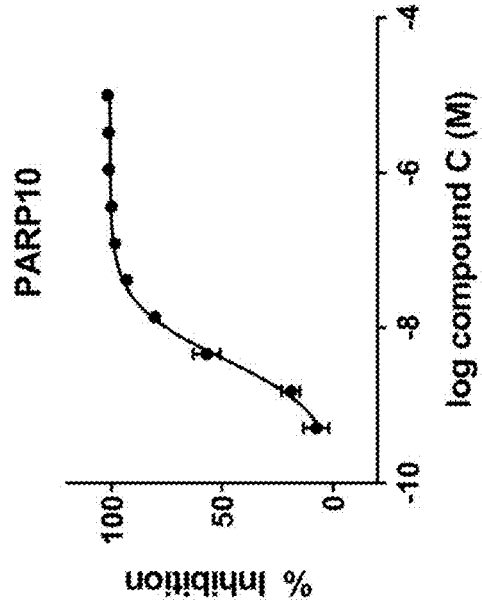
FIGS. 5A-5D. Validation results of the bioluminescence resonance energy transfer probe displacement binding assays. Dose response curves for control compounds were generated using each assay to confirm that Probe A was outcompeted from the monoPARP enzyme. $IC_{50}$ values for catalytic TIPARP Compound B=7 nM, full-length TIPARP Compound B=4 nM, PARP10 Compound C=4 nM, PARP12 Compound B=170 nM, PARP14 Compound A=30 nM.
Figure 5D:
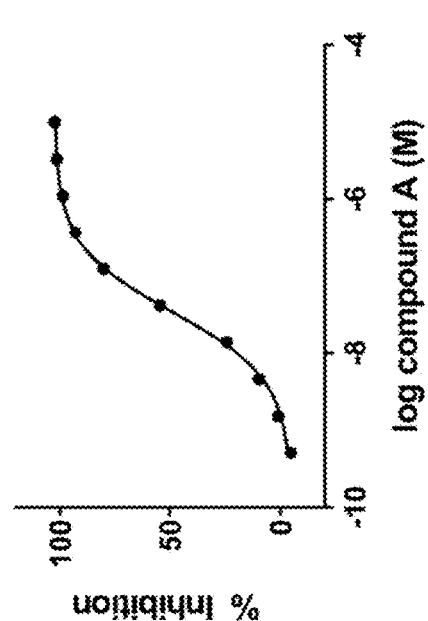
Figure 5A:
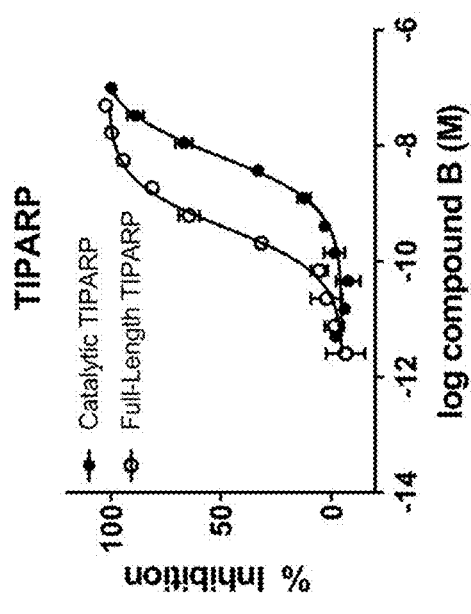
Figure 5C:
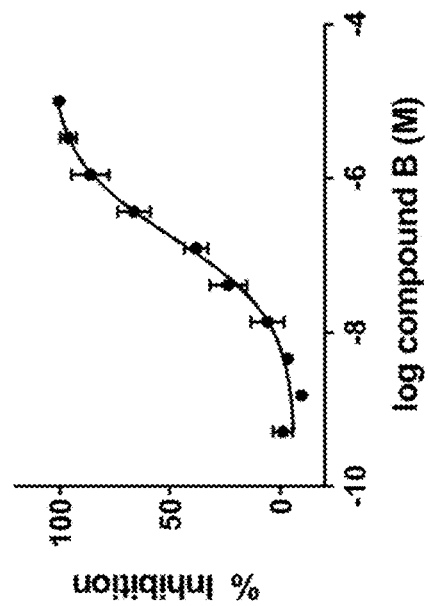

As compared to FRET, in BRET, the donor fluorophore is replaced by a luciferase. As shown in FIG. 3, in the presence of a substrate, bioluminescence from the luciferase excites the acceptor fluorophore through Förster resonance energy transfer mechanisms. Thus, if the acceptor fluorophore is in close proximity with the luciferase, the acceptor fluorophore accepts the energy from the luciferase and emits a light with different length.

When an agent (e.g., PARP inhibitor) inhibits the binding between PARP probe and the PARP polypeptide, the PARP probe with the acceptor fluorophore will not be in close proximity with the PARP polypeptide, thus the light from the luciferase enzyme reaction cannot be transferred to the acceptor fluorophore, resulting a decrease of fluorescence emitted from the acceptor fluorophore. This change can be detected, thereby determining whether an agent is a PARP inhibitor. In certain embodiments, an agent (e.g., a test compound) is identified as a PARP inhibitor if it results in a decrease in the fluorescence emitted from the acceptor fluorophore by at least 10%, at least 15%, at least 20%, at least 25%, at least 30%, at least 40%, at least 50%, at least 60%, at least 70%, at least 80%, at least 90%, or at least 95% as compared to the fluorescence emitted from the acceptor fluorophore in the absence of the agent or any agent that can inhibit or interfere with the binding between the PARP probe and the PARP polypeptide.

In some embodiments, the luciferase is NanoLuc, and the acceptor fluorophore is NanoBRET® 590SE.

BRET ratio can be measured by the formula as shown below:

$$\text{BRET ratio} = \frac{\text{Emission of the acceptor fluorophore}}{\text{Luminescence}}$$

Control wells containing a negative control or a positive control are used to calculate the % inhibition as described below:

$$\% \text{ inhibition} = 100 \times \frac{\text{BRET ratio}_{cmpd} - \text{BRET ratio}_{min}}{\text{BRET ratio}_{max} - \text{BRET ratio}_{min}}$$

wherein BRET ratio$_{cmpd}$ is the BRET ratio from the compound treated solution, BRET ratio$_{min}$ is the BRET ratio from the positive control and BRET ratio$_{max}$ is the BRET ratio from the negative control.

The % inhibition values are plotted as a function of compound concentration and the following 4-parameter fit is applied to derive the IC$_{50}$ values:

$$Y = \text{Bottom} + \frac{(\text{Top} - \text{Bottom})}{(1 + \left(\frac{X}{IC_{50}}\right)^{\text{Hill Coefficient}})}$$

wherein top and bottom can be normally allowed to float, but may be fixed at 100 or 0 respectively in a 3-parameter fit. The Hill Coefficient can be normally allowed to float but may also be fixed at 1 in a 3-parameter fit. Y is the % inhibition and X is the compound concentration. The IC$_{50}$ value can be derived from the modeling.

High Throughput Screening and Compound Library

The assays as described herein can be used in high throughput screening for PARP modulators (e.g., monoPARP inhibitors). Such assays can be used to screen small molecule libraries available from various commercial sources. Screening of such libraries, including combinatorially generated libraries (e.g., peptide libraries), is a rapid and efficient way to screen a large number of related (and unrelated) compounds for activity.

This disclosure provides methods for screening test compounds, e.g., polypeptides (including, e.g., antibodies and antigen-binding fragments thereof), polynucleotides, inorganic or organic large or small molecule test compounds, to identify agents useful for modulating PARP enzymatic activity, and for the treatment of disorders associated with PARP overexpression or overactivity (e.g., cancer or inflammation).

As used herein, "small molecules" refers to small organic or inorganic molecules of molecular weight below about 3,000 Daltons. In general, small molecules useful for the methods as described herein can have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available.

Libraries screened using the methods as described herein can comprise a variety of types of test compounds. A given library can comprise a set of structurally related or unrelated test compounds. In some embodiments, the test compounds are peptide or peptidomimetic molecules. In some embodiments, the test compounds are nucleic acids. In some embodiments, the test compounds are antibodies or antigen-binding fragments thereof.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue, e.g., tumor tissue, and one or more effects of the test compound is evaluated. For example, the ability of the test compound to inhibit cell growth or tumor growth is evaluated.

In some embodiments, the test sample is, or is derived from (e.g., a sample taken from) an in vivo model. For example, an animal model, e.g., a rodent such as a rat, can be used.

Thus, test compounds identified as "hits" (e.g., test compounds that can inhibit PARP) in a first screen can be selected and systematically altered, e.g., using rational design, to optimize binding affinity, avidity, specificity, or other parameter. Such optimization can also be screened for using the methods described herein. Thus, in one embodiment, the disclosure includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with PARP overexpression or overactivity (e.g., cancer). A variety of techniques useful for determining the structures of "hits" can be used in the methods described herein, e.g., NMR, mass spectrometry, gas chromatography equipped with electron capture detectors, fluorescence and absorption spectroscopy. Thus, the disclosure also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a disorder associated with PARP overexpression or overactivity (e.g., cancer). The animal can be monitored for a change in the disorder, e.g., for an improvement in a parameter of the disorder, e.g., a parameter related to clinical outcome. In some embodiments, the parameter is tumor growth, and an improvement would inhibit tumor growth.

In some embodiments, the PARP modulators obtained from the screening are inhibitors of PARP1, PARP2, PARP3, PARP4, PARP5a, PARP5b, PARP6, TIPARP, PARP8, PARP9, PARP10, PARP11, PARP12, PARP13, PARP14, PARP15, or PARP16. In some embodiments, the inhibitors have an $IC_{50}$ for a PARP (e.g., PARP1, PARP2, PARP3, PARP4, PARP5a, PARP5b, PARP6, TIPARP, PARP8, PARP9, PARP10, PARP11, PARP12, PARP13, PARP14, PARP15, or PARP16) of less than 1, 2, 3, 4, 5, 6, 7, 8, 9, 10, 20, 30, 40, 50, 60, 70, 80, 90, 100, 110, 120, 130, 140, 150, 160, 170, 180, 190, or 200 nM.

In some embodiments, the binding affinity of the PARP inhibitors ($K_d$) (between the compound and PARP) is less than $1\times10^{-6}$ M, less than $1\times10^{-7}$ M, less than $1\times10^{-8}$ M, less than $1\times10^{-9}$ M, or less than $1\times10^{-10}$ M. In some embodiments, the $K_d$ is less than 50 nM, 30 nM, 20 nM, 15 nM, 10 nM, 9 nM, 8 nM, 7 nM, 6 nM, 5 nM, 4 nM, 3 nM, 2 nM, or 1 nM. In some embodiments, $K_d$ is greater than $1\times10^{-7}$ M, greater than $1\times10^{-8}$ M, greater than $1\times10^{-9}$ M, greater than $1\times10^{-10}$ M, greater than $1\times10^{-11}$ M, or greater than $1\times10^{-12}$ M.

Methods of Treatment

The methods described herein include methods for the treatment of diseases or disorders associated with PARP overexpression or overactivity comprising administering to a patient in need thereof a therapeutically effective amount of a compound identified according to one or more of the assays described herein. In some embodiments, the disease or disorder is cancer. Generally, the methods include administering a therapeutically effective amount of PARP modulators (e.g., inhibitors) identified by the methods as described herein, to a subject who is in need of, or who has been determined to be in need of, such treatment. As used in this context, to "treat" means to ameliorate at least one symptom of the disorder associated with PARP overexpression or overactivity. Often, the treatment results in a decreased activity of PARP.

In some embodiments, the disease or disorder is cancer. In some embodiments, administration of a therapeutically effective amount of a compound described herein can result in a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells.

As used herein, the terms "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

Kits and Compositions

The present disclosure also provides kits for PARP inhibitor screening. The kit can include a PARP probe comprising a fluorophore or an affinity tag. The kit can also include a polypeptide comprising a PARP catalytic domain and optionally a fusion/affinity tag (e.g., hexahistidine). In some embodiments, the polypeptide is labeled with a fluorophore.

The present disclosure also provides compositions for the PARP inhibitors. In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

EXAMPLES

The invention is further described in the following examples, which do not limit the scope of the invention described in the claims.

Materials and Methods

The following equipment and methods were used in the following examples.

$^1$H NMR Spectra were recorded at 300 or 400 MHz using a Bruker AVANCE 400 MHz spectrometer. NMR interpretation was performed using MestReC or MestReNova software to assign chemical shift and multiplicity. In cases where two adjacent peaks of equal or unequal height were observed, these two peaks may be labeled as either a multiplet or as a doublet. In the case of a doublet, a coupling constant using this software may be assigned. In any given example, one or more protons may not be observed due to obscurity by water and/or solvent peaks.

Liquid chromatography-mass spectrometry (LCMS) equipment and conditions were as follows:

1. Liquid chromatography (LC): Agilent Technologies 1290 series, Binary Pump, Diode Array Detector. Agilent Poroshell 120 EC-C18, 2.7 μm, 4.6×50 mm column. Mobile phase: A: 0.05% Formic acid in water (v/v), B: 0.05% Formic acid in ACN (v/v). Flow Rate: 1 mL/min at 25° C. Detector: 214 nm, 254 nm. Gradient stop time, 10 min. Timetable is shown below:

TABLE 2

| T (min) | A(%) | B(%) |
|---|---|---|
| 0.0 | 90 | 10 |
| 0.5 | 90 | 10 |
| 8.0 | 10 | 90 |
| 10.0 | 0 | 100 |

2. Mass spectrometry (MS): G6120A, Quadrupole LC/MS, Ion Source: ES-API, TIC: 70~1000 m/z, Fragmentor: 60, Drying gas flow: 10 L/min, Nebulizer pressure: 35 psi, Drying gas temperature: 350° C., Vcap: 3000V.
3. Sample preparation: samples were dissolved in ACN or methanol at 1~10 mg/mL, then filtered through a 0.22 μnm filter membrane. Injection volume: 1~10.

The following abbreviations are used in the disclosure: ACN (acetonitrile); Boc (tert-butoxycarbonyl); Boc2O (di-tert-butyl dicarbonate); CuI (copper iodide); CDCl₃ (deuterated chloroform); CD₃OD (deuterated methanol); DCM (dichloromethane); DIPEA (N,N-diisopropylethylamine); DMF (N,N-dimethylformamide); DMSO (dimethylsulfoxide); DMSO-d₆ (deuterated dimethylsulfoxide); eq (equivalent); EtOAc (ethyl acetate); g (gram); h (hour); HATU (1-[bis(dimethylamino)methylene]-1H-1,2,3-triazolo[4,5-b]pyridinium 3-oxide hexafluorophosphate); ¹H NMR (proton nuclear magnetic resonance); HCl (hydrochloric acid); Hz (hertz); L (litre); LiCl (lithium chloride); LCMS (liquid chromatography-mass spectrometry); M (molar); MeOH (methanol); mg (milligrams); MHz (megahertz); min (minutes); mL (millilitres), mmol (millimoles); NMP (N-methyl-2-pyrrolidone); prep-HPLC (preparative high-performance liquid chromatography); Pd(OAc)2 (palladium (II) acetate); ppm (parts per million); Pd(allyl)Cl₂ (Bis(η3-allyl)di(μ-chloro)dipalladium(II)); Rockphos (2-Di(tert-butyl)phosphino-2,4,6-triisopropyl-3-methoxy-6-methylbiphenyl); RT (room temperature); SEM (2-(trimethylsilyl)ethoxymethyl); SEMCl (2-(trimethylsilyl)ethoxymethyl chloride); TEA (triethyl amine); tBuBrettphos (2-(Di-tert-butylphosphino)-2,4,6-triisopropyl-3,6-dimethoxy-1,1-biphenyl); THF (tetrahydrofuran); TLC (thin layer chromatography); v/v (volume/volume).

Example 1: Synthesis of Intermediates

Int-A1: 5-Chloro-4-(trifluoromethyl)-2-[[2-(trimethylsilyl)ethoxy]methyl]-2,3-dihydropyridazin-3-one

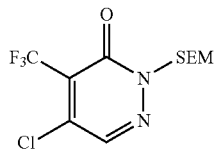 [SMILES: C[Si](C)(C)CCOCn1ncc(Cl)c(C(F)(F)F)c1=O]

Step 1: 4,5-Dibromo-2-[[2-(trimethylsilyl)ethoxy]methyl]-2,3-dihydropyridazin-3-one To a solution of 4,5-dibromo-2,3-dihydropyridazin-3-one (3500 g, 13.78 mol, 1.00 equiv) in DMF (30 L) was added sodium hydride (400 g, 16.56 mol, 1.20 equiv) in batches at 0° C. under nitrogen. The resulting solution was stirred for 1 hour at room temperature, then [2-(chloromethoxy)ethyl]trimethylsilane (2500 g, 15.2 mol, 1.10 equiv) was added dropwise at 0° C. and stirred for 2 hours at room temperature. The reaction was then quenched by the addition of 30 L of water. The resulting solution was extracted with 3×50 L of ethyl acetate and the organic layers combined. The organic layers were washed with 3×30 L of brine, dried over anhydrous sodium sulfate and concentrated under reduced pressure to afford 4.2 kg of title compound. LCMS: [M+H]⁺ 384.70.

Step 2: 4-Bromo-5-chloro-2-[[2-(trimethylsilyl)ethoxy]methyl]-2,3-dihydropyridazin-3-one To a solution of 4,5-dibromo-2-[[2-(trimethylsilyl)ethoxy]methyl]-2,3-dihydropyridazin-3-one (2200 g, 5.73 mol, 1.00 equiv) in NMP (6 L) was added chlorolithium (231 g, 5.73 mol, 1.00 equiv) and stirred for 4 hours at 95° C. The reaction was then diluted by the addition of 10 L of water, extracted with 3×20 L of ethyl acetate and the organic layers combined. The organic layers were washed with 3×20 L of brine, dried over anhydrous sodium sulfate and concentrated under reduced pressure. The residue was purified by column chromatography (EtOAc:petroleum ether, 1:50, v/v) to afford 4.2 kg of 4,5-dibromo-2-[[2-(trimethylsilyl)ethoxy]methyl]-2,3-dihydropyridazin-3-one. This was repeated 2 times resulting in 2.2 kg of 4-bromo-5-chloro-2-[[2-(trimethylsilyl)ethoxy]methyl]-2,3-dihydropyridazin-3-one. LCMS: [M+H]⁺ 340.90.

Step 3: 5-Chloro-4-(trifluoromethyl)-2-[[2-(trimethylsilyl)ethoxy]methyl]-2,3-dihydropyridazin-3-one To a solution of 4-bromo-5-chloro-2-[[2-(trimethylsilyl)ethoxy]methyl]-2,3-dihydropyridazin-3-one (1100 g, 3.23 mol, 1.00 equiv) in NMP (6 L) at room temperature was added CuI (56 g, 0.64 mol, 0.20 equiv) followed by dropwise addition of methyl 2,2-difluoro-2-(fluorosulfonyl)acetate (1865 g, 9.7 mol, 3.00 equiv). The resulting solution was stirred for 2 hours at 80° C. The reaction was then quenched by the addition of 10 L of water and extracted with 3×10 L of ethyl acetate. The organic layers were combined and washed with 3×10 L of brine, dried over anhydrous sodium sulfate, and concentrated under reduced pressure. The residue was purified by column chromatography (ethyl acetate/petroleum ether, 1/100, v/v) to afford 1030 g (76%) of the title compound. LCMS: [M+H]⁺ 329.00.
¹H NMR (300 MHz, CDCl₃) δ 7.82 (s, 1H), 5.50 (d, J=27.3 Hz, 2H), 3.74 (dt, J=12.9, 8.2 Hz, 2H), 0.97 (td, J=8.3, 5.0 Hz, 2H), 0.01 (d, J=2.1 Hz, 9H).

Int-A2: 2-[4-([2-[6-Oxo-5-(trifluoromethyl)-1,6-dihydropyridazin-4-yl]-2,3-dihydro-1H-isoindol-5-yl]oxy)piperidin-1-yl]acetic Acid

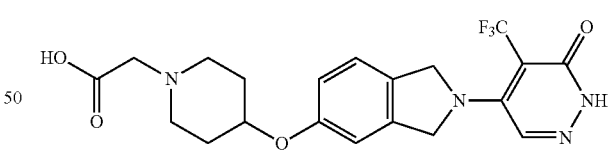

Step 1: 5-(5-Hydroxy-2,3-dihydro-1H-isoindol-2-yl)-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (2.8 g, 8.52 mmol, 1.00 equiv), 2,3-dihydro-1H-isoindol-5-ol hydrobromide (4.27 g, 19.76 mmol, 1.00 equiv), and TEA (10 mL) in ethanol (40 mL) was stirred for 1 h at 60° C. The resulting solution was extracted with 2×100 mL of ethyl acetate and the organic layers combined and concentrated under reduced pressure to afford 4.5 g of the title compound as a yellow oil. LCMS: [M+H]⁺ 428.23.

Step 2: tert-Butyl 4-([2-[6-oxo-5-(trifluoromethyl)-1-[[2-(trimethylsilyl)ethoxy]methyl]-1,6-dihydro-pyridazin-4-yl]-2,3-dihydro-1H-isoindol-5-yl]oxy)piperidine-1-carboxylate A solution of 5-(5-hydroxy-2,3-dihydro-1H-isoindol-2-yl)-4-(trifluoromethyl)-2-[[2-(trimethylsilyl)ethoxy]methyl]-2,3-dihydropyridazin-3-one (4.5 g, 10.53 mmol, 1.00 equiv), tert-butyl 4-iodopiperidine-1-carboxylate (20 g, 64.28 mmol, 8.00 equiv), potassium carbonate (15 g, 108.53 mmol, 10.00 equiv), and DMF (50 mL) was stirred for 2 days at 80° C. The resulting solution was extracted with 2×200 mL of ethyl acetate and the organic layers combined and concentrated under reduced pressure. The residue was applied onto a silica gel column eluting with ethyl acetate/petroleum ether to afford the title compound (2 g, 31%) as a yellow oil. LCMS: [M+H]$^+$ 611.15.

Step 3: 5-[5-(Piperidin-4-yloxy)-2,3-dihydro-1H-isoindol-2-yl]-4-(trifluoromethyl)-2-[[2-(trimethylsilyl)ethoxy]methyl]-2,3-dihydropyridazin-3-one A solution of tert-butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate (2 g, 3.27 mmol, 1.00 equiv), dioxane/HCl (5 mL), and dioxane (45 mL) was stirred for 6 h at 25° C. The resulting mixture was concentrated under reduced pressure. The residue was applied onto a silica gel column and eluted with ethyl acetate/petroleum ether to afford 1 g of title compound as a yellow oil. LCMS: [M+H]$^+$ 511.28.

Step 4: tert-Butyl 2-[4-([2-[6-oxo-5-(trifluoromethyl)-[[2-(trimethylsilyl)ethoxy]methyl]-1,6-dihydropyridazin-4-yl]-2,3-dihydro-1H-isoindol-5-yl]oxy)piperidin-1-yl]acetate A solution of 5-[5-(piperidin-4-yloxy)-2,3-dihydro-1H-isoindol-2-yl]-4-(trifluoromethyl)-2-[[2-(trimethylsilyl)ethoxy]methyl]-2,3-dihydropyridazin-3-one ((1 g, 1.96 mmol, 1.00 equiv), tert-butyl 2-chloroacetate (450 mg, 2.99 mmol, 3.00 equiv), DIPEA (5 mL), and dichloromethane (10 mL) was stirred overnight at 25° C. The residue was purified by C18 reverse phase chromatography eluting with H$_2$O/CH$_3$CN to afford the title compound (540 mg, 44%) as a yellow oil. LCMS: [M+H]$^+$ 625.20.

Step 5: 2-[4-([2-[6-Oxo-5-(trifluoromethyl)-1,6-dihydropyridazin-4-yl]-2,3-dihydro-1H-isoindol-5-yl]oxy)piperidin-1-yl]acetic Acid A solution of tert-butyl 2-[4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidin-1-yl]acetate (540 mg, 0.86 mmol, 1.00 equiv) and dioxane/HCl (8 mL) was stirred overnight at 25° C. The resulting mixture was concentrated under reduced pressure. The residue was purified by C18 reverse phase chromatography eluting with H$_2$O/CH$_3$CN to afford 200 mg (53%) of title compound as a white solid. LCMS: [M+H]$^+$ 439.31.

Example 2: Synthesis of Probe A

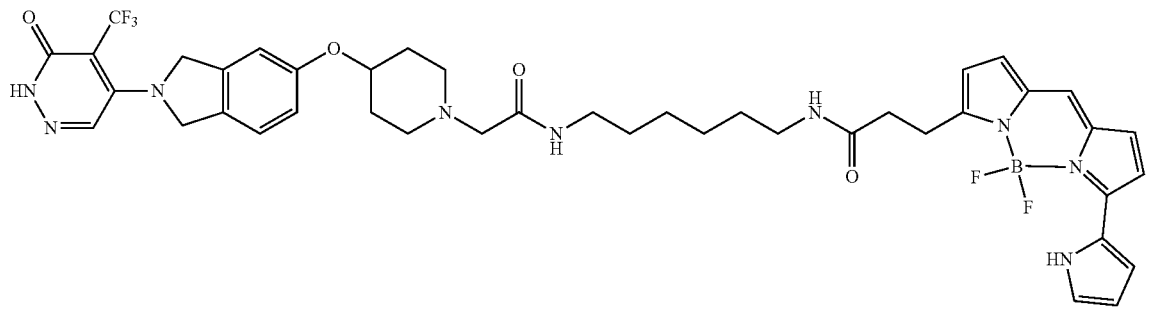

Step 1: tert-Butyl N-(6-[2-[4-([2-[6-oxo-5-(trifluoromethyl)-, 6-dihydropyridazin-4-yl]-2,3-dihydro-1H-isoindol-5-yl]oxy)piperidin-1-yl]acetamido]hexyl)carbamate A solution of 2-[4-([2-[6-oxo-5-(trifluoromethyl)-1,6-dihydropyridazin-4-yl]-2,3-dihydro-1H-isoindol-5-yl]oxy)piperidin-1-yl]acetic acid (Int-A2) (44 mg, 0.10 mmol, 1.00 equiv), DIPEA (52 mg, 0.40 mmol, 4.00 equiv), HATU (46 mg, 0.12 mmol, 1.20 equiv), and tert-butyl N-(6-aminohexyl)carbamate (24 mg, 0.11 mmol, 1.10 equiv) in DMF (1 mL) was stirred overnight at 25° C. The crude product was purified by C18 reverse phase chromatography eluting with H$_2$O/CH$_3$CN to afford 38 mg (59%) of title compound as an off-white solid. LCMS: [M+H]$^+$ 637.31.

Step 2: N-(6-Aminohexyl)-2-[4-([2-[6-oxo-5-(trifluoromethyl)-1,6-dihydropyridazin-4-yl]-2,3-dihydro-1H-isoindol-5-yl]oxy)piperidin-1-yl]acetamide Hydrochloride A solution of tert-butyl N-(6-[2-[4-([2-[6-oxo-5-(trifluoromethyl)-1,6-dihydropyridazin-4-yl]-2,3-dihydro-1H-isoindol-5-yl]oxy)piperidin-1-yl]acetamido]hexyl)carbamate (38 mg, 0.06 mmol, 1.00 equiv) in hydrogen chloride/dioxane (10 mL) was stirred for 3 hours at 25° C. The resulting mixture was concentrated under reduced pressure to afford the title compound as a gray solid (30 mg, 88%). LCMS: [M-Cl]$^+$: 537.27.

Step 3: 2,2-Difluoro-4-[2-[(6-[2-[4-([2-[6-oxo-5-(trifluoromethyl)-1,6-dihydropyridazin-4-yl]-2,3-dihydro-1H-isoindol-5-yl]oxy)piperidin-1-yl]acetamido]hexyl)carbamoyl]ethyl]-12-(1H-pyrrol-2-yl)-1^[5],3-diaza-2^[4]-boratricyclo[7.3.0.0^[3,7]]dodeca-1(12), 4,6,8,10-pentaen-1-yliumc A solution of NanoBRET® 590SE (N-(6-aminohexyl)-2-[4-([2-[6-oxo-5-(trifluoromethyl)-1,6-dihydropyridazin-4-yl]-2,3-dihydro-1H-isoindol-5-yl]oxy)piperidin-1-yl]acetamide hydrochloride (23 mg, 0.04 mmol, 2.00 equiv), DIPEA (52 mg, 0.40 mmol, 5.00 equiv), 4-3-[(2,5-dioxopyrrolidin-1-yl)oxy]-3-oxopropyl-2,2-difluoro-12-(1H-pyrrol-2-yl)-1^5,3-diaza-2^4-boratricyclo[7.3.0.0^3,7]dodeca-1 (12),4,6,8,10-pentaen-1-ylium) (10 mg, 0.02 mmol, 1.00 equiv) in dichloromethane (2 mL) and methanol (2 mL) was stirred for 2 h at 25° C. The resulting mixture was concentrated under reduced pressure and the crude product was purified by C18 reverse phase chromatography eluting with H₂O/CH₃CN to afford 6.9 mg of a purple solid (35%). LCMS: [M+H]⁺ 848.38.

¹H NMR (CD₃OD, 400 MHz) δ: 7.98 (s, 1H), 7.28-7.14 (m, 5H), 7.02-6.84 (m, 4H), 6.37-6.26 (m, 2H), 4.93 (d, J=12.0 Hz, 4H), 4.45-4.35 (m, 1H), 3.29-3.13 (m, 6H), 3.01 (s, 2H), 2.81-2.70 (m, 2H), 2.60 (t, J=7.7 Hz, 2H), 2.43 (td, J=8.7, 4.6 Hz, 2H), 2.01 (dd, J=11.8, 7.0 Hz, 2H), 1.81 (ddt, J=15.8, 11.5, 5.5 Hz, 2H), 1.51 (q, J=7.3, 6.8 Hz, 4H), 1.38-1.26 (m, 4H).

Example 3: Synthesis of Probe B isoindol-5-yl]oxy)piperidin-1-yl]acetamido]hexyl)carbamate (190 mg, 0.30 mmol, 1.00 equiv) and dioxane/HCl (6 mL) was stirred for 1 hour at 25° C. The resulting mixture was concentrated under reduced pressure. The residue was purified by C18 reverse phase chromatography eluting with H₂O/CH₃CN to afford 100 mg (58%) of title compound as a yellow oil. LCMS: [M+H]⁺ 537.27.

Step 3: 17-[2-Carboxylato-5-[(6-[2-[4-([2-[6-oxo-5-(trifluoromethyl)-1,6-dihydropyridazin-4-yl]-2,3-dihydro-1H-isoindol-5-yl]oxy)piperidin-1-yl]acetamido]hexyl)carbamoyl]phenyl]-3-oxa-9^[5], 25-diazaheptacyclo[18.8.1.1^[5, 9].0^[2,18].0^[4,16] .0^[25,29].0^[14,30]]triaconta-1(29), 2(18), 4, 9(30), 14,16,19-heptaen-9-ylium A solution of N-(6-aminohexyl)-2-[4-([2-[6-oxo-5-(trifluoromethyl)-1,6-dihydropyridazin-4-yl]-2,3-dihydro-1H-isoindol-5-yl]oxy)piperidin-1-yl]acetamide hydrochloride (8 mg, 0.01 mmol, 1.00 equiv), 17-[2-carboxylato-5-(2,3,5,

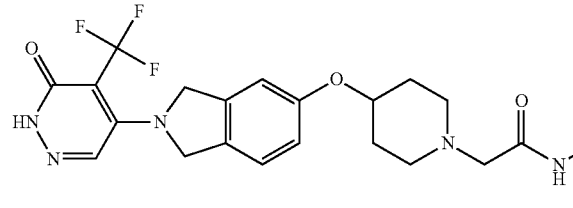
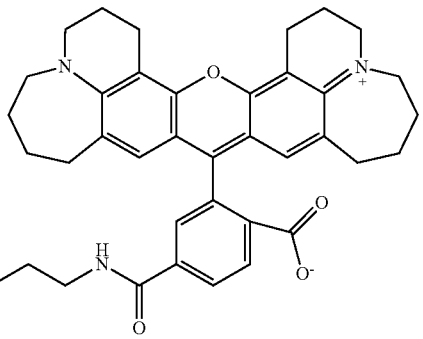

Step 1: tert-Butyl N-(6-[2-[4-([2-[6-oxo-5-(trifluoromethyl)-, 6-dihydropyridazin-4-yl]-2,3-dihydro-1H-isoindol-5-yl]oxy)piperidin-1-yl]acetamido] hexyl)carbamate A solution of 2-[4-([2-[6-oxo-5-(trifluoromethyl)-1,6-dihydropyridazin-4-yl]-2,3-dihydro-1H-isoindol-5-yl]oxy)piperidin-1-yl]acetic acid (Int-A2) (250 mg, 0.57 mmol, 1.00 equiv), tert-butyl N-(6-aminohexyl)carbamate (120 mg, 0.55 mmol, 1.00 equiv), HATU (220 mg, 0.58 mmol, 1.10 equiv), DIPEA (2 mL), and DMF (4 mL) was stirred for 0.5 h at 0° C. The residue was purified by C18 reverse phase chromatography eluting with H₂O/CH₃CN to afford 190 mg (52%) of the title compound as a white solid. LCMS: [M+H]⁺ 637.32.

Step 2: N-(6-Aminohexyl)-2-[4-([2-[6-oxo-5-(trifluoromethyl)-1,6-dihydropyridazin-4-yl]-2,3-dihydro-1H-isoindol-5-yl]oxy)piperidin-1-yl]acetamide Hydrochloride A solution of tert-butyl N-(6-[2-[4-([2-[6-oxo-5-(trifluoromethyl)-1,6-dihydropyridazin-4-yl]-2,3-dihydro-1H-

6-tetrafluorophenoxycarbonyl)phenyl]-3-oxa-9^5,25-diazaheptacyclo[18.8.1.1^5,9.0^2,18.0^4,16.0^25,29.0^14,30]triaconta-1(29),2(18),4,9(30), 14,16,19-heptaen-9-ylium (NanoBRET® 618TFP Ester) (10 mg, 0.01 mmol, 1.00 equiv), DIPEA (0.8 mL), and DMF (6 mL) was stirred for 1 h at 25° C. The resulting mixture was concentrated under reduced pressure. The crude product was purified by Prep-HPLC (XBridge Prep C18 OBD column, 5 μm, 19×150 mm column, eluting with water:acetonitrile (50:50, v:v) with 0.1% NH₄HCO₃, at a flow rate of 1.2 mL/min) to afford the title compound as a blue solid (0.8 mg, 5%). LCMS: [M+H]⁺ 1081.45.

¹H NMR (CD₃OD, 400 MHz) δ: 8.09-8.02 (m, 3H), 7.68 (d, J=1.6 Hz, 1H), 7.22 (d, J=8.4 Hz, 1H), 6.93-6.83 (m, 4H), 4.91 (s, 4H), 4.55-4.51 (m, 1H), 3.72-3.69 (m, 3H), 3.49-3.54 (m, 3H), 3.35-3.42 (m, 2H), 3.27-3.23 (m, 2H), 3.15-3.01 (m, 5H), 2.84-2.81 (m, 5H), 2.45-2.41 (m, 2H), 2.08-1.92 (m, 15H), 1.84-1.80 (m, 4H), 1.66-1.37 (m, 7H), 0.92-0.85 (m, 2H).

Example 4: Synthesis of Probe C

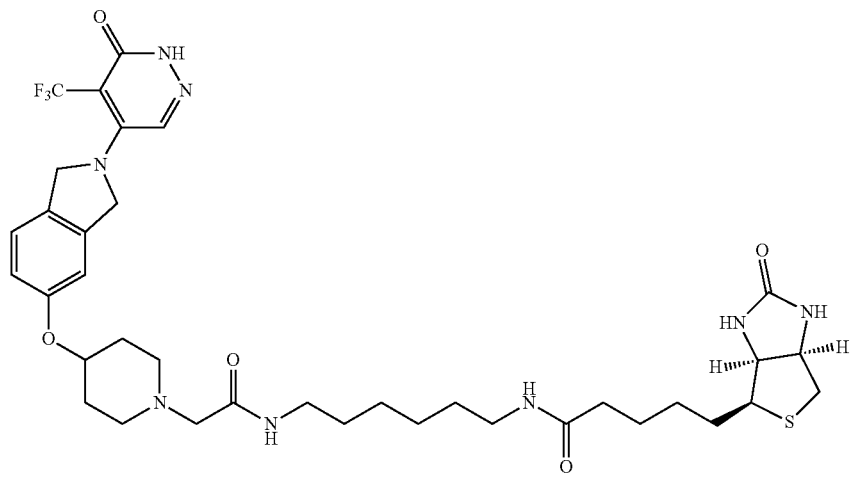 [SMILES: O=C(CCCC[C@@H]1SC[C@@H]2NC(=O)N[C@@H]21)NCCCCCCNC(=O)CN1CCC(Oc2ccc3c(c2)CN(c2cn[nH]c(=O)c2C(F)(F)F)C3)CC1]

Step 1: Tert-butyl N-(6-[5-[(3aS,4S,6aR)-2-oxo-hexahydro-1H-thieno[3,4-d]imidazolidin-4-yl]pentanamido]hexyl)carbamate A solution of 5-[(3aS,4S,6aR)-2-oxo-hexahydro-1H-thieno[3,4-d]imidazolidin-4-yl]pentanoic acid ((reagent was purchased from Beijing Dragon Rui Trading Company, 976 mg, 3.99 mmol, 1.00 equiv), DIPEA (1.55 g, 11.99 mmol, 3.00 equiv), HATU (1.82 g, 4.79 mmol, 1.20 equiv), and tert-butyl N-(6-aminohexyl)carbamate (864 mg, 3.99 mmol, 1.00 equiv) in DMF (15 mL) was stirred overnight at 25° C. The reaction was then quenched by the addition of 50 mL of water. The solids were collected by filtration to afford 1.5 g (85%) of the title compound as a white solid. LCMS: [M+H]+ 443.26.

Step 2: 5-[(3aS,4S,6aR)-2-Oxo-hexahydro-1H-thieno[3,4-d]imidazolidin-4-yl]-N-(6-aminohexyl)pentanamide Hydrochloride A solution of tert-butyl N-(6-[5-[(3aS,4S,6aR)-2-oxo-hexahydro-1H-thieno[3,4-d]imidazolidin-4-yl]pentanamido]hexyl)carbamate (800 mg, 1.81 mmol, 1.00 equiv) in hydrogen chloride/dioxane (20 mL) was stirred overnight at 25° C. The resulting mixture was concentrated under reduced pressure to afford 600 mg (88%) of the title compound as a gray crude oil. LCMS: [M+H]+ 343.21.

Step 3: 5-[(3aS,4S,6aR)-2-Oxo-hexahydro-1H-thieno[3,4-d]imidazolidin-4-yl]-N-(6-[2-[4-([2-[6-oxo-5-(trifluoromethyl)-1,6-dihydropyridazin-4-yl]-2,3-dihydro-1H-isoindol-5-yl]oxy)piperidin-1-yl]acetamido]hexyl)pentanamide A solution of 2-[4-([2-[6-oxo-5-(trifluoromethyl)-1,6-dihydropyridazin-4-yl]-2,3-dihydro-1H-isoindol-5-yl]oxy)piperidin-1-yl]acetic acid (175 mg, 0.40 mmol, 1.00 equiv), DIPEA (258 mg, 2.00 mmol, 5.00 equiv), HATU (228 mg, 0.60 mmol, 1.50 equiv), 5-[(3aS,4S,6aR)-2-oxo-hexahydro-1H-thieno[3,4-d]imidazolidin-4-yl]-N-(6-aminohexyl)pentanamide hydrochloride (228 mg, 0.60 mmol, 1.50 equiv) in DMF (3 mL) was stirred for 4 h at 25° C. The crude product was purified by C18 reverse phase chromatography eluting with H2O/CH3CN to afford the title compound as a white solid (118.3 mg, 39%). LCMS: [M+H]+ 763.35.

1H NMR (DMSO-d6, 400 MHz) δ: 12.52 (s, 1H), 7.98 (s, 1H), 7.81-7.68 (m, 2H), 7.26 (d, J=8.4 Hz, 1H), 7.00 (d, J=2.2 Hz, 1H), 6.91 (dd, J=8.4, 2.3 Hz, 1H), 6.45-6.39 (m, 1H), 6.36 (s, 1H), 4.91 (d, J=6.1 Hz, 4H), 4.45 (m, 1H), 4.26 (m, 1H), 4.17-4.08 (m, 1H), 3.14-2.96 (m, 5H), 2.91 (s, 2H), 2.82 (dd, J=12.4, 5.1 Hz, 1H), 2.73-2.63 (m, 2H), 2.58 (d, J=12.4 Hz, 1H), 2.33 (ddd, J=11.8, 9.4, 3.1 Hz, 2H), 2.11-1.90 (m, 4H), 1.76-1.54 (m, 3H), 1.57-1.20 (m, 13H).

Example 5: Synthesis of Probe D

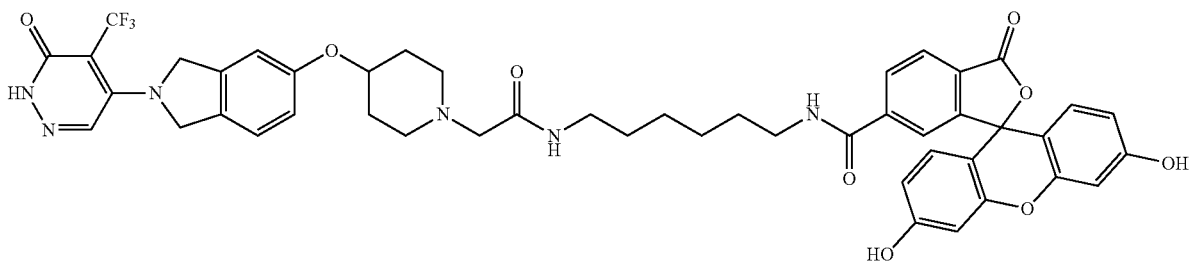 [SMILES: O=C(CN1CCC(Oc2ccc3c(c2)CN(c2cn[nH]c(=O)c2C(F)(F)F)C3)CC1)NCCCCCCNC(=O)c1ccc2c(c1)C1(OC2=O)c2ccc(O)cc2Oc2cc(O)ccc21]

Step 1: Tert-butyl 2-(4-hydroxypiperidin-1-yl)acetate

A solution of piperidin-4-ol (10.1 g, 99.85 mmol, 1.00 equiv), DIPEA (14.2 g, 109.87 mmol, 1.10 equiv), tert-butyl 2-chloroacetate (14.5 g, 96.28 mmol, 1.00 equiv) in THF (500 mL) was stirred overnight at 25° C. The solids were filtered and concentration under reduced pressure afforded the crude residue which was purified by silica gel chromatography eluting with EtOAC/petroleum ether (1/1) to afford 10.2 g (47%) of the title compound as a white solid. LCMS: [M+H]$^+$ 216.15.

Step 2: Tert-butyl 2-[4-(methanesulfonyloxy)piperidin-1-yl]acetate

A solution of tert-butyl 2-(4-hydroxypiperidin-1-yl)acetate (10.2 g, 47.38 mmol, 1.00 equiv), TEA (9.53 g, 94.18 mmol, 2.00 equiv), Ms$_2$O (9.86 g, 1.20 equiv) in DCM (200 mL) was stirred for 3 hours at 25° C. The reaction was then quenched by the addition of 300 mL of water. The resulting solution was extracted with 200 mL of dichloromethane and the organic layers were combined. The resulting mixture was concentrated under reduced pressure to afford 11 g (79%) of title compound as an off-white solid. LCMS: [M+H]$^+$ 294.13.

Step 3: Tert-butyl 2-[4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidin-1-yl]acetate A solution of 5-(5-hydroxy-2,3-dihydro-1H-isoindol-2-yl)-4-(trifluoromethyl)-2-[[2-(trimethylsilyl)ethoxy]methyl]-2,3-dihydropyridazin-3-one (4.27 g, 9.99 mmol, 1.00 equiv), potassium carbonate (6.9 g, 49.92 mmol, 5.00 equiv), tert-butyl 2-[4-(methanesulfonyloxy)piperidin-1-yl]acetate (5.86 g, 19.97 mmol, 2.00 equiv) in DMF (50 mL) was stirred for 2 days at 80° C. in an oil bath. The reaction was then quenched by the addition of 100 mL of water. The resulting solution was extracted with 4×100 mL of EtOAc and the organic layers were combined. After concentration, the residue was purified by C18 reverse phase chromatography eluting with H$_2$O/CH$_3$CN to afford 1.5 g (24%) of the title compound as a light yellow solid. LCMS: [M+H]$^+$ 625.30.

Step 4: 2-[4-([2-[6-Oxo-5-(trifluoromethyl)-1,6-dihydropyridazin-4-yl]-2,3-dihydro-1H-isoindol-5-yl]oxy)piperidin-1-yl]acetic Acid A solution of tert-butyl 2-[4-([2-[6-oxo-5-(trifluoromethyl)-1-[[2-(trimethylsilyl)ethoxy]methyl]-1,6-dihydropyridazin-4-yl]-2,3-dihydro-H-isoindol-5-yl]oxy)piperidin-1-yl]acetate (1.5 g, 2.40 mmol, 1.00 equiv) in hydrogen chloride/dioxane (40 mL) was stirred overnight at 25° C. The resulting mixture was concentrated under vacuum. The crude product was purified by C18 reverse phase chromatography eluting with H$_2$O/CH$_3$CN to afford 600 mg (57%) of the title compound as a gray solid. LCMS: [M+H]$^+$ 439.15.

Step 5: Tert-butyl N-(6-[3',6'-dihydroxy-3-oxo-3H-spiro[2-benzofuran-1,9'-xanthene]-6-ylformamido]hexyl)carbamate A solution of 3',6'-dihydroxy-3-oxo-3H-spiro[2-benzofuran-1,9'-xanthene]-6-carboxylic acid (752 mg, 2.00 mmol, 1.00 equiv), DIPEA (774 mg, 5.99 mmol, 3.00 equiv), HATU (912 mg, 2.40 mmol, 1.20 equiv), tert-butyl N-(6-aminohexyl)carbamate (475 mg, 2.20 mmol, 1.00 equiv) in DMF (10 mL) was stirred for 3 h at 25° C. The reaction was then quenched by the addition of 50 mL of water. The solids were filtered and the crude product was purified by C18 reverse phase chromatography eluting with H$_2$O/CH$_3$CN to afford 400 mg (35%) of the title compound as a yellow solid. LCMS: [M+H]$^+$ 575.23.

Step 6: N-(6-Aminohexyl)-3',6'-dihydroxy-3-oxo-3H-spiro[2-benzofuran-1,9'-xanthene]-6-carboxamide A solution of tert-butyl N-(6-[3',6'-dihydroxy-3-oxo-3H-spiro[2-benzofuran-1,9'-xanthene]-6-ylformamido]hexyl)carbamate (400 mg, 0.70 mmol, 1.00 equiv) in HCl/dioxane (20 mL) was stirred overnight at 25° C. The resulting mixture was concentrated under reduced pressure and the crude product was purified by C18 reverse phase chromatography eluting with H$_2$O/CH$_3$CN to afford 200 mg of the title compound (61%) as a yellow solid. LCMS: [M+H]$^+$ 475.18.

Step 7: N-(6-[3-Dihydroxy-3-oxo-3H-spiro[2-benzofuran-1,9'-xanthene]]-6-ylformamido]hexyl)-2-[4-([2-[6-oxo-5-(trifluoromethyl)-1,6-dihydropyridazin-4-yl]-2,3-dihydro-1H-isoindol-5-yl]oxy)piperidin-1-yl]acetamide A solution of 2-[4-([2-[6-oxo-5-(trifluoromethyl)-1,6-dihydropyridazin-4-yl]-2,3-dihydro-1H-isoindol-5-yl]oxy)piperidin-1-yl]acetic acid (Int-A2) (150 mg, 0.34 mmol, 1.00 equiv), DIPEA (176 mg, 1.36 mmol, 4.00 equiv), HATU (183 mg, 0.48 mmol, 1.40 equiv), N-(6-aminohexyl)-3-dihydroxy-3-oxo-3H-spiro[2-benzofuran-1,9'-xanthene]-6-carboxamide (228 mg, 0.48 mmol, 1.40 equiv) in DMF (5 mL) was stirred for 3 h at 25° C. After concentration, the residue was purified by C18 reverse phase chromatography eluting with H$_2$O/CH$_3$CN to afford the title compound as an orange solid (26.9 mg, 9%). LCMS: [M+H]$^+$ 895.32.

$^1$H NMR (DMSO-d$_6$, 400 MHz) δ: 8.61 (t, J=5.6 Hz, 1H), 8.14-8.02 (m, 2H), 7.96 (s, 1H), 7.72-7.61 (m, 2H), 7.22 (d, J=8.4 Hz, 1H), 6.96 (d, J=2.2 Hz, 1H), 6.86 (dd, J=8.4, 2.2 Hz, 1H), 6.58 (d, J=8.8 Hz, 4H), 6.49 (s, 2H), 4.88 (d, J=5.4 Hz, 4H), 4.34 (dp, J=8.2, 3.7 Hz, 1H), 3.17 (q, J=6.2 Hz, 2H), 3.03 (q, J=6.6 Hz, 2H), 2.86 (s, 2H), 2.70-2.58 (m, 2H), 2.33-2.22 (m, 2H), 1.91 (d, J=13.5 Hz, 2H), 1.65 (dtd, J=12.6, 8.8, 3.2 Hz, 2H), 1.39 (dq, J=27.4, 6.8, 6.2 Hz, 4H), 1.22 (d, J=6.8 Hz, 4H).

Example 6: Synthesis of Compound A

5-[5-(Piperidin-4-yloxy)-2,3-dihydro-1H-isoindol-2-yl]-4-(trifluoromethyl)-2,3-dihydropyridazin-3-one

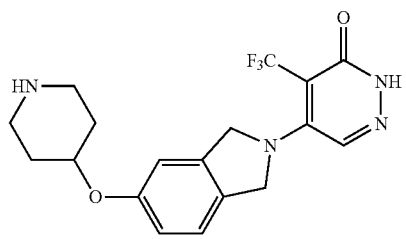 [SMILES: O=c1[nH]ncc(N2Cc3ccc(OC4CCNCC4)cc3C2)c1C(F)(F)F]

Step 1: 5-(5-Hydroxy-2,3-dihydro-1H-isoindol-2-yl)-4-(trifluoromethyl)-2-[[2-(trimethylsilyl)ethoxy]methyl]-2,3-dihydropyridazin-3-one A solution of Int-A1 (2.8 g, 8.52 mmol, 1.00 equiv), 2,3-dihydro-1H-isoindol-5-ol hydrobromide (4.27 g, 19.76 mmol, 1.00 equiv), and TEA (10 mL) in ethanol (40 mL) was stirred for 1 h at 60° C. The resulting solution was extracted with 2×100 mL of EtOAc and the organic layers combined and concentrated under reduced pressure to afford 4.5 g of the title compound as a yellow oil. LCMS: $[M+H]^+$ 428.23.

Step 2: tert-Butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate A solution of 5-(5-hydroxy-2,3-dihydro-1H-isoindol-2-yl)-4-(trifluoromethyl)-2-[[2-(trimethylsilyl)ethoxy]methyl]-2,3-dihydropyridazin-3-one (4.5 g, 10.53 mmol, 1.00 equiv), tert-butyl 4-iodopiperidine-1-carboxylate (20 g, 64.28 mmol, 8.00 equiv), potassium carbonate (15 g, 108.53 mmol, 10.00 equiv), and DMF (50 mL) was stirred for 2 days at 80° C. The resulting solution was extracted with 2×200 mL of EtOAc and the organic layers combined and concentrated under reduced pressure. The residue was applied onto a silica gel column eluting with EtOAc/petroleum ether to afford the title compound (2 g, 31%) as a yellow oil. LCMS: $[M+H]^+$ 611.15.

Step 3: 5-[5-(Piperidin-4-yloxy)-2,3-dihydro-1H-isoindol-2-yl]-4-(trifluoromethyl)-2,3-dihydropyridazin-3-one A solution of tert-butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate (150 mg, 0.25 mmol, 1.00 equiv) in HCl/dioxane (5 mL) was stirred overnight at 45° C. The resulting mixture was concentrated under reduced pressure and the crude product was purified by C18 reverse phase chromatography eluting with $H_2O$/ACN to afford the title compound as a white solid LCMS: $[M+H]^+$ 381.28. $^1$H NMR (400 MHz, Methanol-$d_4$) δ 8.05 (s, 1H), 7.27 (d, J=8.4 Hz, 1H), 7.02-6.91 (m, 2H), 5.00 (d, J=10.6 Hz, 4H), 4.61-4.48 (m, 1H), 3.21-3.10 (m, 2H), 2.89-2.78 (m, 2H), 2.11-2.08 (m, 2H), 1.82-1.69 (m, 2H).

Example 7: Synthesis of Compound B

6-[4-[(3-[[(1S)-2-[6-Oxo-5-(trifluoromethyl)-1,6-dihydropyridazin-4-yl]-2,3-dihydro-1H-isoindol-1-yl]methoxy]phenyl)carbonyl]piperazin-1-yl]pyridine-3-carbonitrile

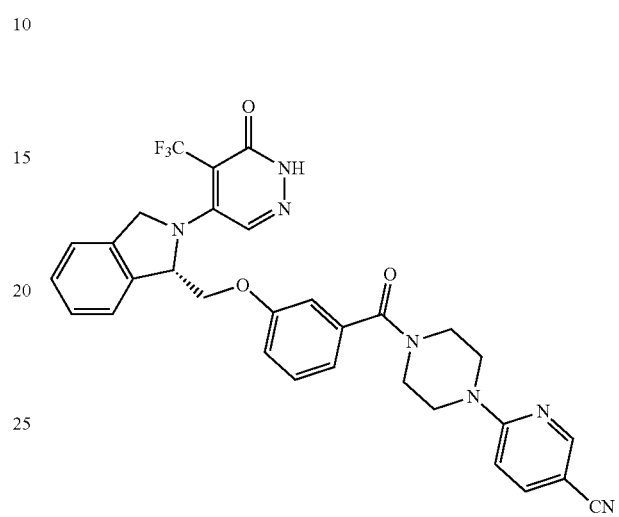

Step 1: 5-[1-(Hydroxymethyl)-2,3-dihydro-1H-isoindol-2-yl]-4-(trifluoromethyl)-2-[[2-(trimethylsilyl)ethoxy]methyl]-2,3-dihydropyridazin-3-one A solution of 5-chloro-4-(trifluoromethyl)-2-[2-(trimethylsilyl)ethoxy]methyl-2,3-dihydropyridazin-3-one (4.8 g, 14.60 mmol, 1.00 equiv), 2,3-dihydro-1H-isoindol-1-ylmethanol hydrochloride (2.7 g, 14.54 mmol, 1.00 equiv) and TEA (4.4 g, 43.48 mmol, 2.99 equiv) in ethanol (100 mL) was stirred for 1 h at 60° C., and then the resulting solution was concentrated under vacuum and the residue was applied onto a silica gel column eluting with EtOAc/petroleum ether (45:55) to afford 2.9 g (45%) of the title compound as a brown solid. LCMS: $[M+H]^+$ 442.17.

Step 2: Methyl 3-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)benzoate Under nitrogen, a solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (2.93 g, 6.64 mmol, 1.00 equiv), methyl 3-bromobenzoate (2.84 g, 13.21 mmol, 1.99 equiv), Pd(allyl)$Cl_2$ (243 mg), Rockphos (311 mg) and $Cs_2CO_3$ (4.3 g, 13.20 mmol, 1.99 equiv) in Toluene (100 mL) was stirred for 18 h at 80° C. The resulting solution was concentrated under vacuum and then the residue was applied onto a silica gel column eluting with EtOAc/petroleum ether (1:3) to afford 3 g (79%) of the title compound as a brown solid. LCMS: $[M+H]^+$ 576.21.

Step 3: 3-([2-[6-Oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)benzoic Acid A solution of methyl 3-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)benzoate (1.15 g, 2.00 mmol, 1.00 equiv) and LiOH (240 mg, 10.02 mmol, 5.02 equiv) in THF (12 mL) and water (3 mL) was stirred for 3 h at 60° C. The resulting solution was concentrated under vacuum and the residue was diluted with 10 mL of H$_2$O, and then the pH value of the solution was adjusted to 5 with HCl (36.5%). The solid was collected by filtration to afford 1.1 g (98%) of the title compound as a light yellow solid. LCMS: [M+H]$^+$ 562.19.

Step 4: 3-([2-[6-Oxo-5-(trifluoromethyl)-1,6-dihydropyridazin-4-yl]-2,3-dihydro-1H-isoindol-1-yl]methoxy)benzoic Acid A solution of 3-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)benzoic acid (1.1 g, 1.96 mmol, 1.00 equiv) in HCl/dioxane (20 mL, 4M) was stirred for 3 h at RT, and then the resulting solution was concentrated under vacuum to afford 1 g of the title compound as a crude brown solid. LCMS: [M+H]$^+$ 432.11.

Step 5: 6-[4-[(3-[[(1R)-2-[6-oxo-5-(trifluoromethyl)-1,6-dihydropyridazin-4-yl]-2,3-dihydro-1H-isoindol-1-yl]methoxy]phenyl)carbonyl]piperazin-1-yl]pyridine-3-carbonitrile and 6-[4-[(3-[[(1S)-2-[6-oxo-5-(trifluoromethyl)-1,6-dihydropyridazin-4-yl]-2,3-dihydro-1H-isoindol-1-yl]methoxy]phenyl)carbonyl]piperazin-1-yl]pyridine-3-carbonitrile A solution of 3-([2-[6-oxo-5-(trifluoromethyl)-1,6-dihydropyridazin-4-yl]-2,3-dihydro-1H-isoindol-1-yl]methoxy)benzoic acid (500 mg, 1.16 mmol, 1.00 equiv), HATU (528 mg, 1.39 mmol, 1.20 equiv), DIPEA (449 mg, 3.47 mmol, 3.00 equiv) and Int-A4 (240 mg, 1.27 mmol, 1.1 equiv) in DMF (5 mL) was stirred for 2 h at RT. After concentration by reduced pressure, the resulting solution was purified by C18 reverse phase chromatography eluting with H$_2$O/ACN. The residue was further purified by Prep-HPLC and Chiral-Prep-HPLC (CHIRAL Repaired IA, 5 μm, 0.46×10 cm column, eluting with a gradient of (Hexanes:DCM=3:1) (0.1% DEA):EtOH=50:50, at a flow rate of 1 mL/min) yielding the title compound as a white solid. The absolute stereochemistry was assigned based on an X-ray crystal structure which confirmed (S)-absolute stereochemistry.

LCMS: [M+H]$^+$ 602.05, $^1$H NMR (300 MHz, Methanol-d$_4$) δ 8.43 (d, J=1.8 Hz, 1H), 8.42 (s, 1H), 7.79 (dd, J=9.0, 2.4 Hz, 1H), 7.53-7.50 (m, 1H), 7.41-7.35 (m, 4H), 7.05-6.99 (m, 2H), 6.94-6.87 (m, 2H), 6.20 (s, 1H), 5.33 (d, J=14.8 Hz, 1H), 4.68 (d, J=14.7 Hz, 1H), 4.53 (dd, J=10.2, 3.3 Hz, 1H), 4.29 (dd, J=10.2, 6.6 Hz, 1H), 3.91-3.44 (m, 8H). tR=5.955 min.

Example 8: Synthesis of Compound C

5-[2-[(1-Acetylpiperidin-4-yl)oxy]-5H,6H,7H-pyrrolo[3,4-b]pyridin-6-yl]-4-(trifluoromethyl)-2,3-dihydropyridazin-3-one

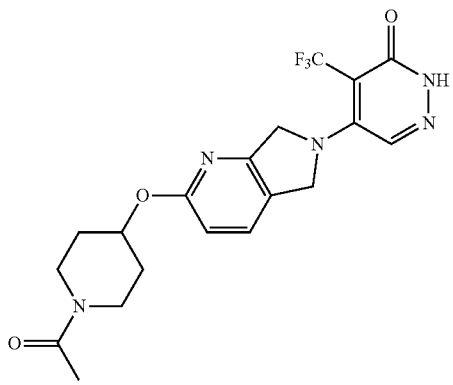 [SMILES: CC(=O)N1CCC(Oc2ccc3c(n2)CN(c2cn[nH]c(=O)c2C(F)(F)F)C3)CC1]

Step 1: 5-[2-Chloro-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one A solution of 2-chloro-5H,6H,7H-pyrrolo[3,4-b]pyridin-6-yl hydrochloride (5 g, 26.31 mmol, 1.00 equiv), TEA (8 g, 79.06 mmol, 3.00 equiv), and Int-A1 (14.3 g, 43.49 mmol, 1.00 equiv) in EtOH (30 mL) was stirred for 2 h at 80° C. After concentration under reduced pressure, the residue was applied onto a silica gel column with EtOAc/petroleum ether (1:4) to afford 9.3 g (79%) of title compound as a yellow oil. LCMS: [M+H]$^+$ 447.15.

Step 2: 5-[2-Hydroxy-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one A solution of 5-[2-chloro-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one (300 mg, 0.67 mmol, 1.00 equiv), tBuBrettphos (49 mg, 0.15 equiv), K$_3$PO$_4$ (427 mg, 2.01 mmol, 3.00 equiv), and Pd(OAc)$_2$ (15 mg, 0.07 mmol, 0.10 equiv) in dioxane (5 mL) and water (0.5 mL) was stirred for 2 h at 80° C. in an oil bath under N$_2$ atmosphere. After concentration, the residue was applied onto a silica gel column with DCM/methanol (85:15) to afford 200 mg (70%) of title compound as a yellow oil. LCMS: [M+H]$^+$ 429.15

Step 3: Tert-butyl 4-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-2-yl]oxy)piperidine-1-carboxylate A solution of 5-[2-hydroxy-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one (200 mg, 0.47 mmol, 1.00 equiv), Ag$_2$CO$_3$ (247 mg, 2.00 equiv), and tert-butyl 4-iodopiperidine-1-carboxylate (416 mg, 1.34 mmol, 3.00 equiv) in DMF (15 mL) was stirred for 4 h at 80° C. The resulting solution was extracted with 3×10 mL of EtOAc and the organic layers combined. After concentration, the residue was applied onto a silica gel column with EtOAc/petroleum ether (1:9) to afford 150 mg (53%) of title compound as a yellow oil. LCMS: [M+H]$^+$ 612.30.

Step 4: 5-[2-(Piperidin-4-yloxy)-5H,6H,7H-pyrrolo[3,4-b]pyridin-6-yl]-4-(trifluoromethyl)-2,3-dihydropyridazin-3-one A solution of tert-butyl 4-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-2-yl]oxy)piperidine-1-carboxylate (150 mg, 0.25 mmol, 1.00 equiv) in HCl/dioxane (15 mL, 4M) was stirred overnight at 25° C. The pH value of the solution was adjusted to 8 with ammonia (100%). The crude product was purified by Prep-HPLC to afford 64.8 mg (69%) of title compound as a white solid. LCMS: [M+H]$^+$ 382.15 [M+H].

Step 5: 5-[2-[(1-Acetylpiperidin-4-yl)oxy]-5H,6H,7H-pyrrolo[3,4-b]pyridin-6-yl]-4-(trifluoromethyl)-2,3-dihydropyridazin-3-one A solution of 5-[2-(piperidin-4-yloxy)-5H,6H,7H-pyrrolo[3,4-b]pyridin-6-yl]-4-(trifluoromethyl)-2,3-dihydropyridazin-3-one (300 mg, 0.79 mmol, 1.00 equiv), TEA (239 mg, 2.36 mmol, 3.00 equiv), and EtOAc (160 mg, 1.57 mmol, 2.00 equiv) in DCM (15 mL) was stirred for 1 h at 25° C. The resulting solution was quenched by 20 mL of water and extracted with 3×15 mL of DCM and the organic layers combined. After concentration, the crude product was purified by Flash-Prep-HPLC to afford 70.2 mg (21%) of title compound as a white solid. LCMS: [M+H]$^+$ 424.15 $^1$H NMR (400 MHz, Methanol-d$_4$) δ 8.07 (s, 1H), 7.69 (d, J=8.4 Hz, 1H), 6.76 (d, J=8.4 Hz, 1H), 5.39-5.28 (m, 1H), 5.03 (s, 2H), 4.92 (s, 2H), 3.97-3.89 (m, 1H), 3.86-3.75 (m, 1H), 3.57-3.44 (m, 2H), 2.15 (s, 3H), 2.14-1.97 (m, 2H), 1.89-1.70 (m, 2H).

Example 9: In Vitro Assays

Recombinant PARP Enzymes

A portion of TIPARP (residues 456 to 657 of NP_056323.2 (SEQ ID NO: 1), GenBank Accession No. NM_015508.4) was overexpressed in *E. coli* cells. An N-terminal fusion tag, MHHHHHHSSGVDLGTENLYFQSNAGLNDIFEAQKIEWHE (SEQ ID NO: 7), was used to purify the protein from cell lysates. The fusion tag was left on the protein for use in the probe displacement assay.

A portion of PARP10 (residues 808 to 1025 of NP_116178.2 (SEQ ID NO: 2), GenBank Accession No. NM_032789.4) was overexpressed in *E. coli* cells. An N-terminal fusion tag, MAHHHHHHENLYFQSM (SEQ ID NO: 8), was used to purify the protein from cell lysates. The fusion tag was left on the protein for use in the probe displacement assay.

A portion of PARP12 (residues 489 to 684 of NP_073587.1 (SEQ ID NO: 3), GenBank Accession No. NM_022750.3) was overexpressed in Sf9 cells. An N-terminal fusion tag, MAHHHHHHENLYFQSM (SEQ ID NO: 8), was used to purify the protein from cell lysates. The fusion tag was left on the protein for use in the probe displacement assay.

A portion of PARP14 (residues 1611 to 1801 of NP_060024.2 (SEQ ID NO: 4), GenBank Accession No. NM_017554) was overexpressed in *E. coli* cells. An N-terminal fusion tag, MHHHHHHSSGVDLGTENLYFQSNA (SEQ ID NO: 9), was used to purify the protein from cell lysates. The fusion tag was left on the protein for use in the probe displacement assay.

A portion of PARP15 (residues 481 to 678 of NP_689828.1 (SEQ ID NO: 5), GenBank Accession No. NM_152615) was overexpressed in Sf9 cells. An N-terminal fusion tag, MAHHHHHHSSGVDLGTENLYFQSM (SEQ ID NO: 10), was used to purify the protein from cell lysates. The fusion tag was left on the protein for use in the probe displacement assay.

A portion of PARP16 (residues 5 to 279 of NP_060321.3 (SEQ ID NO: 6), GenBank Accession No. NM_017851) was overexpressed in *E. coli* cells. An N-terminal fusion tag, MHHHHHHSSGVDLGTENLYFQSNA (SEQ ID NO: 9), was used to purify the protein from cell lysates. The fusion tag was left on the protein for use in the probe displacement assay.

In Vitro Probe Displacement Assay for Assessing Binding of Inhibitors to TIPARP, PARP10, PARP14 and PARP16

Displacement of a Probe C binding to monoPARP active sites was measured using a time-resolved fluorescence resonance energy transfer (TR-FRET) assay. 20 nL of a dose response curve of each test compound was spotted in black 384-well polystyrene proxiplates (Perkin Elmer) using a Mosquito (TTP Labtech). Reactions were performed in an 8 μL volume by adding 6 μL of the monoPARP and Probe C in assay buffer (20 mM HEPES pH=8, 100 mM NaCl, 0.1% bovine serum albumin, 2 mM DTT and 0.002% Tween20), incubating with test compound at 25° C. for 30 min, then adding 2 μL of ULight-anti 6xHis and LANCE Eu-W 1024 labeled streptavidin (Perkin Elmer). The final concentrations of monoPARP, Probe C, ULight-anti 6xHis and LANCE Eu-W1024 labeled streptavidin are listed in Table 3. Binding reactions were equilibrated at 25° C. for an additional 30 min, then read on an Envision platereader equipped with a LANCE/DELFIA top mirror (Perkin Elmer) using excitation of 320 nm and emission of 615 nm and 665 nM with a 90 μs delay. The ratio of the 665/615 nm emission were calculated for each well to determine the amount of complex of monoPARP and Probe C in each well.

TABLE 3

Assay conditions for monoPARP probe displacement assays where the streptavidin is labeled with TR-FRET donor

| Target | Enzyme (nM) | Probe C (nM) | ULight-anti 6xHis (nM) | LANCE Eu-W1024 labeled streptavidin (nM) |
| --- | --- | --- | --- | --- |
| TIPARP | 6 | 2 | 4 | 0.25 |
| PARP10 | 6 | 0.5 | 2 | 0.25 |
| PARP14 | 6 | 2 | 10 | 0.25 |
| PARP16 | 3 | 1 | 6 | 0.25 |

In Vitro Probe Displacement Assay for Assessing Binding of Inhibitors to PARP12 and PARP15

Displacement of a Probe C binding to monoPARP active sites was measured using a time-resolved fluorescence resonance energy transfer (TR-FRET) assay. 20 nL of a dose response curve of each test compound was spotted in black 384-well polystyrene proxiplates (Perkin Elmer) using a Mosquito (TTP Labtech). Reactions were performed in a 8 μL volume by adding 6 μL of the monoPARP and Probe C in assay buffer (20 mM HEPES pH=8, 100 mM NaCl, 0.1% bovine serum albumin, 2 mM DTT and 0.002% Tween20), incubating with test compound at 25° C. for 30 min, then adding 2 μL of ULight-streptavidin and LANCE Eu-W 1024

Anti-6×His (Perkin Elmer). The final concentrations of monoPARP, Probe C, ULight-streptavidin and LANCE Eu-W1024 Anti-6×His are listed in Table 4. Binding reactions were equilibrated at 25° C. for an additional 30 min, then read on an Envision platereader equipped with a LANCE/DELFIA top mirror (Perkin Elmer) using excitation of 320 nm and emission of 615 nm and 665 nM with a 90 μs delay. The ratio of the 665/615 nm emission were calculated for each well to determine the amount of complex of monoPARP and Probe C in each well.

TABLE 4

Assay conditions for monoPARP probe displacement assays where the anti-His antibody is labeled with TR-FRET donor

| Target | Enzyme (nM) | Probe C (nM) | ULight-labeled streptavidin (nM) | LANCE Eu-W1024 anti 6xHis (nM) |
|---|---|---|---|---|
| PARP12 | 6 | 32 | 10 | 1.25 |
| PARP15 | 1.5 | 8 | 2 | 0.5 |

Data Analysis for all In Vitro Assays

Control wells containing a negative control of 0.25% DMSO vehicle or a positive control of 100 μM Compound A were used to calculate the % inhibition as described below:

$$\% \text{ inhibition} = 100 \times \frac{TRF_{cmpd} - TRF_{min}}{TRF_{max} - TRF_{min}}$$

where $TRF_{cmpd}$ is the TR-FRET ratio from the compound treated well, $TRF_{min}$ is the TR-FRET ratio from the Compound A-treated positive control well and $TRF_{max}$ is the TR-FRET ratio from the DMSO-treated negative control well.

The % inhibition values were plotted as a function of compound concentration and the following 4-parameter fit was applied to derive the $IC_{50}$ values:

$$Y = \text{Bottom} + \frac{(\text{Top} - \text{Bottom})}{\left(1 + \left(\frac{X}{IC_{50}}\right)^{\text{Hill Coefficient}}\right)}$$

where top and bottom are normally allowed to float, but may be fixed at 100 or 0 respectively in a 3-parameter fit. The Hill Coefficient is normally allowed to float but may also be fixed at 1 in a 3-parameter fit. Y is the % inhibition and X is the compound concentration.

Validation of In Vitro Probe Displacement Assays

The probe displacement assays were validated by outcompeting Probe C with Compound A, an analog that does not contain a linker or biotin group. The assays for TIPARP, PARP10, PARP12, PARP14, PARP15 and PARP16 were set up as described above, and the results are shown in FIGS. 4A-4F.

FIGS. 4A-4F are validation results of the in vitro probe displacement binding assays. Dose response curves for Compound A were generated using each assay to confirm that Probe C was able to be outcompeted from the monoPARP enzyme. $IC_{50}$ values were TIPARP=7 nM, PARP10=80 nM, PARP12=200 nM, PARP14=50 nM, PARP15=60 nM and PARP16=100 nM.

Example 10: Live Cell Assays

NanoLuc Plasmids

MonoPARP genes from Table 5 were cloned into the pcDNA3.1-mammalian expression vector as a NanoLuc fusion with NanoLuc on the N- or C-terminus as indicated. The sequence of the NanoLuc tag is as follows:

NanoLuc amino acid sequence (SEQ ID NO: 11):
MVFTLEDFVGDWRQTAGYNLDQVLEQGGVSSLFQNLGVSVTPIQRIVLS

GENGLKIDIHVIIPYEGLSGDQMGQIEKIFKVVYPVDDHHFKVILHYGTL

VIDGVTPNMIDYFGRPYEGIAVFDGKKITVTGTLWNGNKIIDERLINPDG

SLLFRVTINGVTGWRLCERILA

NanoLuc nucleic acid sequence (SEQ ID NO: 12):
atggtcttcacactcgaagatttcgttggggactggcgacagacagccgg ctacaacctggaccaagtccttgaacagggaggtgtgtccagtttgtttc agaatctcggggtgtccgtaactccgatccaaaggattgtcctgagcggt gaaaatgggctgaagatcgacatccatgtcatcatcccgtatgaaggtct gagcggcgaccaaatgggccagatcgaaaaaattttaaggtggtgtacc ctgtggatgatcatcactttaaggtgatcctgcactatggcacactggta atcgacggggttacgccgaacatgatcgactatttcggacggccgtatga aggcatcgccgtgttcgacggcaaaaagatcactgtaacagggaccctgt ggaacggcaacaaaattatcgacgagcgcctgatcaacccgacggctcc ctgctgttccgagtaaccatcaacggagtgaccggctggcggctgtgcga acgcattctggcgtaa

TABLE 5

Details for the monoPARP-NanoLuc fusion genes used

| Plasmid Name | Genbank Accession Number | Amino Acid Residues | NanoLuc Position |
|---|---|---|---|
| Full-length TIPARP | NM_015508 | 1-657 of NP_056323.2 (SEQ ID NO: 1) | C-terminus |
| Catalytic domain TIPARP | NM_015508 | 456-657 of NP_056323.2 (SEQ ID NO: 1) | C-terminus |
| PARP10 | NM_032789 | 808-1025 of NP_116178.2 (SEQ ID NO: 2) | C-terminus |
| PARP12 | NM_022750.3 | 489-684 of NP_073587.1 (SEQ ID NO: 3) | C-terminus |
| PARP14 | NM_017554 | 1611-1801 of NP_060024.2 (SEQ ID NO: 4) | N-terminus |

NanoBRET Probe Displacement Assay for Assessing Binding of Inhibitors to TIPARP, PARP10, PARP12 and PARP14

Displacement of a fluorescently-labeled compound Probe A binding to NanoLuc-tagged monoPARP enzymes was measured in live cells using a bioluminescence resonance energy transfer (NanoBRET) assay. TIPARP, PARP10, PARP12 or PARP14 fused to a NanoLuc tag were overexpressed in 293T cells (ATCC) using the plasmids described herein. Plasmid DNA and empty vector DNA were added to phenol red free OptiMEM (Thermo Fisher) as shown in Table 6 in a total volume of 2.456 mL. 157 µL of Fugene HD (Promega) was added to the DNA mixture and allowed to incubate 5 min at 25° C.

TABLE 6

| Plasmid Name | Concentration of Plasmid (µg/mL) | Concentration of Empty Vector (µg/mL) | Probe A (nM) |
|---|---|---|---|
| Full-length TIPARP | 0.2 | 19.8 | 9 |
| Catalytic domain TIPARP | 0.2 | 19.8 | 80 |
| PARP10 | 2 | 18 | 7 |
| PARP12 | 2 | 18 | 300 |
| PARP14 | 0.2 | 19.8 | 100 |

Next, 2.375 mL of the plasmid-Fugene mixture were added to 20 million 293T cells in DMEM (Thermo Fisher) supplemented with 10% FBS (VWR). The transfection was incubated for 24 h at 37° C. in an incubator containing air supplemented with 5% $CO_2$. The cells were resuspended in phenol red free OptiMEM media. Transfected 293T cells were diluted to 500,000 cells per mL and Probe A was added to a final concentration as shown in Table 6. 40 µL of cells were then added to white polystyrene 384-well non-binding surface microplate (Corning). 40 nL of a dose response curve diluted in DMSO of each test compound was added to the cell plate using a Mosquito (TTP Labtech) and the plate was incubated at 37° C. in an incubator containing air supplemented with 5% $CO_2$ for 2 h. The assay plate was allowed to equilibrate to room temperature (25° C.), then 20 µL per well of NanoBRET substrate (Promega) was added to the plate (1:166 dilution of NanoBRET substrate, 1:500 dilution of NanoLuc extracellular inhibitor in OptiMEM without phenol red). Filtered luminescence was measured on an Envision (Perkin Elmer) equipped with a dual 585 nm mirror, 460±40 nm bandpass filter (donor) and 610±50 nm longpass filter (acceptor).

TABLE 7

| Assay | Positive control compound | Final Concentration (µM) |
|---|---|---|
| Full-length TIPARP | Compound B | 0.1 |
| Catalytic domain TIPARP | Compound B | 0.2 |
| PARP10 | Compound C | 2 |
| PARP12 | Compound B | 1 |
| PARP14 | Compound D | 5 |

Data Analysis for NanoBRET Assays

BRET ratio was measured as shown below:

$$BRET \text{ ratio} = \frac{\text{Emission at 610 nm}}{\text{Luminescence}}$$

Control wells containing a negative control of 0.2% DMSO vehicle or a positive control were used to calculate the % inhibition as described below:

$$\% \text{ inhibition} = 100 \times \frac{BRET \text{ ratio}_{cmpd} - BRET \text{ ratio}_{min}}{BRET \text{ ratio}_{max} - BRET \text{ ratio}_{min}}$$

where BRET ratio$_{cmpd}$ is the BRET ratio from the compound treated well, BRET ratio$_{min}$ is the BRET ratio from the positive control wells and BRET ratio$_{max}$ is the BRET ratio from the DMSO treated negative control well.

The % inhibition values were plotted as a function of compound concentration and the following 4-parameter fit was applied to derive the IC$_{50}$ values:

$$Y = \text{Bottom} + \frac{(\text{Top} - \text{Bottom})}{\left(1 + \left(\frac{X}{IC_{50}}\right)^{\text{Hill Coefficient}}\right)}$$

where top and bottom are normally allowed to float, but may be fixed at 100 or 0 respectively in a 3-parameter fit. The Hill Coefficient is normally allowed to float but may also be fixed at 1 in a 3-parameter fit. Y is the % inhibition and X is the compound concentration.

Validation of NanoBRET Probe Displacement Assays

The probe displacement assays were validated by outcompeting Probe A with Compound A in the PARP14 NanoBRET assay, Compound B in the TIPARP NanoBRET assay, Compound C in the PARP10 NanoBRET assay and Compound B in the PARP12 NanoBRET assay. The compounds used to test the probe displacement of Probe A are analogs that do not contain a linker or fluorescent tag. The assays for TIPARP full-length and catalytic domain, PARP10, PARP12 and PARP14 were set up as described above, and the results are shown in FIG. 5.

FIGS. 5A-5D are validation results of the NanoBRET probe displacement binding assays. Dose response curves for control compounds were generated using each assay to confirm that Probe A was able to be outcompeted from the monoPARP enzyme. IC$_{50}$ values were full-length TIPARP Compound B=4 nM, catalytic domain TIPARP Compound B=7 nM, PARP10 Compound C=4 nM, PARP12 Compound B=170 nM, PARP14 compound A=30 nM.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Leidecker, O.; Bonfiglio, J. J.; Colby, T.; Zhang, Q.; Atanassov, I.; Zaja, R.; Palazzo, L.; Stockum, A.; Ahel, I.; Matic, I., Serine is a new target residue for endogenous ADP-ribosylation on histones. *Nat Chem Biol* 2016, 12 (12), 998-1000.
2. Belousova, E. A.; Ishchenko capital A, C.; Lavrik, O. I., Dna is a New Target of Parp3. *Sci Rep* 2018, 8 (1), 4176.
3. Yamada, T.; Horimoto, H.; Kameyama, T.; Hayakawa, S.; Yamato, H.; Dazai, M.; Takada, A.; Kida, H.; Bott, D.; Zhou, A. C.; Hutin, D.; Watts, T. H.; Asaka, M.; Matthews, J.; Takaoka, A., Constitutive aryl hydrocarbon receptor signaling constrains type I interferon-mediated antiviral innate defense. *Nat Immunol* 2016, 17 (6), 687-94.
4. Caprara, G.; Prosperini, E.; Piccolo, V.; Sigismondo, G.; Melacarne, A.; Cuomo, A.; Boothby, M.; Rescigno, M.; Bonaldi, T.; Natoli, G., PARP14 Controls the Nuclear Accumulation of a Subset of Type I IFN-Inducible Proteins. *J Immunol* 2018, 200 (7), 2439-2454.
5. Zaffini, R.; Gotte, G.; Menegazzi, M., Asthma and poly (ADP-ribose) polymerase inhibition: a new therapeutic approach. *Drug Des Devel Ther* 2018, 12, 281-293.
6. Jwa, M.; Chang, P., PARP16 is a tail-anchored endoplasmic reticulum protein required for the PERK- and IRE1alpha-mediated unfolded protein response. *Nat Cell Biol* 2012, 14 (11), 1223-30.
7. Barbarulo, A.; Iansante, V.; Chaidos, A.; Naresh, K.; Rahemtulla, A.; Franzoso, G.; Karadimitris, A.; Haskard, D. O.; Papa, S.; Bubici, C., Poly(ADP-ribose) polymerase family member 14 (PARP14) is a novel effector of the JNK2-dependent pro-survival signal in multiple myeloma. *Oncogene* 2013, 32 (36), 4231-42.
8. Thorsell, A. G.; Ekblad, T.; Karlberg, T.; Low, M.; Pinto, A. F.; Tresaugues, L.; Moche, M.; Cohen, M. S.; Schuler, H., Structural Basis for Potency and Promiscuity in Poly (ADP-ribose) Polymerase (PARP) and Tankyrase Inhibitors. *J Med Chem* 2017, 60 (4), 1262-1271.
9. Copeland, R. A., Evaluation of enzyme inhibitors in drug discovery. A guide for medicinal chemists and pharmacologists. *Methods Biochem Anal* 2005, 46, 1-265.
10. Wahlberg, E.; Karlberg, T.; Kouznetsova, E.; Markova, N.; Macchiarulo, A.; Thorsell, A. G.; Pol, E.; Frostell, A.; Ekblad, T.; Oncu, D.; Kull, B.; Robertson, G. M.; Pellicciari, R.; Schuler, H.; Weigelt, J., Family-wide chemical profiling and structural analysis of PARP and tankyrase inhibitors. *Nat Biotechnol* 2012, 30 (3), 283-8.
11. Davis, B. J.; Erlanson, D. A., Learning from our mistakes: the 'unknown knowns' in fragment screening. *Bioorg Med Chem Lett* 2013, 23 (10), 2844-52.

---

What is claimed is:

1. A method of identifying an inhibitor for Poly (ADP-ribose) polymerase (PARP), the method comprising:
   combining (i) a polypeptide comprising a PARP catalytic domain wherein the polypeptide is labeled with a donor fluorophore, (ii) a PARP probe, wherein the PARP probe is labeled with an acceptor fluorophore or an affinity tag, and (iii) a test compound,
   wherein if the PARP probe is labeled with an affinity tag then an acceptor fluorophore is attached to a molecule that binds to the affinity tag and the molecule is combined with (i)-(iii);
   exposing the donor fluorophore to excitation light;
   measuring a signal produced by the acceptor fluorophore; and
   identifying the test compound as an inhibitor for PARP based on the signal produced by the acceptor fluorophore;

wherein the PARP probe has a structure according to Formula (I):
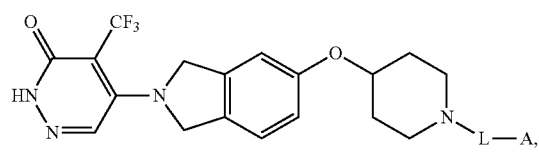
or a salt thereof,
wherein:
L is a linking group having 5-30 spacer atoms selected from C, N, O, and S connecting the N atom of the piperidinyl group of Formula (I) with group A; and
A is the acceptor fluorophore or the affinity tag.
2. The method of claim 1, wherein the PARP probe is a compound having the structure:
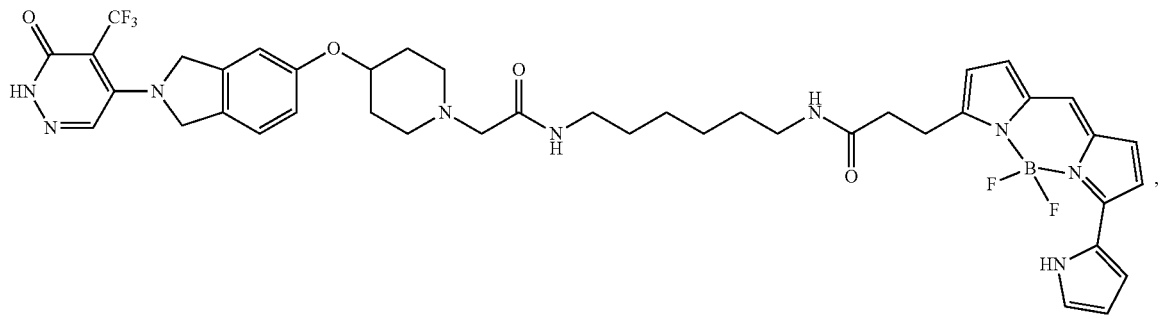
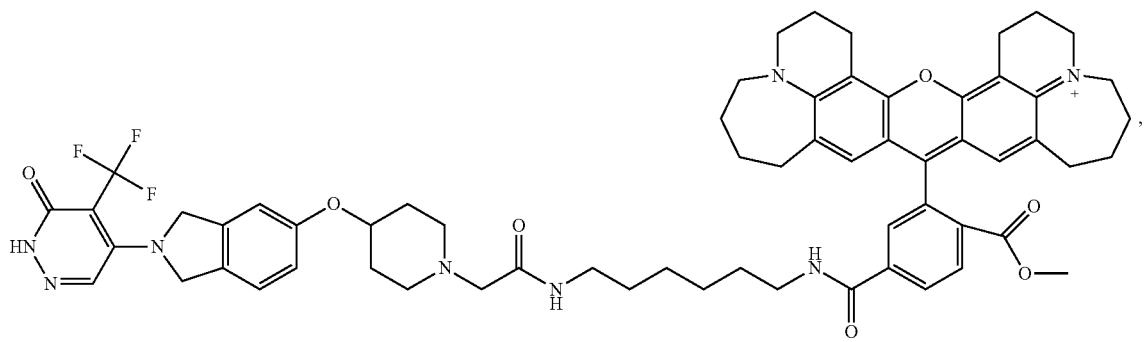
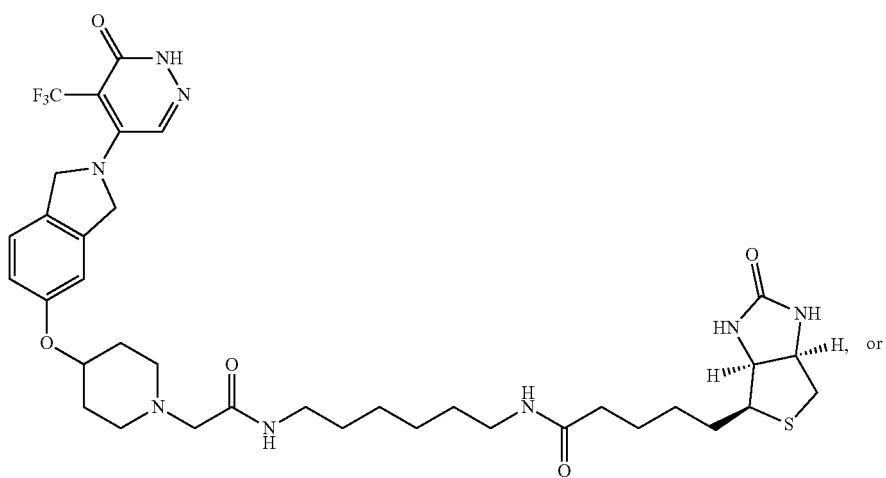

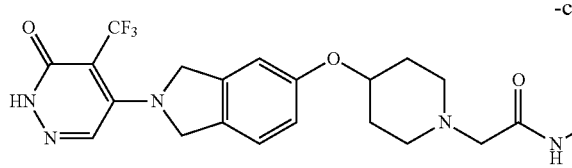

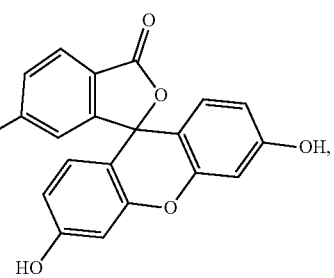

or a salt thereof.

3. The method of claim 1, further comprising identifying the test compound as an inhibitor for PARP if the signal produced by the acceptor fluorophore is decreased as compared to a reference level.

4. The method of claim 1, wherein the PARP is PARP1, PARP2, PARP3, PARP4, PARP5a, PARP5b, PARP6, TIPARP, PARP8, PARP9, PARP10, PARP11, PARP12, PARP13, PARP14, PARP15, or PARP16.

5. The method of claim 1, wherein the PARP probe is biotinylated, and the acceptor fluorophore is attached to streptavidin.

6. The method of claim 1, wherein the polypeptide comprises a polyhistidine tag.

7. A method of identifying an inhibitor for Poly (ADP-ribose) polymerase (PARP), the method comprising:
   combining (i) a polypeptide comprising a PARP catalytic domain, wherein the polypeptide is labeled with an acceptor fluorophore; (ii) a PARP probe, wherein the PARP probe is labeled with a donor fluorophore or an affinity tag, and (iii) a test compound,
   wherein if the PARP probe is labeled with an affinity tag then a donor fluorophore is attached to a molecule that binds to the affinity tag and the molecule is combined with (i)-(iii);
   exposing the donor fluorophore to excitation light;
   measuring a signal produced by the acceptor fluorophore in the presence of a test compound; and
   identifying the test compound as an inhibitor for PARP based on the signal produced by the acceptor fluorophore;
   wherein the PARP probe has a structure according to Formula (I):

(I)

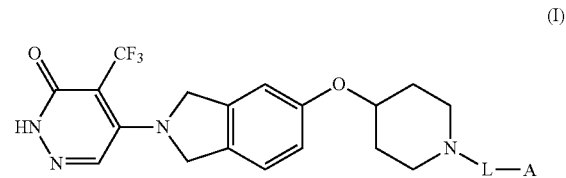

or a salt thereof,
wherein:
L is a linking group having 5-30 spacer atoms selected from C, N, O, and S connecting the N atom of the piperidinyl group of Formula (I) with group A; and
A is the acceptor fluorophore or the affinity tag.

8. The method of claim 7, wherein the PARP probe is a compound having the structure:

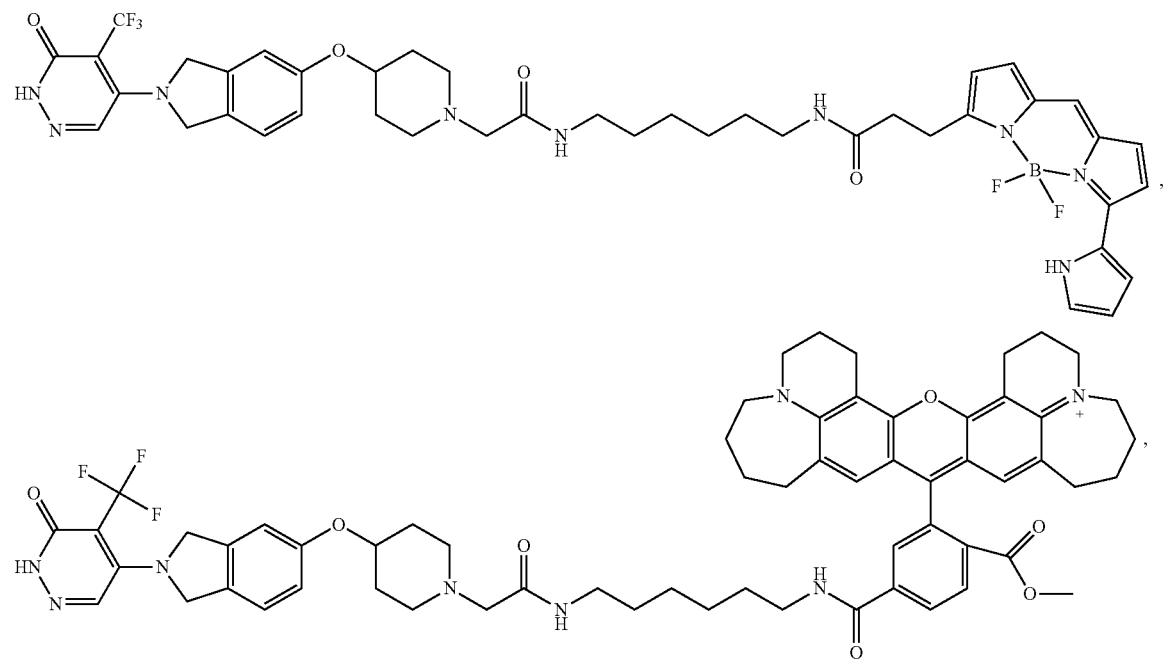

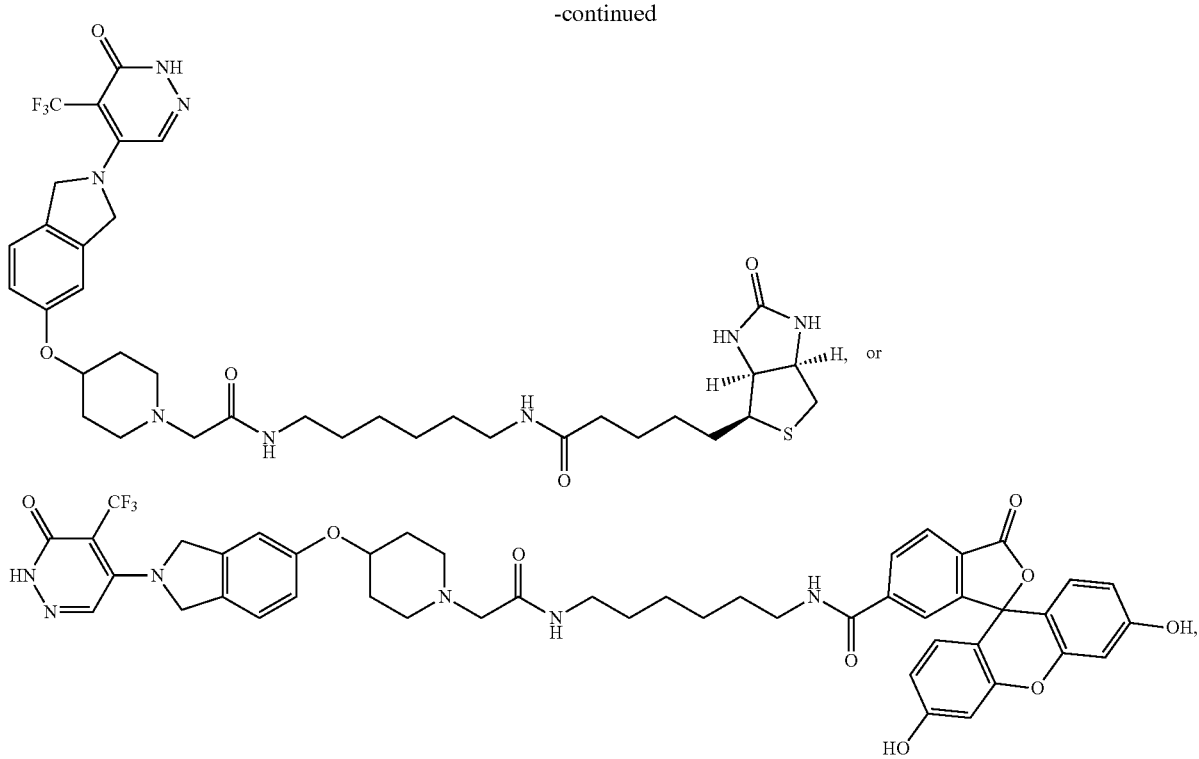

or a salt thereof.

9. The method of claim 7, further comprising identifying the test compound as an inhibitor for PARP if the signal produced by the acceptor fluorophore is decreased as compared to a reference level.

10. The method of claim 7, wherein the PARP is PARP1, PARP2, PARP3, PARP4, PARP5a, PARP5b, PARP6, TIPARP, PARP8, PARP9, PARP10, PARP11, PARP12, PARP13, PARP14, PARP15, or PARP16.

11. The method of claim 1, wherein L is:

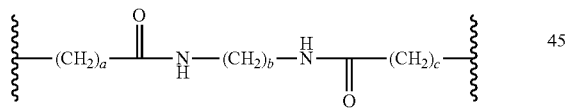

a is 0, 1, or 2;
b is 1-26; and
c is 0, 1, or 2;
wherein the sum of a+b+c is 1 to 26, or
L is a chain of 5-30 atoms in length comprising —(CH$_2$CH$_2$O)$_d$— wherein d is 2-10.

12. The method of claim 7, wherein L is:

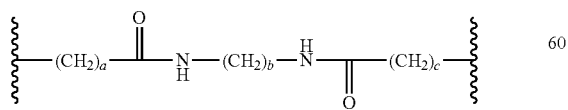

a is 0, 1, or 2;
b is 1-26; and
c is 0, 1, or 2;
wherein the sum of a+b+c is 1 to 26, or
L is a chain of 5-30 atoms in length comprising —(CH$_2$CH$_2$O)$_d$— wherein d is 2-10.

13. The method of claim 1, wherein A is:

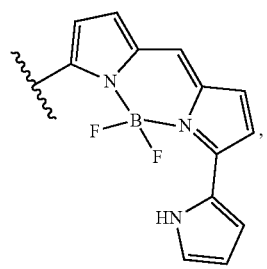

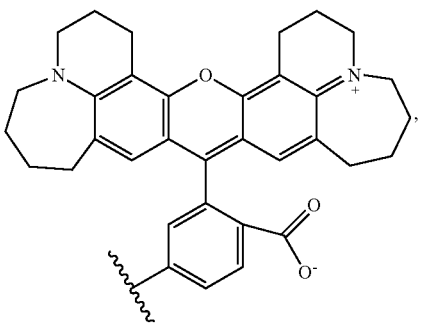

123
-continued
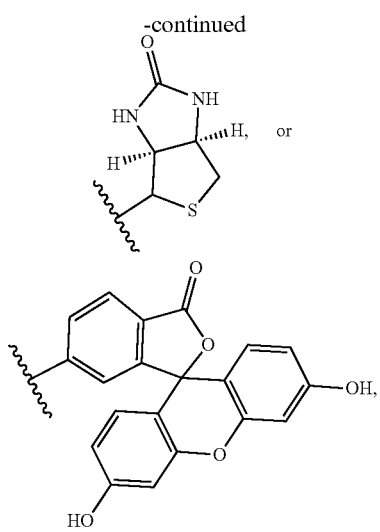
or a salt thereof.
14. The method of claim 7, wherein A is:
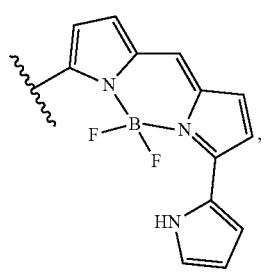
124
-continued
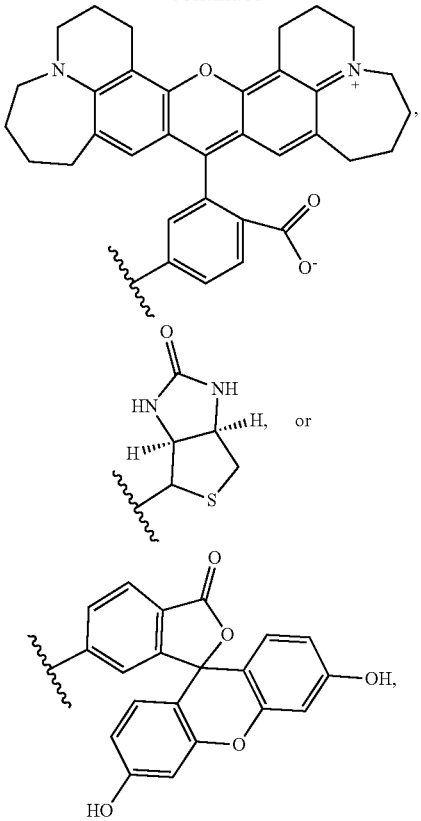
or a salt thereof.
* * * * *

UNITED STATES PATENT AND TRADEMARK OFFICE
CERTIFICATE OF CORRECTION

PATENT NO. : 11,293,927 B2  
APPLICATION NO. : 16/397410  
DATED : April 5, 2022  
INVENTOR(S) : Timothy J. N. Wigle et al.

Page 1 of 2

It is certified that error appears in the above-identified patent and that said Letters Patent is hereby corrected as shown below:

In the Claims

Column 117, Line 5, Claim 1, delete:

" 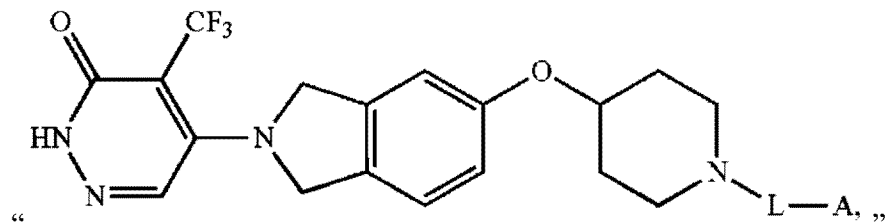 ,,

And insert:

-- 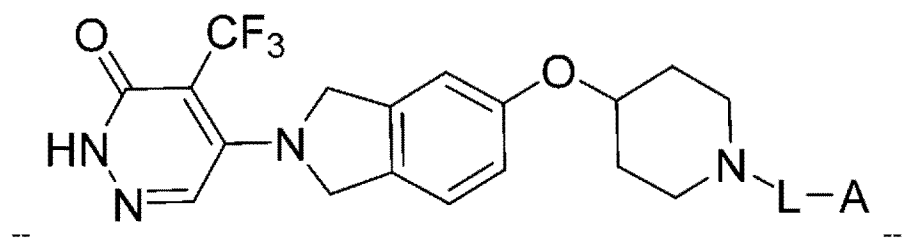 --

Column 117-118, in Claim 2, delete:

" 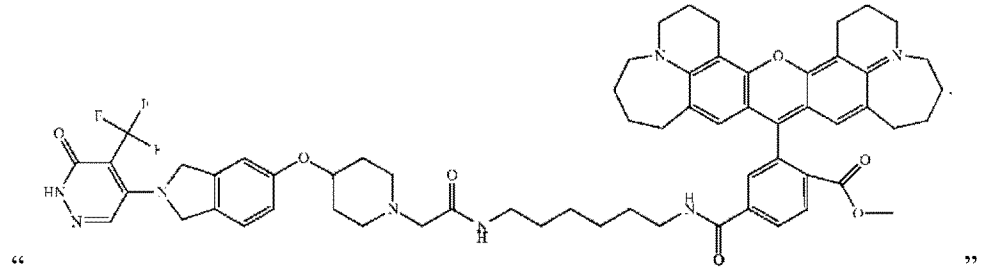 "

Signed and Sealed this  
Twelfth Day of July, 2022

*Katherine Kelly Vidal*

Katherine Kelly Vidal  
*Director of the United States Patent and Trademark Office*

And insert:
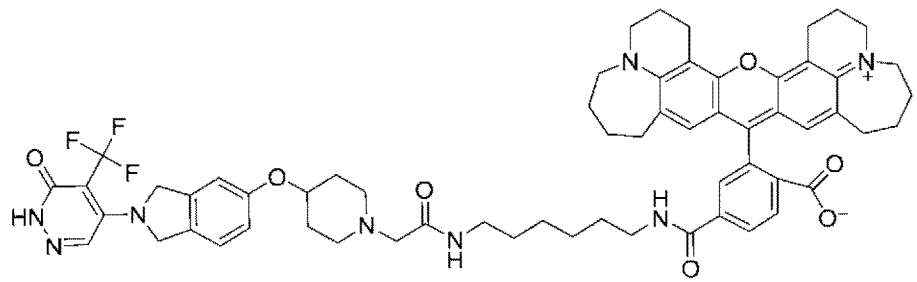
Column 119-120, in Claim 8, delete:
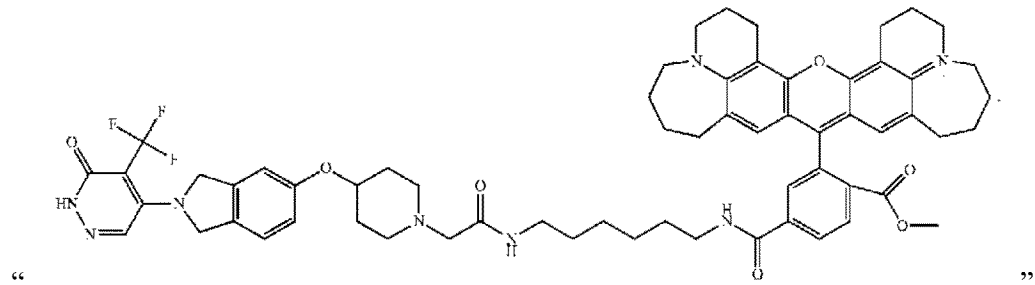
" "
And insert:
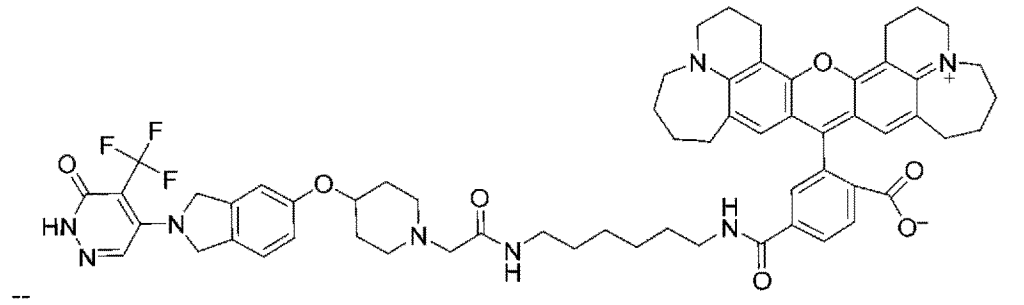
Column 121, Line 67, Claim 12, delete:
"cis"
And insert:
-- c is --